US012702478B2

(12) United States Patent
Park et al.

(10) Patent No.: US 12,702,478 B2
(45) Date of Patent: Aug. 11, 2026

(54) DEVICES, METHODS, AND COMPOSITIONS FOR THERMAL ACCELERATION AND DRUG DELIVERY

(71) Applicants: Rhode Island Hospital, Providence, RI (US); Brown University, Providence, RI (US)

(72) Inventors: William Keun Chan Park, Westerly, RI (US); Damian E. Dupuy, Centerville, MA (US)

(73) Assignees: Rhode Island Hospital, Providence, RI (US); Brown University, Providence, RI (US)

( * ) Notice: Subject to any disclaimer, the term of this patent is extended or adjusted under 35 U.S.C. 154(b) by 1018 days.

(21) Appl. No.: 17/751,605

(22) Filed: May 23, 2022

(65) Prior Publication Data

US 2022/0280233 A1 Sep. 8, 2022

Related U.S. Application Data

(60) Continuation-in-part of application No. 17/371,683, filed on Jul. 9, 2021, now Pat. No. 12,016,624, which (Continued)

(51) Int. Cl.

*A61B 18/18* (2006.01)

*A61B 18/14* (2006.01)

(Continued)

(52) U.S. Cl.

CPC .......... *A61B 18/1815* (2013.01); *A61B 18/14* (2013.01); *A61K 45/06* (2013.01);

(Continued)

(58) Field of Classification Search

CPC ................ A61B 18/1815; A61B 18/14; A61B 2018/00095; A61B 2018/00577;

(Continued)

(56) References Cited

U.S. PATENT DOCUMENTS 4,975,246 A 12/1990 Charm 5,057,106 A 10/1991 Kasevich et al.

(Continued)

FOREIGN PATENT DOCUMENTS

CA 2319446 C 9/2010

CA 2927528 A1 4/2015

(Continued)

OTHER PUBLICATIONS

Ahmed, M., et al., "Improved Coagulation with Saline Solution Pretreatment during Radiofrequency Tumor Ablation in a Canine Model," Journal of Vascular and Interventional Radiology, vol. 13, No. 7, 2002, pp. 717-724.

(Continued)

*Primary Examiner* — Michael F Peffley

*Assistant Examiner* — Bo Ouyang

(74) *Attorney, Agent, or Firm* — Nutter McClennen & Fish LLP

(57) ABSTRACT

A thermal accelerant can be used as a drug delivery vehicle to deliver one or more drugs to a target site. For example, in some embodiments, a carrier such as albumin or human serum albumin (HSA) can be impregnated with, or covalently attached to, an anti-tumor agent and delivered to a location proximate to a tumor of a patient. The carrier can be exposed to an energy source that structurally alters the carrier and releases the agent therefrom. The sources of energy can include one or more of microwave, radiofrequency, electrical pulse (electroporation) or sonar (HIFU or histotripsy). In some embodiments, the anti-tumor agent can be delayed release such that a portion of the agent is released from the carrier over an extended period of time. The incorporation of an anti-tumor agent in a thermal accelerant provides a thermal ablation-drug delivery combination therapy (e.g., a thermally-activated combination therapy).

19 Claims, 37 Drawing Sheets
(1 of 37 Drawing Sheet(s) Filed in Color)

Related U.S. Application Data is a division of application No. 16/708,416, filed on Dec. 9, 2019, now Pat. No. 11,076,916, which is a continuation-in-part of application No. 15/389,809, filed on Dec. 23, 2016, now Pat. No. 10,722,289.

(60) Provisional application No. 63/304,071, filed on Jan. 28, 2022, provisional application No. 63/192,253, filed on May 24, 2021, provisional application No. 62/381,251, filed on Aug. 30, 2016, provisional application No. 62/387,250, filed on Dec. 23, 2015.

(51) Int. Cl.
*A61K 45/06* (2006.01)
*A61B 18/00* (2006.01)

(52) U.S. Cl.
CPC ............... *A61B 2018/00095* (2013.01); *A61B 2018/00577* (2013.01); *A61B 2018/00595* (2013.01); *A61B 2018/00982* (2013.01)

(58) Field of Classification Search
CPC ........... A61B 2018/00595; A61B 2018/00982; A61K 45/06
See application file for complete search history.

(56) References Cited

U.S. PATENT DOCUMENTS

| | | | |
|---|---|---|---|
| 6,340,367 | B1 | 1/2002 | Stinson et al. |
| 6,530,944 | B2 | 3/2003 | West et al. |
| 7,074,175 | B2 | 7/2006 | Handy et al. |
| 8,563,501 | B2 | 10/2013 | Wagner et al. |
| 8,565,892 | B2 | 10/2013 | Nayfach-Battilana |
| 9,381,157 | B2 | 7/2016 | Santamore et al. |
| 10,722,289 | B2 | 7/2020 | Park et al. |
| 11,076,916 | B2 | 8/2021 | Park et al. |
| 11,497,554 | B2 | 11/2022 | Dupuy et al. |
| 2003/0028071 | A1 | 2/2003 | Handy et al. |
| 2004/0033160 | A1 | 2/2004 | MacPhee et al. |
| 2004/0210282 | A1 | 10/2004 | Flock et al. |
| 2005/0118187 | A1 | 6/2005 | Yu |
| 2005/0256360 | A1 | 11/2005 | Hainfeld et al. |
| 2006/0190063 | A1 | 8/2006 | Kanzius |
| 2007/0135875 | A1 | 6/2007 | Demarais et al. |
| 2007/0135877 | A1 | 6/2007 | Pringle |
| 2008/0171982 | A1 | 7/2008 | Mehier |
| 2010/0183728 | A1* | 7/2010 | Desai ...................... A61P 35/00 977/773 |
| 2010/0198210 | A1 | 8/2010 | Lanphere et al. |
| 2011/0033540 | A1 | 2/2011 | Daniloff et al. |
| 2011/0034916 | A1 | 2/2011 | Te et al. |
| 2011/0105825 | A1 | 5/2011 | Nayfach-Battilana |
| 2011/0152852 | A1 | 6/2011 | Cressman |
| 2011/0251545 | A1 | 10/2011 | Duffy et al. |
| 2012/0253188 | A1* | 10/2012 | Holland .................. A61B 6/12 600/431 |
| 2012/0289956 | A1 | 11/2012 | Marc |
| 2013/0053932 | A1 | 2/2013 | Wagner et al. |
| 2013/0261710 | A1 | 10/2013 | Won et al. |
| 2013/0266508 | A1 | 10/2013 | Luo et al. |
| 2013/0267940 | A1 | 10/2013 | Chiang et al. |
| 2013/0336897 | A1 | 12/2013 | Wolf et al. |
| 2014/0056822 | A1 | 2/2014 | Kadushin et al. |
| 2014/0094793 | A1 | 4/2014 | Sharonov |
| 2015/0182627 | A1 | 7/2015 | Kim et al. |
| 2015/0231269 | A1* | 8/2015 | Kaittanis ............ A61K 49/1854 514/263.24 |
| 2015/0265725 | A1* | 9/2015 | Peyman ............... A61B 5/0095 604/20 |
| 2016/0022976 | A1 | 1/2016 | Peyman |
| 2017/0182165 | A1 | 6/2017 | Park et al. |
| 2018/0153617 | A1 | 6/2018 | Dupuy et al. |
| 2019/0343581 | A1 | 11/2019 | Panescu et al. |
| 2020/0179049 | A1 | 6/2020 | Park et al. |
| 2021/0024494 | A1 | 1/2021 | Aktoudianakis et al. |
| 2021/0128694 | A1 | 5/2021 | Laurin et al. |
| 2021/0330382 | A1 | 10/2021 | Park et al. |
| 2022/0280233 | A1 | 9/2022 | Park et al. |
| 2023/0070990 | A1 | 3/2023 | Dupuy et al. |

FOREIGN PATENT DOCUMENTS

| | | | |
|---|---|---|---|
| CN | 102139096 | A | 8/2011 |
| CN | 103751102 | A | 4/2014 |
| EP | 3302263 | B1 | 1/2021 |
| GB | 2024007 | A | 1/1980 |
| WO | 2014031727 | A1 | 2/2014 |
| WO | 2016/197093 | A1 | 12/2016 |
| WO | 2017112931 | A1 | 6/2017 |
| WO | 2021119173 | A1 | 6/2021 |

OTHER PUBLICATIONS

Brace, CL, et al. 2009 Pulmonary thermal ablation: comparison of radiofrequency and microwave devices by using gross pathologic and CT findings in a swine model. Radiology. 251:705-11.

Brace, CL. Evaluation of a thermoprotective gel for hydrodissection during percutaneous microwave ablation: in vivo results. Cardiovasc Intervent Radiol. 2015, 38(3):722-30.

Brown, D., et al. "Society of Interventional Radiology Position Statement on Chemoembolization of Hepatic Malignancies." Journal of Vascular and Interventional Radiology (2006) 17(2): 217-23.

Canadian Office Action for Application No. 2,988,389, dated Aug. 11, 2022, 3 pages.

Canadian Office Action for Application No. 3,009,649, dated Jan. 12, 2023, 4 pages.

Charpentier, KP. Irreversible Electroporation for the Ablation of Liver Tumors. Are We There Yet? Arch Surg. 2012;147(11):1053-1061.

Chinese Office Action for Application No. 201680075913.7 mailed Aug. 30, 2021, 9 pages.

Chinese Patent Office, Decision of Rejection for Chinese Patent Application No. 201680075913.7 mailed Apr. 21, 2022, 10 pages.

Chu, KF et al. 2014. Thermal ablation of tumors: biological mechanisms and advances in therapy. Nat. Rev. Cancer 14: 199-208.

Correa-Gallego, C et al. 2014. A Retrospective Comparison of Microwave Ablation vs. Radiofrequency Ablation for Colorectal Cancer Hepatic Metastases. 2014, Ann Surg Oncol. 21(13): 258-264.4278-83.

Dodd, III, GD et al. Effect of variation of portal venous blood flow on radiofrequency and microwave ablations in a blood-pertused bovine liver model. 2013 Radiology. 267(1): 129-36.

Duan, X., et al. "Heat shock protein 70 expression and effect of combined transcatheter arterial embolization and radiofrequency ablation in the rabbit VX2 liver tumour model." Clinical Radiology (2014) 69(2):186-193.

Examination Report for European Application No. 16880144.7 dated May 3, 2022. 4 pages.

Extended European Search Report for Application No. EP 16804631.6 issued Apr. 17, 2019 (14 pages).

Extended European Search Report for European Application No. 16880144.7, dated Jul. 2, 2019, 8 pages.

Farrugia, A. Albumin Usage in Clinical Medicine: Tradition or Therapeutic? 2010, Transfusion Medicine Reviews 24(1): 53-63.

First Examination Report—India, Application No. 201817026986, dated Jun. 1, 2021, 6 pages.

Ginsburg, M., et al. "Comparison between transarterial chemoembolization in combination with radiofrequency ablation versus microwave ablation in the management of hepatocellular carcinoma." Journal of Vascular and Interventional Radiology (2013) 24(4) S43-44 (Abstract available).

Goovaerts, V et al., Molecular Interactions Between Serum Albumin Proteins and Keggin Type Polyoxometalates Studied Using Luminescence Spectroscopy. 2013, Phys. Chem. Chem. Phys., 15, 18378-18387,2015.

(56) References Cited

OTHER PUBLICATIONS

Haefliger, DN. Amphibian albumins as members of the albumin, alpha-fetoprotein, vitamin D-binding protein multigene family. 1989, Journal of Molecular Evolution 29 (4): 344-354.
International Preliminary Report on Patentability for International Application No. PCT/US2020/064082 mailed Jun. 23, 2022, 9 pages.
International Search Report and Written Opinion for International Application No. PCT/US2016/035995 mailed Oct. 7, 2016, 9 pages.
International Search Report and Written Opinion of the International Searching Authority in PCT/US16/68517 mailed Mar. 29, 2017 (3 pgs.).
International Search Report and Written Opinion of the International Searching Authority in PCT/US2020/064082 mailed Apr. 12, 2021 (12 pgs.).
Isfort, P., et al. "Efficacy of Magnetic Thermoablation Using SPIO in the Treatment of Osteoid Osteoma in a Bovine Model Compared to Radiofrequency and Microwave Ablation." Cardiovasc Intervent Radiol (2014) 37: 1053-1061.
Japanese Office Action for Application No. 2018-553044 dated Oct. 8, 2021, 3 pages.
Japanese Patent Office, Notice of Reasons for Refusal, for Application No. 2018-553044 dated Oct. 18, 2022, 3 pages.
Keisari, Y et al. Activation of local and systemic anti-tumor immune responses by ablation of solid tumors with Intratumoral electrochemical or alpha radiation treatments. 2014. Cancer Immunol. Immunother. 63: 1-9.
Lanuti, M et al. Radiofrequency Ablation for Stage I Non-Small Cell Lung Cancer: Management of Locoregional Recurrence. 2012, Ann Thorac Surg. 93(3): 921-8.
Lichenstein, HS et al. Afamin is a new member of the albumin, alpha-fetoprotein, and vitamin D-binding protein gene family. 1994, The Journal of Biological Chemistry 269 (27): 18149-54.
Lu, DS et al. Radiofrequency Ablation of Hepatocellular Carcinoma: Treatment Success as Defined by Histologic Examination of the Explanted Liver. 2005, Radiology. 234(3):954-60.
Manthe, R., et al., "Tumor Ablation and Nanotechnology," Molecular Pharmaceutics, vol. 7, No. 6, Dec. 6, 2010, pp. 1880-1898.
Mizukoshi, E et al. Enhancement of tumor-associated antigen-specific T cell responses by radiofrequency ablation of hepatocellular carcinoma. 2013, Hepatology 57: 1448-1457.
Moreland, AJ et al. Evaluation of a thermoprotective gel for hydrodissection during percutaneous microwave ablation: in vivo results. 2015, Cardiovasc Intervent Radiol. 38(3):722-30.
Mostafa, E., et al. "Optimal strategies for combining transcatheter arterial chemoembolization and -adiofrequency ablation in rabbit VX2 hepatic tumors." J Vasc Intery Radiol. (2008) 19(12):1740-8.
Nelson, SO et al., Factors influencing the dielectric properties of agricultural and food products. 2012, Journal of Microwave Power and Electromagnetic Energy, 46 (2) pp. 93-107.
Ninh, C et al. Photoresponsive hydrogel networks using melanin nanoparticle photothermal sensitizers. 2014 Biomater. Sci., 2, 766-774.
Park, W., et al., "A novel thermal accelerant for augmentation of microwave energy during image-guided tumor ablation," Progress in Biomedical Optics and Imaging, SPIE—International Society for Optical Engineering, Bellingham, WA, US, SPIE vol. 10066, Jan. 29, 2017, 3 pages.
Park, W., et al., "Evaluation of a Novel Thermal Accelerant for Augmentation of Microwave Energy during Image-guided Tumor Ablation," Theranostics, vol. 7, No. 4, Feb. 26, 2017, pp. 1026-1035.
Pethig, R. Dielectric Properties of Biological Materials: Biophysical and Medical Applications. 1984, IEEE Transactions on Electrical Insulation vol. EI-19 No. 5.
Pillai, K et al. Heat sink effect on tumor ablation characteristics as observed in monopolar radiofrequency, bipolar radiofrequency, and microwave, using ex vivo calf liver model. 2015, Medicine (Baltimore) 94(9):e580) 10 pgs.
Qian, T., et al. "Diffusion-weighted magnetic resonance imaging to evaluate microvascular density after ransarterial embolization ablation in a rabbit VX2 liver tumor model." Magnetic Resonance Imaging 32 (2014):1052-1057.
Schoentgen, F et al. Complete amino acid sequence of human vitamin D-binding protein (group-specific component): evidence of a three-fold internal homology as in serum albumin and a-fetoprotein. 1986, Biochimica et Biophysica Acta (BBA)—Protein Structure and Molecular Enzymology 871 (2): 189-198.
Siddiqui, N et al., A study on viscosity, surface tension and volume flow rate of some edible and medicinal oils. 2013, Int. J Sci, Environ and Tech., 2(6) 1318-1326.
Wang, S. et al., Viscosity-Lowering Effect of Amino Acids and Salts on Highly Concentrated Solutions of Two IgG1 Monoclonal Antibodies. Mol. Pharmaceutics 2015, 12, 4478-87.
Willatt, J et al. Image-guided therapies in the treatment of hepatocellular carcinoma: A multidisciplinary perspective. 2015, World J Hepatol 7(2): 235-244.
Canadian Office Action for Application No. 2,988,389, dated Apr. 14, 2023, 5 pages.
Canadian Office Action for Application No. 2,988,389, dated Mar. 24, 2025, 4 pages.
Canadian Office Action for Application No. 3,009,649, dated Nov. 14, 2023, 3 pages.
Extended European Search Report for European Application No. 20899590.2 dated Dec. 1, 2023, 9 pages.
Extended European Search Report for European Application No. EP22811936, dated Apr. 14, 2025, 14 pages.
Goldberg, S. Nahum et al., "Percutaneous Tumor Ablation: Increased Necrosis with Combined Radio-Frequency Ablation and Intratumoral Doxorubicin Injection in a Rat Breast Tumor Model", Radiology, vol. 220, Jul. 19, 2001.
International Search Report and Written Opinion for International Application No. PCT/US2016/035995 mailed Sep. 23, 2022, 14 pages.
Park, W., et al., "HeatSYNC™ Gel as a Thermal Accelerant and Drug Delivery System," Jan. 1, 2022 (Jan. 1, 2022), XP093264822,Retrieved from the Internet: URL:https://www.theromicsinc.com/wp-content/uploads/2024/10/PosterSIO_2022.pdf.

* cited by examiner

Albumin 500 NaCl X 1.5 cm

■ NaCl 50
▾ NaCl 25
▴ NaCl 100
● NaCl150
○ NaCl 0
◆ Control No Albumin No NaCl

Temperature (°C)

t (sec)

Temperature (°C)

[NaCl]

2000

2010

2310

2420

2500

2520

2620

DEVICES, METHODS, AND COMPOSITIONS FOR THERMAL ACCELERATION AND DRUG DELIVERY

CROSS REFERENCE TO RELATED APPLICATIONS

This patent application claims the benefit of U.S. Provisional Patent Application No. 63/192,253, filed on May 24, 2021, and titled "DEVICES, METHODS, AND COMPOSITIONS FOR DRUG DELIVERY," and U.S. Provisional Patent Application No. 63/304,071, filed on Jan. 28, 2022, and titled "DEVICES, METHODS, AND COMPOSITIONS FOR THERMAL ACCELERATION AND DRUG DELIVERY."

This patent application is also a continuation-in-part of U.S. patent application Ser. No. 17/371,683, filed on Jul. 9, 2021, and titled "THERMAL ACCELERANT COMPOSITIONS AND METHODS OF USE,", which is a divisional of U.S. patent application Ser. No. 16/708,416, filed on Dec. 9, 2019, and titled "Thermal Accelerant Compositions and Methods of Use," (now U.S. Pat. No. 11,076,916), which is a continuation-in-part of U.S. patent application Ser. No. 15/389,809, filed on Dec. 23, 2016, and titled "THERMAL ACCELERANT COMPOSITIONS AND METHODS OF USE," (now U.S. Pat. No. 10,722,289), which claims the benefit of, and priority to, U.S. Provisional Patent Application No. 62/381,251, filed on Aug. 30, 2016, and U.S. Provisional Patent Application No. 62/387,250, filed Dec. 23, 2015.

The seven above noted patent applications are hereby incorporated herein by reference, in their entireties, including their drawings and appendices.

TECHNICAL FIELD

The present disclosure relates to systems, devices, and methods for treating subjects with one or more of microwave, radiofrequency, electrical pulse (electroporation) or sonar (HIFU or histotripsy). In particular, disclosed are thermal accelerants that can be used as a drug delivery vehicle to deliver one or more substances, such as anti-tumor agents, to a target site. In some embodiments, the anti-tumor agent can be delayed release such that a portion of the agent is released from the carrier over an extended period of time. The incorporation of an anti-tumor agent in a thermal accelerant provides a thermal ablation-drug delivery combination therapy.

BACKGROUND

Various embodiments relate to methods, materials and equipment for hyperthermal tissue ablation, that is, to the application of energy to heat and destroy tissue such as a tumor located in an internal organ, vessel, bone or other site, without surgery. Among the instruments used for such ablation are monopolar (MP) radiofrequency antennae; bipolar (BP) radiofrequency electrodes; and microwave antennae. These may be inserted transdermally, or via a catheter sheath to access a treatment site, and each has its characteristic action and actuation parameters. The use of such an antenna device for locally heating tissue to achieve hyperthermal tissue ablation may require a characteristic operating duration, applied power level and frequency and type of electromagnetic drive, and the proper selection or setting of these parameters and positioning of the antenna tip will generally depend upon the tissue type as well as the size and shape of the target tumor. Among the different heating modalities, microwave ablation may be applied to internal tissue sites using a needle-like antenna carried in a probe or hand piece, and the active antenna may be imaged, for example by CT imaging, to guide placement precisely in relation to a target tissue site. The target itself may be, or have been, identified by diagnostic imaging, by the same or another medical imaging modality.

Such image-guided microwave tumor ablation has been recognized as a safe, minimally invasive and cost-effective cancer treatment for discrete tumors, and may sometimes be a treatment of choice when other factors render surgery dangerous or otherwise inadvisable.

However, while placement of the microwave antenna may be made anywhere in the body using a simple surgical ablation needle hand piece or commonly available trocar and catheter for placement of the antenna and cable, as appropriate for the intended target site, the effective heating range of a microwave ablation antenna results in an oval- or oblong-shaped ablation region that extends only a relatively small distance around the ablation antenna. Its heating effects may vary, to some extent, depending on the local tissue conditions. While this short effective range will limit unintended damage to most nearby healthy tissue structures, it also presents a drawback, in that microwave ablation drops off rapidly in only a few centimeters, and the ablation may be irregular due to either the rate of microwave heat generation at the site, or heat conduction away from the site into adjacent tissue, or variations in tissue conductivity and dielectric constant (which may be different for each patient). As a result, when treated by microwave hyperthermal ablation, tumors experience a relatively high rate of recurrence (ca. 30%) due to loci of incomplete ablation. The incomplete ablation and consequent tumor cell survival and tumor recurrence may occur because some undetected tumor cells lie outside of the effective ablation zone; because local variations of the tissue characteristics result in intrinsically lower heat generation; because surviving tumor cells are in the vicinity of a blood vessel that acted as a 'heat sink' limiting the temperature rise in a portion of the targeted region during the ablation procedure by increasing thermal conduction away from the intended ablation site; or because the drop-off or shadowing in the far field resulted in great variations of effective temperature around the nominal target temperature.

The effective ablation zone for a microwave needle/antenna is typically an almond-shaped region extending only 2-4 cm from the microwave antenna, as shown in FIG. 1A, which illustrates a microwave needle/antenna A inserted into a tumor T in a patient's liver L such that actuation heats an ablation zone AZ that covers the center, but not the fringes, of the tumor. FIG. 1B shows an actual image of a real-life liver tumor that had metastasized from and presented with a left-side colon cancer. Following resection of the colon primary, the patient was treated with 8 cycles of leucovorin, fluorouracil, and oxaliplatin, as well as bevacizumab (Avastin). The liver tumor, however, was deemed unresectable owing to concerns about functional liver reserve, so it was treated by microwave ablation of tumors in several segments, of which one is indicated by the thick arrow in FIG. 1B. The tumor measured 2.7 cm and abutted the left hepatic vein (thin arrow). Following the ablation procedure a follow-up Positron-emission tomographic scan image was taken. As shown in FIG. 1C, increased fluorodeoxyglucose activity (thick arrow) was observed in a small region, at a location consistent with the presence of residual tumor adjacent to the left hepatic vein (FIG. 1C, thin arrow). Heat sink was implicated as a possible contributing cause of the residual disease. The patient was alive 3 years after initial diagnosis.

Other factors may contribute to sub-optimal ablation efficacy, including incomplete knowledge of the target tissue and its microwave heating characteristics, irregular shape or size of the target, and presence of tissue that limits access or placement of the antenna.

SUMMARY OF VARIOUS EMBODIMENTS OF THE INVENTION

In accordance with some embodiments, methods and systems ablate tissue. To that end, the methods and systems may introduce a first applicator to a target site in a patient; position a first thermal accelerant to define a nominal ablation zone for the target site, the thermal accelerant comprising a chaotrope; and activate the first applicator to excite particles of the first thermal accelerant for heating the first thermal accelerant to a specific temperature to ablate the target site.

In some embodiments, the method can further apply the first thermal accelerant to a surface of a tissue at a target site to cauterize the target site. In some embodiments, positioning the first thermal accelerant can further include positioning the accelerant at an outer-boundary of the target site. Moreover, the method can further introduce a second applicator or a second thermal accelerant to the target site, the second applicator and the second thermal accelerant being positioned in a substantially rhombal shape with the first applicator and the first thermal accelerant. Further, the first applicator or the second applicator can include an electrode having one or more energy emitting devices thereon. Further still, the method can further include passing one or more of the first applicator and the first thermal accelerant through the target site under image guidance. Among other things, the first thermal accelerant may coagulate to become integral with the ablated tissue. In some embodiments, the specific temperature can be between approximately 60 degrees Celsius to approximately 170 degrees Celsius.

In accordance with alternate embodiments, the first thermal accelerant may include material having a high dipole moment that is configured to convert radiofrequency to thermal energy. The first thermal accelerant may be positioned to enhance heating by applying electric energy in a far field, peripheral drop-off, or tissue variation region to thereby extend ablation effects to said regions. The dipole moment may have a value that ranges from about 7 Debye to about 1,000 Debye. Among other things, the first applicator can emit one or more of microwave energy, radiofrequency energy, and a pulse of energy of electroporation. The target site can include one or more of a tumor and a tissue target in a patient.

In accordance with alternate embodiments, the first thermal accelerant may remain substantially stationary within the target site after deposition. Among other things, the first thermal accelerant may be positioned between the first applicator and healthy tissue to prevent healthy tissue from overheating. In some embodiments, the method can further include positioning the first thermal accelerant between an ablation site and a heat sink to modulate conduction of heat away from the ablation site. Moreover, the method can include delivering the thermal accelerant from the first applicator.

In accordance with other embodiments, various compositions of thermal accelerant can be used for ablation. The composition can include a thermal accelerant having a polymer configured to become gelatinous or solidify at body temperature or above to become relatively immobilized after positioned within the target site, a chaotrope configured to adjust charge distribution within the polymer, and an imaging component configured to allow image-guided verification of the thermal accelerant within a body of a patient. The thermal accelerant, when exposed to an amount of ablative energy, has values of electrical conductivity and loss factor that are up to 5 times or greater than values of electrical conductivity and loss factor in living tissue when exposed to an equal amount of ablative energy without a thermal accelerant. In embodiments, the polymer may function as an imaging component.

The viscosity of the thermal accelerant can range from approximately 50 centiPoise to approximately 25,000 centiPoise. The chaotrope can be selected from the group consisting of: calcium chloride, cesium chloride, lithium chloride, potassium chloride, rubidium chloride, sodium chloride, sodium citrate, trisodium citrate, sodium tryptophanate, citric acid, octanoic acid, and a combination thereof. In some embodiments, the cesium chloride may tumble synchronously to the alternating electric field fueled by its intrinsic dipole moment to generate heat. Moreover, the polymer can include one or more of albumin, DNA, RNA, glycoproteins or glycopolymers such as IgA, IgG, or other immunoglobulins. The chaotrope may be present in the thermal accelerant in concentrations between 1 mg/mL and 500 mg/mL, or concentrations between 2 mg/mL and 150 mg/mL, or concentrations between 5 mg/mL and 20 mg/mL. The albumin may be present in the thermal accelerant in concentrations between 50 mg/mL and 700 mg/mL, or in concentrations between 150 mg/mL and 600 mg/mL, or in concentrations between 300 mg/mL and 600 mg/mL, or in concentrations between 450 mg/mL and 550 mg/mL, or even at a concentration of 500 mg/mL.

In an exemplary embodiment of the TA being used for drug delivery, the substance can include a carrier, in situ formation of a "structurally altered" carrier molecule with desired drugs upon exposure to external energy, where the term "structurally altered" refers to all stages of irreversible change of the carrier molecule brought about by external energy sources which include sources of energy other than physiological body heat energy. The sources of energy can include one or more of microwave, radiofrequency, electrical pulse (electroporation) or sonar (histotripsy). A concentration of the carrier in the formulation can range from approximately 30 mg/mL to approximately 600 mg/mL. In some embodiments, one or more of acids, bases, metal or metal ions, salts, buffer or chaotropes can be added to adjust polarity of the carrier molecule for kinetic movements during ablation.

In accordance with other embodiments, a drug delivery composition includes a carrier that includes a polymer configured to coagulate when exposed to prescribed energy from an energy source to become relatively immobilized after being positioned within a target site, and drug configured to be associated with the carrier, the drug being configured to be released following exposure of the prescribed energy from the energy source, wherein the carrier is configured to be structurally altered upon exposure to the prescribed energy from the energy source to release the drug. The drug may be configured such that a portion of the drug is released from the carrier over at least 48 hours. The drug may be associated with the carrier by at least one of protein binding or covalent bonding. A concentration of the carrier may range from approximately 30 mg/mL to approximately 600 mg/mL.

The polymer may comprise albumin or structurally modified albumin. Structurally altered may include denaturation of the carrier. Denaturation of the carrier may alter at least one of: a protein binding percentage between the drug and the carrier; or a shape of the carrier.

In some embodiments, the energy source may include one or more of microwave, radiofrequency, electrical pulse (electroporation) or sonar (HIFU or histotripsy).

The drug delivery composition may further include a chaotrope configured to adjust the charge distribution within the carrier.

In some embodiments, the polymer may include one or more of DNA, RNA, glycoproteins or glycopolymers such as IgA, IgG, or other immunoglobulins.

In some embodiments, the drug may include one or more of PD-1 Pembrolizumab (Keytruda), Nivolumab (Opdivo), Cemiplimab (Libtayo), PD-L1 Atezolizumab (Tecentriq), Avelumab (Bavencio), Durvalumab (Imfinzi) and CTLA4 Ipilimumab (Yervoy), siRNA, peptides, proteins, immunogens, RNA, mRNA, DNA, or nucleoside analog-based agents.

In some embodiments, the drug may include one or more of kinase inhibitors, or doxorubicin, taxol, or other non-kinase anti-tumor agents.

In some embodiments, the drug may include a drug for targeting macrophages in cancer immunotherapy comprises one or more of: CSF1 (MCS 110); CCL2 (CNTO 888); CCR2 (BMS-813160, CCX872-B, MLN1202, PF-04136309); SIRPa (TTI-622, CC-95251, BI 765063, FSI-189); TIE 2 (CEP-11981, Regorafenib, Arry-614); Arginase (INCB001158); HER2 (CAR-macrophage); GC vitamin D-binding protein (EF-022); CD40 (SEA-CD40, APX005M, CP870,893, R07009879, CDX-1140, SGN-40, HCD122, 2141 V-11, ADC-1013, LVGN7409, Chi Lob 7/4, NG-350A); BTK (Ibrutinib, Acalabrutinib, Zanubrutinib); CSF1R (PLX-3397, BLZ945, ARRY-382, JNJ-40346527, IMC-CS4, FPA008, RO5509554, TPX-0022, DCC-3014, Q702, SNDX-6532); or CD47 (Hu5F9-G4, TTI-621, AO-176, IBI322, ZL 1201, CC-90002, HX009, IBI188, SRF231, AK117, IMC-002)

In some embodiments, the drug may include a drug for targeting cGAS-STING-TBK1 signaling pathway with at least one or more of ADU-S100, MK-1454, MK-2118, BMS-986301, GSK3745417, SB-11285, or IMSA-101.

In some embodiments, the drug may include a drug for targeting cancer vaccines TLR and STING agonists: target RIG-I/MDAS and TLR3 (poly-ICLC); TLR4 (G100); TLR7/8 (NKTR-262, resiquimod); TLR9 (CpG ODN SD-101, (VLP) excapsulated-TLR9 agonist CMP-001); STING (MK1454, E7766, ADU-S100, BMS-986301, SB-11285) FLT3L and CD40 agonists: target (examples of agonists) rhFLT3L (CDX-301); Agonistic anti-CD40 antibody (APX005M, CDX-1140, SEA-CD40).

In accordance with other embodiments, a method of delivering a drug to a patient includes positioning a carrier/drug composition within a location of the patient, the carrier/drug composition comprising a polymer carrier and a drug bound to the carrier; and structurally altering the carrier by applying energy from an energy source to the carrier/drug composition to coagulate the carrier and render the carrier relatively immobilized at the location of the patient, receipt of the energy causing the carrier to release the drug within the location of the patient.

The energy source may include at least one or more of microwave, radiofrequency, electrical pulse (electroporation), or sonar (histotripsy). The receipt of the energy may further include causing ablation of the location of the patient in the presence of the carrier/drug composition. The ablation of the location of the patient in the presence of the carrier/drug composition may result in a larger ablation volume and a more spherical ablation volume shape than ablation without the carrier/drug composition. The increase in the volume and spherical shape of the ablation volume may be dose-dependent.

In accordance with other embodiments, a thermally-activated combined treatment composition includes a therapeutic agent, and a thermal accelerant configured to: enhance ablation treatment, be impregnated with the therapeutic agent; and elute the therapeutic agent after exposure to energy from an energy source wherein the combined treatment composition is thermally activated by exposure to energy from an energy source.

The therapeutic agent may be associated with the thermal accelerant by at least one of protein binding or covalent bonding.

After the thermal accelerant is exposed to the energy from the energy source, the thermal accelerant may be configured to become coagulated and become coupled with the ablated tissue. After the thermal accelerant is exposed to the energy from the energy source, thermal accelerant may be configured to begin to elute a portion of therapeutic agent.

The thermal accelerant may include a carrier comprising an albumin, an ionic component comprising at least one chaotrope, and an imaging component. The albumin may include human serum albumin, or bovine serum albumin. The chaotrope may include at least one of calcium chloride, cesium chloride, lithium chloride, potassium chloride, rubidium chloride, sodium chloride, sodium citrate, trisodium citrate, sodium tryptophanate, citric acid, octanoic acid, or a combination thereof. The imaging component may include at least one of NaCl, CsCl, or albumin. In embodiments, the imaging component may be human serum albumin, or bovine serum albumin. In embodiments, the imaging component may include cesium, tantalum, iohexol, ethiodized polymers such as PLGA, PEG, albumin can be utilized. For ultrasound imaging, polymers have been found to be in general hypoechoic. In embodiments, the imaging component may include iodixanol (Visipaque), iohexol (Omnipaque), iopamidol (Isovue), iopromide (Ultravist), ioversol (Optiray), ioxilan (Oxilan), Gadavist (gadobutrol), Dotarem (gadoterate meglumine), Eovist (gadoxetate disodium), Magnevist (gadopentetate dimeglumine), Vasovist (gadofosveset trisodium), Teslascan (mangafodipir), Prohance (gadoteridol), OptiMARK (gadoversetamide), Omniscan (gadodiamide), Multihance (gadobenate dimeglumine), GastroMARK (ferumoxsil), Feridex (ferumoxides), Clariscan (gadoterate meglumine), Ablavar (gadofosveset trisodium), Definity (perflutren), Optison (perflutren), and Definity RT (perflutren).

When the thermal accelerant is exposed to the energy source, the energy source may be configured to begin to denature the albumin, and the denatured albumin may be configured to become coagulated; and may release the impregnated drug.

In accordance with other embodiments, a drug delivery carrier composition includes a carrier that includes a polymer configured to coagulate when exposed to energy from an energy source to become relatively immobilized after being positioned within a target site, the carrier being configured to contain a drug, the carrier being configured to enable the drug to be released after exposure to the energy from the energy source, and the carrier being configured to be structurally altered upon exposure to the energy from the energy source.

The polymer may include human serum albumin. The carrier composition may further include trisodium citrate, sodium tryptophanate, citric acid, and octanoic acid.

BRIEF DESCRIPTION OF THE FIGURES

The patent or application file contains at least one drawing executed in color. Copies of this patent or patent application publication with color drawing(s) will be provided by the Office upon request and payment of the necessary fee.

These and other features of the invention will be understood from the Figures and Description below, taken together with the Claims appended hereto, wherein FIG. 1A schematically shows non-overlapping ablation and tumor regions of a prior art microwave hepatic tumor ablation treatment;

DETAILED DESCRIPTION

Illustrative embodiments apply a strong energy absorber, a 'heat substrate' (HS) or 'thermal accelerant' (TA), to a tissue site to locally modulate the rate, extent or endpoint of temperature increase to achieve effective hyperthermal ablation of the tissue with an energy source (e.g., a microwave or radio frequency (RF) antenna, such as an image-guided transdermal microwave antenna). Moreover, some embodiments are configured to provide effective localized drug delivery. To that end, some embodiments may be implemented as a system having a carrier formed at least in part from a polymer configured to become relatively immobilized after being positioned within a target site. A drug associated with the carrier may be released following exposure to the energy source, providing therapeutic treatment to the localized area of the polymer. Details of various embodiments are discussed below.

In one embodiment, a reverse phase polymer is used as a carrier and is injected as a fluid to desired locations in or around a relevant tissue site. The polymer is liquid, and it gels, becomes gelatinous or even solidifies at body temperature or above, so it either is, or quickly becomes, immobilized and stays localized at the delivery site. The polymer may be one that changes state and expels liquid (e.g., water) at temperatures consistent with ablation procedures. In one embodiment, the polymer also contains a salt; use of cesium chloride has been found to greatly increase the microwave/heating interaction and also to render the accelerant visible under CT or MRI, thus allowing image-guided verification of localization prior to RF or microwave excitation. Other imaging modalities, such as ultrasound may be used for image guidance. The polymer with appropriate characteristics may be one such as a block-co-polymer PLGA-PEG-PLGA consisting of polyethylene glycol, which is covalently esterified by an FDA-approved poly lactic-co-glycolic acid on both ends. In operation, a range of parameters may be varied to establish ablation response as a function of microwave conditions (i.e., power, frequency, ablation period and distance) in a representative tissue, such as a pig or calf liver. (see, for example, the modeling protocols in Pillai K, Akhter J, Chua T C, Shehata M, Alzahrani N, Al-Alem I, Morris D L. 2015. Heat sink effect on tumor ablation characteristics as observed in monopolar radiofrequency, bipolar radiofrequency, and microwave, using ex vivo calf liver model. Medicine (Baltimore) 94(9):e580). In another embodiment the thermal accelerant is a preparation of a serum albumin or other albumin, as described further below, together with certain electrolytes that condition its viscosity, microwave energy absorbance or thermal accelerant properties, and preferably also provide imaging under one or more medical imaging modalities such as MRI, ultrasound or x-ray CT imaging.

Example 1

Figure 1A:
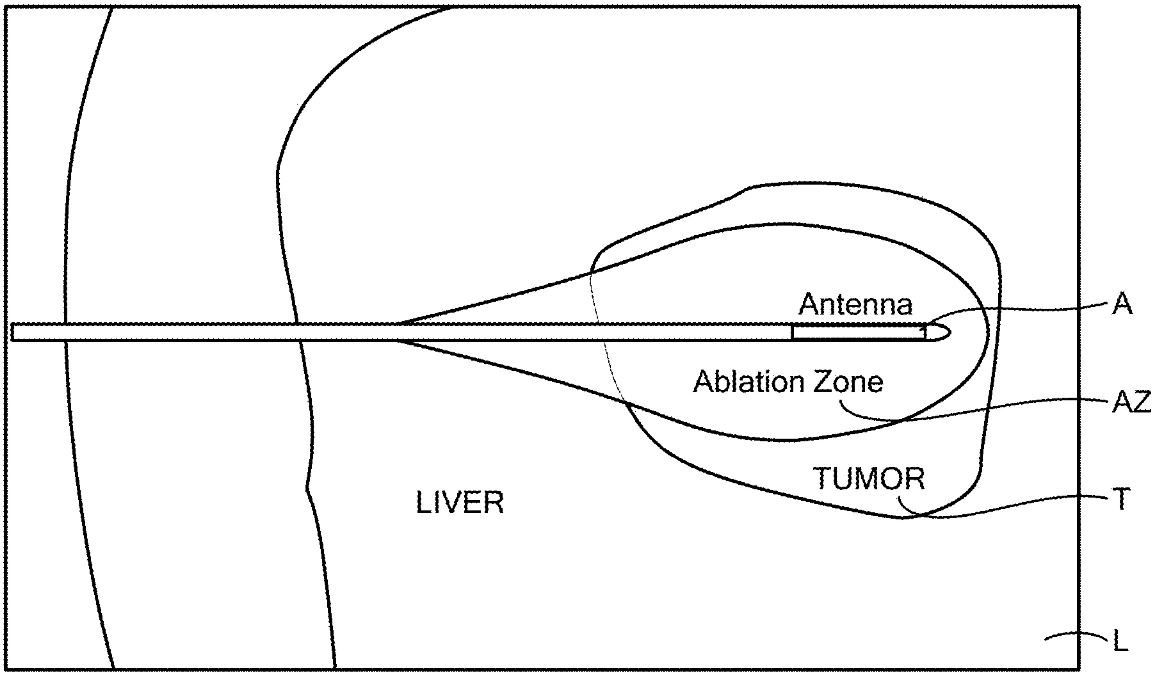
FIG. 1B shows a metastatic tumor in the liver of a patient and abutting the hepatic vein.
FIG. 1C is a PET scan of that site showing residual tumor growth suggesting that heat sink effect was a contributing cause of the residual disease.
Figure 1B:
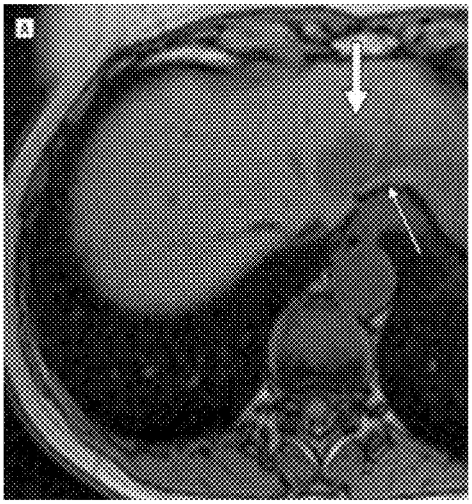
Figure 1C:
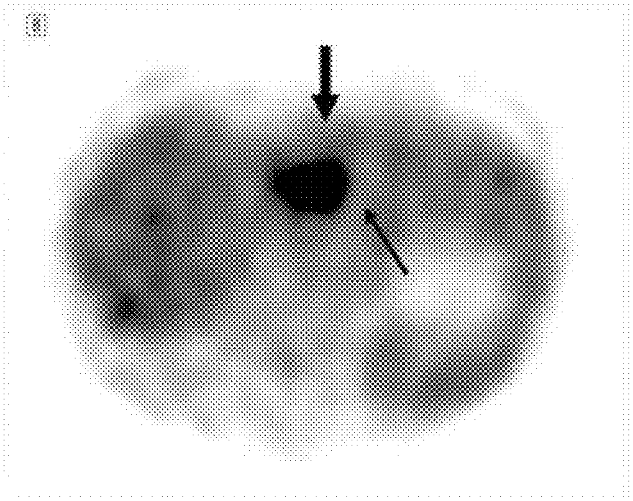

To mitigate the problem of inadequate heating, applicants devised a heat substrate to selectively increase heating and, by suitable placement, avoid undesirable cooling or 'heat sink' effects. This substrate of one embodiment is made of cesium chloride (CsCl) and is compounded in a reverse phase transition polymer to be positioned, and then activated by microwave energy from a distance. The reverse phase transition polymer, which may, for example be a PLGA-PEG-PLGA block copolymer of suitable viscosity, transforms into a gel at body temperature or above and with the cesium chloride salt strongly responds to microwave radiation and locally increases the temperature to more effectively ablate tumor cells that lie just outside of ablation zone AZ of FIGS. 1A, 1B and 1C. Furthermore, this heat substrate is an excellent contrast agent by itself, and was found to be visible under CT imaging. These properties make it particularly efficacious for treating solid tumors, where a physician can control the amount, the location(s) and the concentration of the heat substrate delivered to and fixed at locations about the targeted tumor to ensure complete ablation. Moreover, for larger or irregularly-shaped tumors, several microwave antennae may be positioned under image guidance to completely cover the tumor with a corrected/enhanced heat distribution.

Figure 2A:
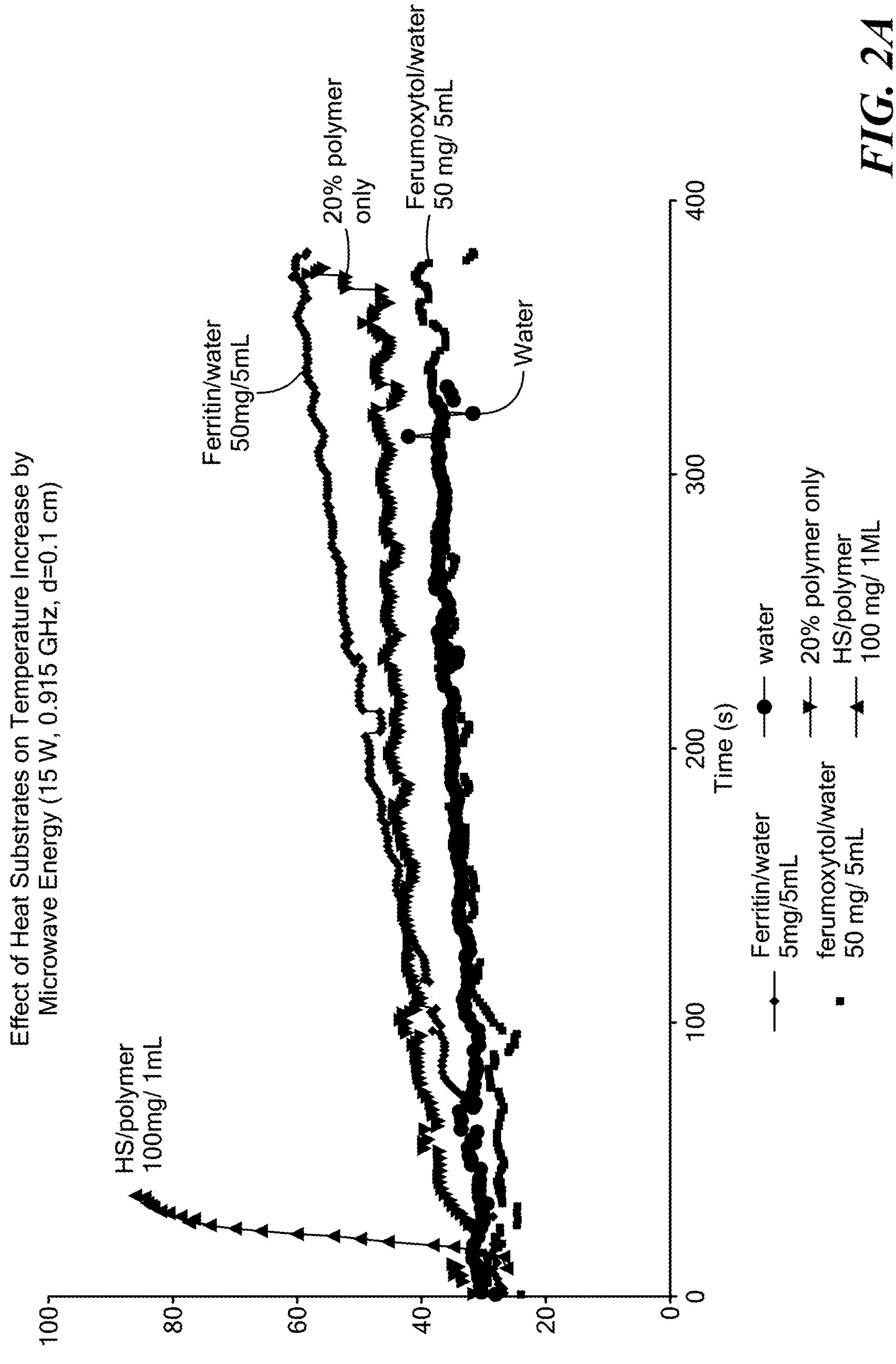
FIG. 2A shows effective rates of temperature increase by microwave heating for different fluids.
Figure 2B:
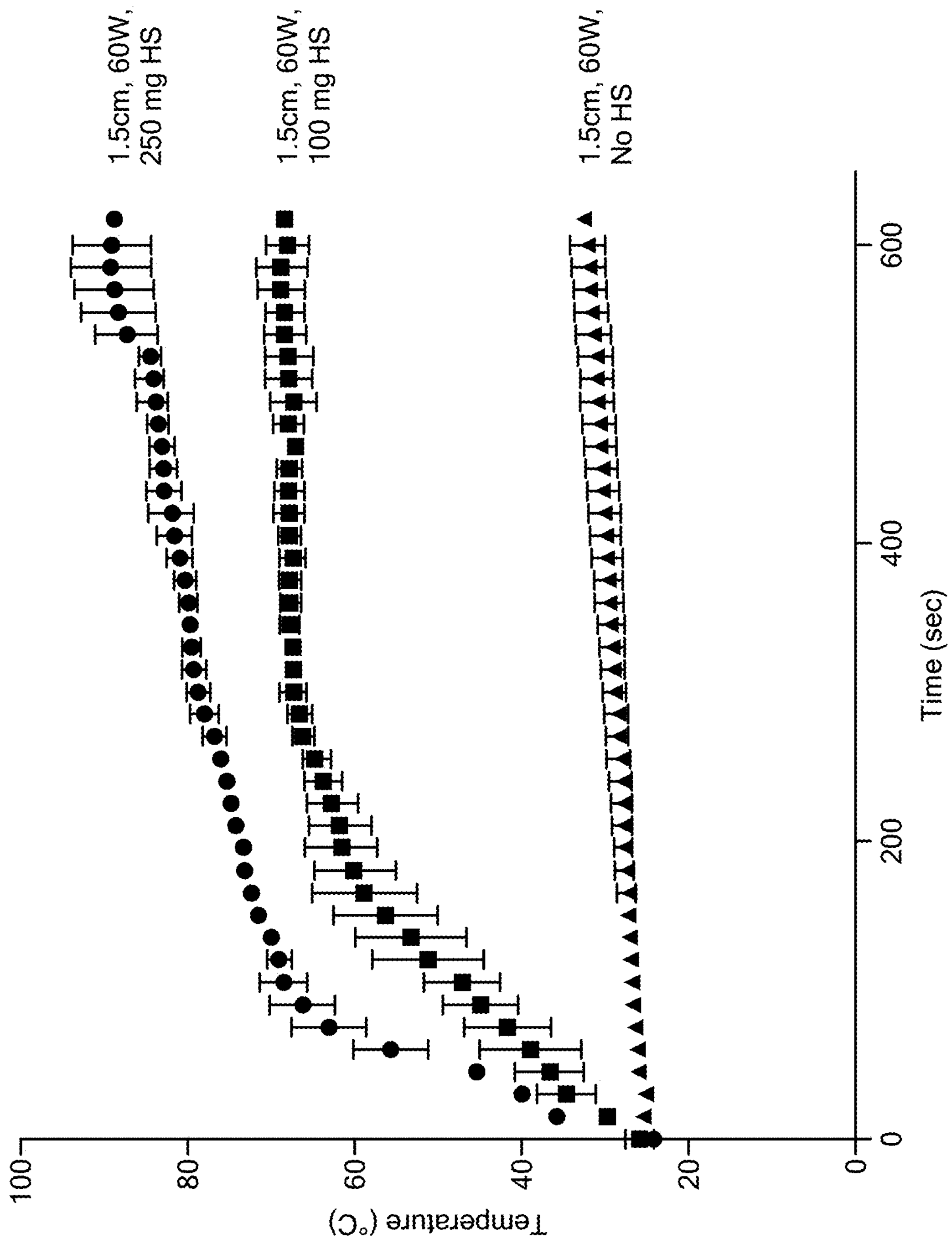
FIG. 2B shows effective rates of temperature rise for untreated tissue and for different heat substrate formulations.
Figure 2C:
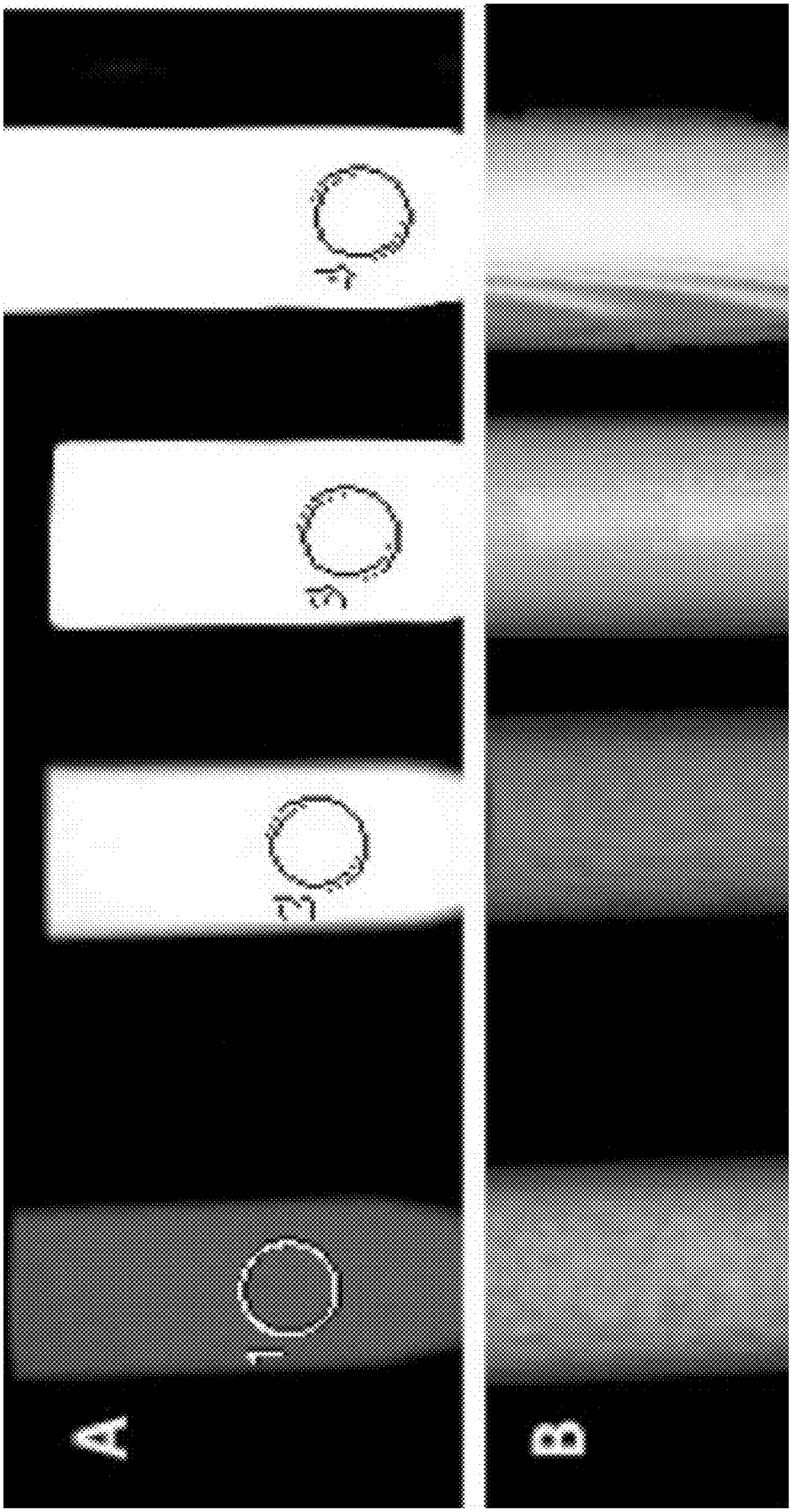
FIG. 2C shows small vials of distilled water and three different concentrations of a HS, confirming discernable contrast and detectability under CT imaging.

Various investigations were performed to assess the degree of heating achievable by the CsCl heat substrate compounded with different salt concentrations. FIG. 2A specifically shows that the heat substrate picks up microwave energy in a distance to augment heating, with high CsCl concentration of 100 mg/ml greatly increases heating measured near to (1 mm) the antenna, and that enhance heating with high uniformity is attained with other concentrations measured 15 mm away from the antenna (FIG. 2B). The Figures specifically illustrate the effect of heat substrate (100 mg/mL, CsCl/20% (w/v) polymer) on temperature increase by microwave energy (15 W, 915 MHz, t=400 sec) in FIG. 2A, where the temperature increase was monitored 1 mm away from the antenna; and the effect of heat substrate (0, 100, 250 mg/mL, CsCl/20% (w/v) polymer) on temperature increase by microwave energy (60 W, 915 MHz, t=600 sec) where heat substrate is deposited 15 mm from the MW antenna. There is a significant augmentation of heat when the heat substrate is present. Moreover, the salt/polymer heat substrate is an excellent contrast agent visible through CT as shown in FIG. 2C. In that Figure fixed volumes of different concentrations of the salt preparation and of distilled water were imaged under CT and their Hounsfield absorbance noted to be: 1. Distilled water −15 Hu, 2. HS (10 mg/mL) 286 Hu, 3. HS (100 mg/mL) 2056 Hu, 4. HS (1000 mg/mL) 3070 Hu. The lower portion of FIG. 2C shows the same samples with computer-aided enhancement. Even the lowest concentration 10 mg/mL HS yields a discernable contrast comparing to water in CT. The imaging was performed using a GE Optima 580 W CT scanner with CT protocol: 120 kV, 50 mA, 0.8 second rotation, 0.562:1 pitch, and 16×0.625 mm detector configuration. The radiation output (CTDIvol) was 12.08 mGy, and the Dose Length Product was 193.88 mGy-cm.

Figure 2D:
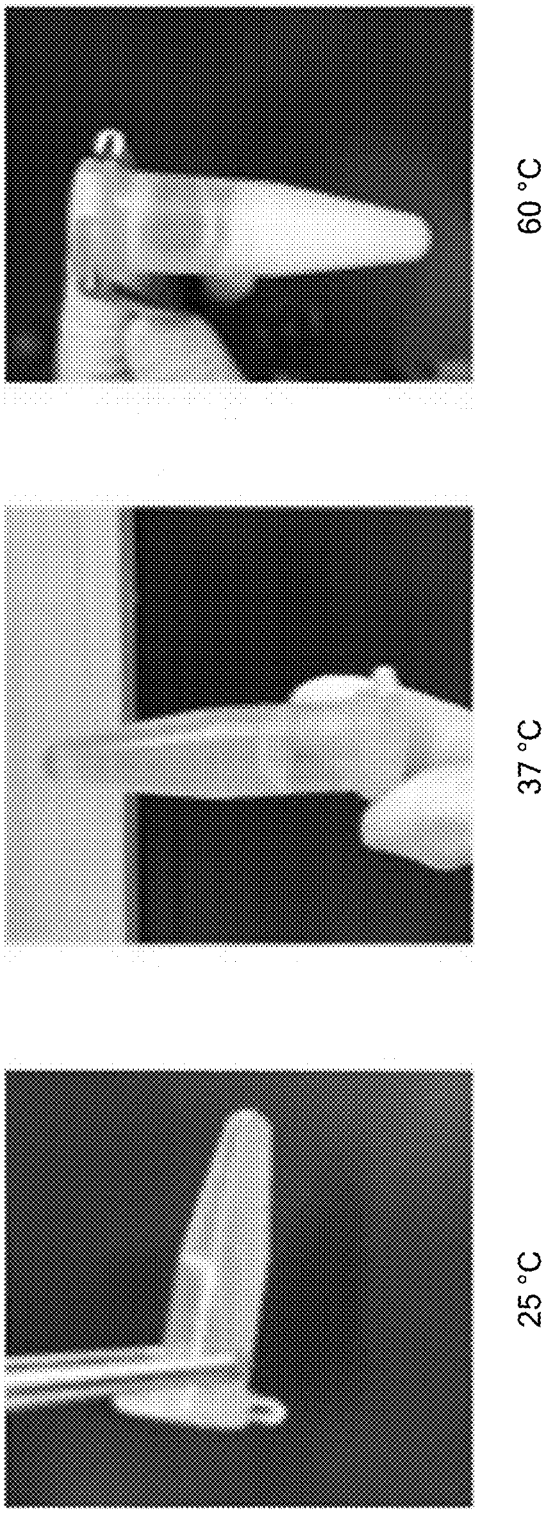
FIG. 2D shows a polymer/salt agent undergo liquid-gel-precipitate changes with temperature rise.

FIG. 2D illustrates the phase change properties with increasing temperature when the CsCl salt is compounded with polymer.

Temperature-time plots were made for different concentrations, together with pictures of the substrate changes when deposited and microwaved in an ex-vivo liver and these confirmed that the heat substrate is capable of heating liver tissue 15 mm away from the antenna, and that the substrate can be deposited as a liquid at ambient temperature and turns into a gel once in body, allowing the tumor boundary to be precisely targeted to ensure complete ablation. In that study a whole calf liver was heated with MW energy (60 W, 915 MHz): and a small 350 μL volume of 100 mg HS in 20% (w/v) polymer solution was injected to a point 1.5 cm away from the tip of the MW antenna. After 10 minutes, the area was cut open to observe the polymer solution transformed into a precipitate. The temperature increase was seen to be proportional to the HS concentration. At 250 mg/mL, the temperature reached 60° C. within 3 minutes. At 100 mg/mL, it took approximately 5 minutes whereas the temperature increase was nominal when no HS had been applied.

The investigations of Example 1 thus demonstrated the value of the heat substrate. Further investigations were designed and/or carried out to model or assess heating characteristics of the compositions in specific tumor tissues or specific distances, as well as evaluating imageability of representative formulations (see the discussion of FIG. 2C, supra) to better support use of the heat substrate in clinical procedures and new methods of treatment. Specifically, the heat substrate may be suitably positioned in relation to the microwave antenna, so that application of microwave energy produces a tailored heating profile to heat up and ablate the surrounding tissue. For example, the accelerant may be positioned somewhat away from the antenna to enhance heating of peripheral tissue which is too distant to be fully or uniformly ablated using a single microwave antenna alone. The thermal accelerant can also be positioned to prevent the heat loss (also known as "heat sink" see FIG. 1C—that would otherwise occur due to the presence of a large blood vessel in or adjacent to the intended ablation zone, trapping an effective level of heating in the near field without ablating the blood vessel itself. Modeling was performed for the use of multiple antennae, and for more than one localized body of thermal accelerant strategically placed to define a larger, or more uniform and expanded ablation zone, or to define an ablation zone while limiting the time that power is applied to other portions of the organ. Thus the thermal accelerant plays a cooperative and synergistic role in augmenting the effective microwave energy. The suitability for each of these interventions, however, will require that the actual level of increased heating be sufficient to overcome any countervailing conduction and absorption effects exerted by surrounding tissue.

A pilot study was designed to establish the actual thermal accelerant response as a function of microwave conditions (i.e., power, frequency, ablation period and distance) in pig's liver. Ideally, the thermal accelerant augments the microwave energy transmitted through the antenna, and it was expected that the thermal accelerant turns into a gel, once injected, in the target area of the body. Upon application of the microwave energy, the thermal accelerant will heat up the surrounding tissue, which is too distant to be ablated with single microwave antenna alone.

Figure 3A:
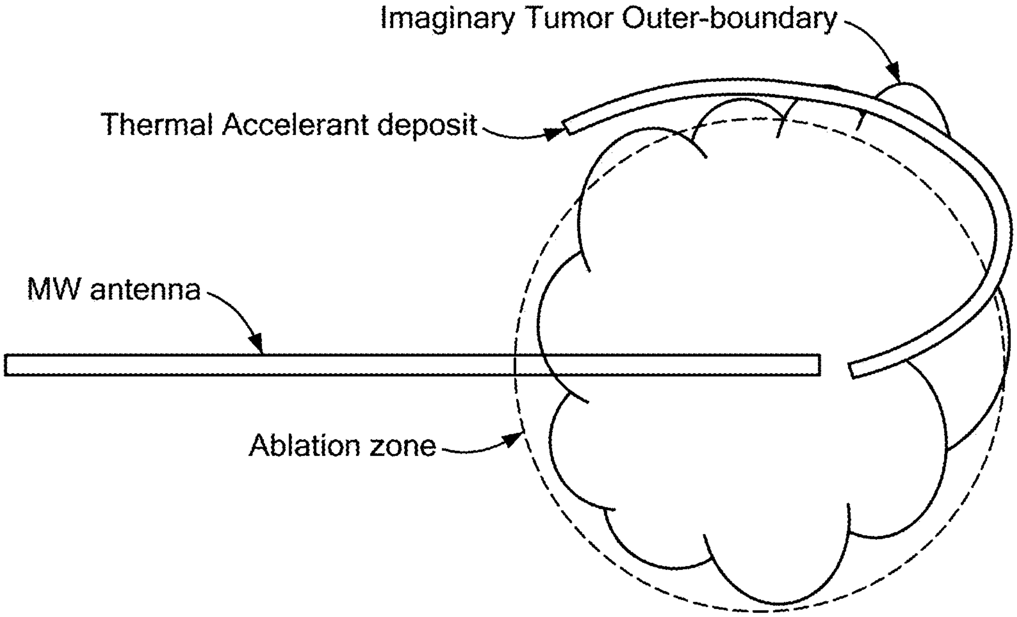
FIG. 3A schematically shows a tumor and placement of antenna and thermal accelerant.
Figure 3B:
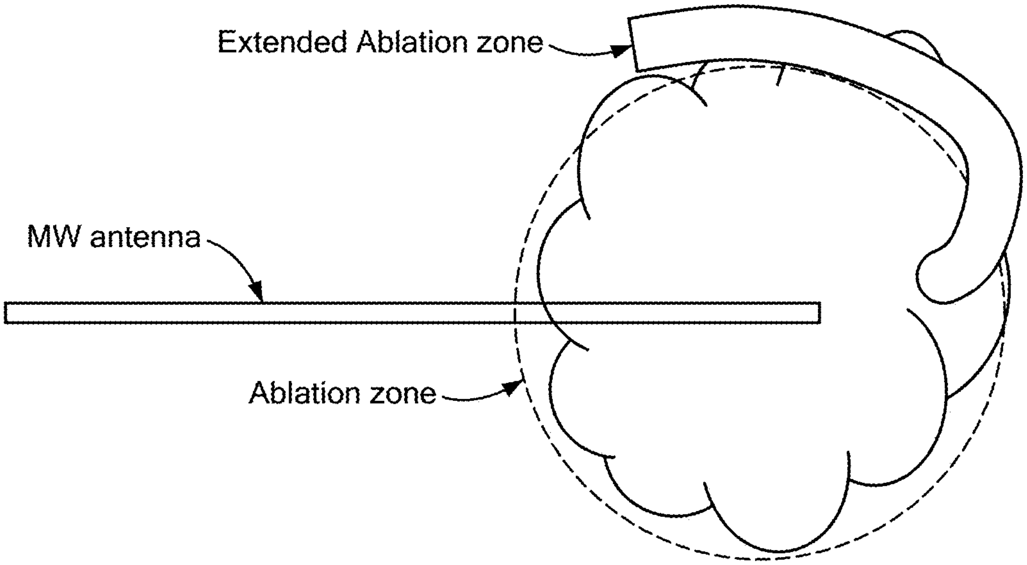
FIG. 3B shows extension of ablation with the placement of FIG. 3A.
Figure 4:
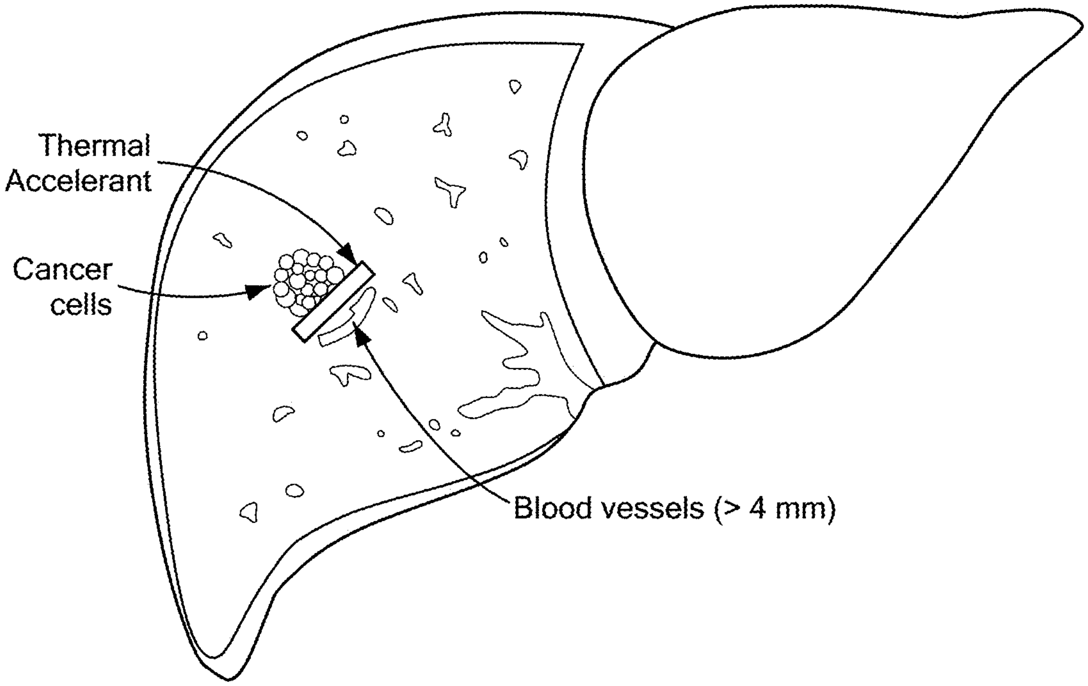
FIG. 4 shows a liver section and placement of thermal accelerant between a tumor and a blood vessel.
Figure 5:
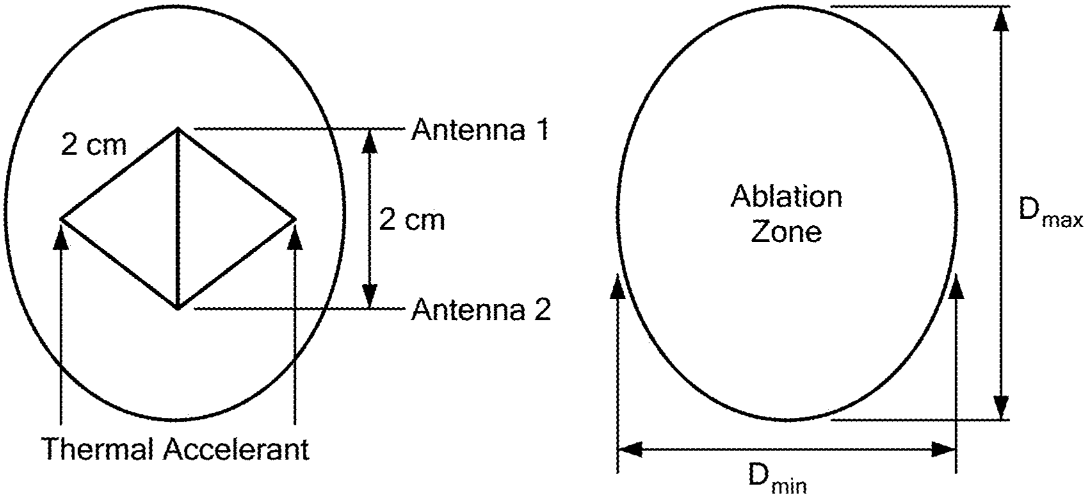
FIG. 5 shows placement of two antennas and two sites of thermal accelerant for creating an enlarged ablation zone.

This situation is illustrated schematically in FIG. 3A and FIG. 3B wherein a small mass of the substrate located at the upper right distal region or surface of an irregular tumor (FIG. 3A) and outside of a theoretical circular or symmetric effective ablation zone centered on the microwave antenna, produces a well-defined ablation region (thick band, as seen in FIG. 3B), extending the region of complete ablation to or beyond the tumor boundary. The study was further designed to test the notion that the thermal accelerant can help avoid the heat loss (also known as "heat sink") caused by a blood vessel adjacent to the ablation zone, without ablating the blood vessel itself. This situation is illustrated in FIG. 4, which identifies where to place the thermal accelerant to enhance tumor ablation while avoiding damage to the vessel. FIG. 5 illustrates placement of thermal accelerant and multiple microwave antennas to create a wider and taller ablation region of uniform intensity, showing that if multiple antennae and thermal accelerant are strategically placed, the ablation zone can be expanded. This is to demonstrate a cooperative and synergistic role that the thermal accelerant (TA) plays in augmenting the heating by microwave energy.

FIGS. 3A and 3B schematically diagram the microwave ablation, wherein a thermal accelerant is injected to an imaginary tumor target area. A typical ablation zone is about 2.5 cm in diameter when a single antenna is used with the microwave ablation conditions: 915 MHz, 60 W for 10 minutes. The thermal accelerant, due to its viscous composition, remains relatively stationary at a target site once deposited since it turns to a gel at body temperature. The track of the thermal accelerant gel is shown just outside of the nominal ablation zone, and runs through the outer-boundary of the imaginary tumor in the liver. FIG. 3B shows the coagulative ablation zone extended by augmentation of the microwave energy.

FIG. 4 shows an experimental set-up wherein the thermal accelerant deposited between a major blood vessel (>4 mm in diameter) and the ablation zone to see if the heat loss will be minimized. Because the microwave energy is augmented between the antenna and the thermal accelerant, shorter antenna actuation can achieve complete ablation of the tumor, and the blood vessel itself will be protected from being ablated.

FIG. 5 shows multiple antennae and bodies of thermal accelerant strategically placed to maximize an ablation zone. When two antennae are placed 2 cm apart (d=2 cm) and the two thermal accelerants are placed 2 cm from each antenna to form a rhombus (in cross-sectional view), application of the microwave energy (illustratively total 120 W, 60 W each antenna) for 10 minutes will result in the larger ablation zone than control (d=2 cm, MW only) and a known case of d=1.5 cm (i.e., 915 MHz, 60 W each, 10 minutes, Dmax=3.5 cm, and Dmin=3.3 cm). This demonstrates a cooperative and synergistic role of TA in augmentation of the microwave energy.

A brief discussion of the Thermal Accelerant and the underlying technical considerations may be useful for understanding the scope of materials and effects of the disclosures and improvements in microwave ablation technology.

The novel MWA methodology is intended to achieve the complete ablation of tumors. The methodology utilizes a thermal accelerant which in one embodiment is comprised of cesium chloride (CsCl) and a reverse phase transition polymer with the following rationale: Tissue ablation by MW energy primarily operates by kinetically exciting water molecules to generate heat. A water molecule is structurally bent (104.5° C.) due to two non-bonding electrons on oxygen atom, and thus has a relatively high dipole moment (1.85 D, D=Debye). At the MW frequency region (300 MHz-30 GHz), water molecules synchronize to the alternating electrical field to cause collisions among themselves, and this energy is converted into heat. Most of alkali and alkaline earth metal ions tend to have high dipole moments (D>7-8, e.g., KBr 10.4 D, BaO 7.9 D), suggesting that these compounds can generate heat more effectively than water molecules. Among these ionic compounds, cesium chloride (CsCl) is particularly interesting not only because of its high dipole moment (10.4 D), but because of its unique physicochemical and toxicological properties that it offers for MW ablation: First, CsCl is highly soluble in water (1,865 kg/L at 20° C. and 2.7 kg/L at 100° C.). This means that a highly concentrated CsCl thermal accelerant solution can be made if necessary; second, with its high atomic number and density (Z=55 and d=3.99 g/mL), the Cs ion can provide an excellent contrast in CT. This is particularly useful for our purpose since CsCl can be used as a substrate for image-guidance; thirdly, CsCl is non-toxic (LD50=2,600 mg/kg, oral, 910 mg/kg iv, rat). The polymer component possesses the unique property of being a liquid at ambient temperature, but a gel at typical body temperature (35-37° C.). Moreover, upon a further increase in temperature, the polymer precipitates by expelling water molecules from the polymeric lattice structure. The polymer is considered safe, and consists of polyethylene glycol (PEG) that is esterified by a FDA approved poly-(lactic-co-glycolic) acid (PLGA) on both ends. The polymer is biodegradable and biocompatible. CsCl is an ionic compound and, thus, miscible with the aqueous polymer solution to give homogeneous distribution of CsCl permitting uniform heating within the target ablation space. In response to the delivery of microwave energy, CsCl tumbles synchronously to the alternating electric field fueled by its intrinsic dipole moment to generate heat.

Using CT for image guidance, the desired amount of the thermal accelerant with known CsCl concentration can be deposited in the boundary of the tumor mass. Subsequently, the injected heat substrate turns into a gel of predetermined ablation shape and volume. The heat substrate gel will be heated by MW energy transmitted through an MW antenna (MicrothermX® Perseon Medical, Salt Lake City, Utah) to reach tumoricidal temperature (>60° C.) in the targeted area.

Example 2

Preliminary Study: Augmentation of Microwave Energy

Figure 6A:
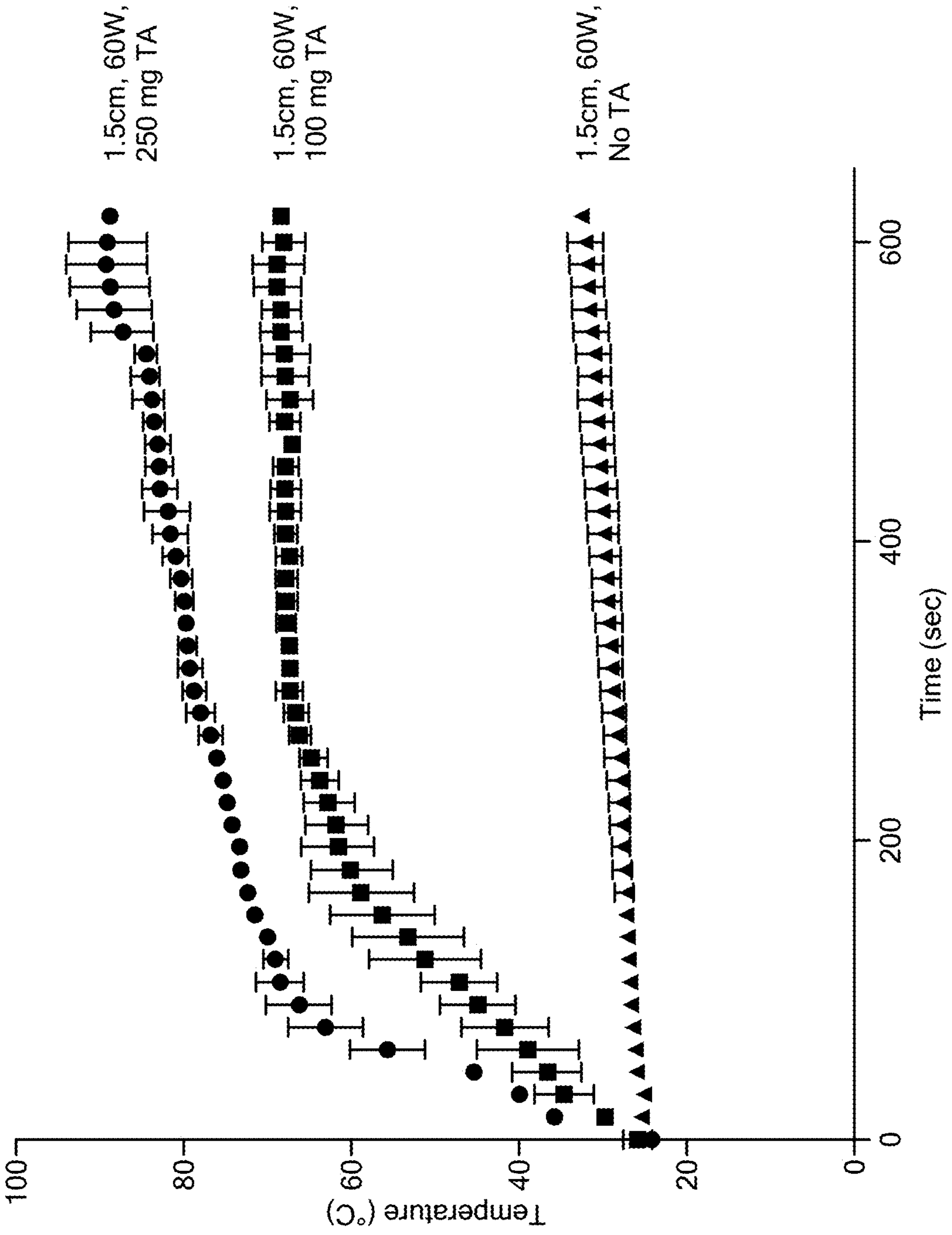
FIG. 6A shows an experimental setup used to evaluate heat augmentation of a thermal accelerant.
Figure 6B:
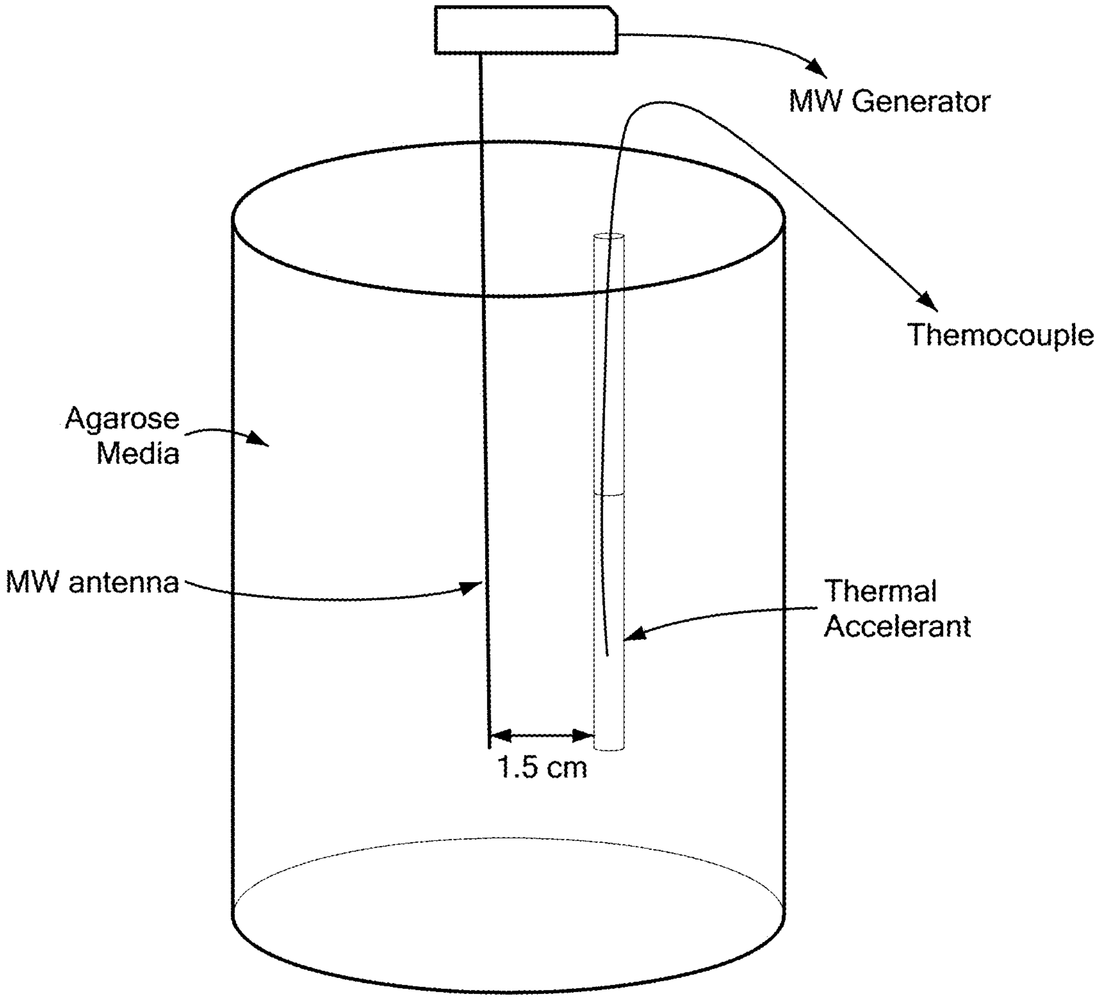
FIG. 6B is a Time/Temperature chart of heating for different amounts of the accelerant.

As a proof of concept, we tested the efficiency of the heat substrate in augmenting the microwave energy. Using a phantom (1% (w/v) agarose medium), temperature increase by a control and the heat substrate (two concentrations: 100 mg/mL and 250 mg/mL, respectively) was measured over time. Under the MW conditions (60 W, 915 MHz, 10 minutes), a maximum ablation zone attained is typically 2.5 cm in diameter (i.e., a zone extending a distance 1.25 cm from the antenna). This distance and the conditions were used as a baseline platform to evaluate the augmentation efficiency of the heat substrate. As depicted in FIG. 6B the heat substrate was placed at 1.5 cm from the antenna, and was heated by MW energy transferred through an MW antenna (MicrothermX® Perseon Medical, Salt Lake City, Utah) to reach tumoricidal temperature (>60° C.). Temperature plots are shown in FIG. 6A. The thermal accelerant was found to augment the MW energy in a concentration dependent manner and reached beyond 60° C. within 5 minutes (c. 1 minute 250 mg/mL; <3 minutes 100 mg/mL, respectively) in comparison to the sample without the thermal accelerant. FIG. 6A shows a typical set up for the in vitro experiment.

Example 3

A preliminary study of the thermal accelerant as a CT contrast agent was carried out. Various concentrations of the thermal accelerant (TA) solutions were prepared and measured for their CT contrast. FIG. 2C shows the TA solution with the concentration as low as 10 mg/mL produced a discernable contrast as compared to water. The degree of the CT contrast was found to be proportional to the concentration of the thermal accelerant (TA), so the TA solution is CT visible. The upper portion of FIG. 2C shows four samples 1)-4) as follows: 1. Distilled water −15 Hu, 2. TA (10 mg/mL) 286 Hu, 3. TA (100 mg/mL) 2056 Hu, 4. TA (1000 mg/mL) 3070 Hu. The lower portion of FIG. 2C shows the same samples with computer-aided enhancement. The lowest concentration 10 mg/mL TA yields a discernible contrast compared to water in CT. GE Optima 580 W CT scanner. Used CT protocol: 120 kV, 50 mA, 0.8 second rotation, 0.562:1 pitch, and 16.times.625 mm detector configuration. Radiation output (CTDIvol) was 12.08 mGy. Dose Length Product was 193.88 mGy-cm.

Example 4

Reverse Phase Transition Polymer.

The polymer used with the thermal accelerant desirably has the property of being a liquid at ambient temperature, but a gel at typical body temperature (35-37° C.), which, in some embodiments, can allow the gel to remain stationary at a target site once deposited. Upon a further increase in temperature, the polymer precipitates by expelling water molecules from the polymeric lattice structure as shown in FIG. 2D supra. The polymer of this example is technically a block-co-polymer that is made of poly(lactic-co-glycolic acid) (PLGA) and polyethyleneglycol (PEG). PLGA is a FDA approved polymer for its biocompatibility like PEG. The polymer used as a heat substrate component here is structurally arranged as follows: PLGA-PEG-PLGA. At ambient temperature (25° C.), the polymer is conformed in such a way that a PLGA interacts with the intramolecular PLGA to form a hairpin. This conformation will change as the temperature increases so that intermolecular PLGA-PLGA interactions predominate (37° C.). Upon further heating (>60° C.), the conformation will be changed back to the hairpin conformation except that water molecules are expelled out of the polymer layer at higher temperature.

Example 5

Ex Vivo Experiment Augmentation of MW Heating by the Heat Substrate in a Whole Calf Liver.

A whole calf liver was heated with MW energy 60 W, 915 MHz: A small volume (350 μL) of 100 mg CsCl in 20% (w/v) polymer solution was injected to a point 1.5 cm away from the tip of the MW antenna. After 10 minutes, the area was cut open to observe the polymer solution transformed into a precipitate. The temperature was plotted showing the temperature increase to be proportional to the TA concentration. At 250 mg/mL, the temperature reached 60° C. within 3 minutes. At 100 mg/mL, it took approximately 5 minutes, while without TA the temperature increase was nominal.

Figure 7:
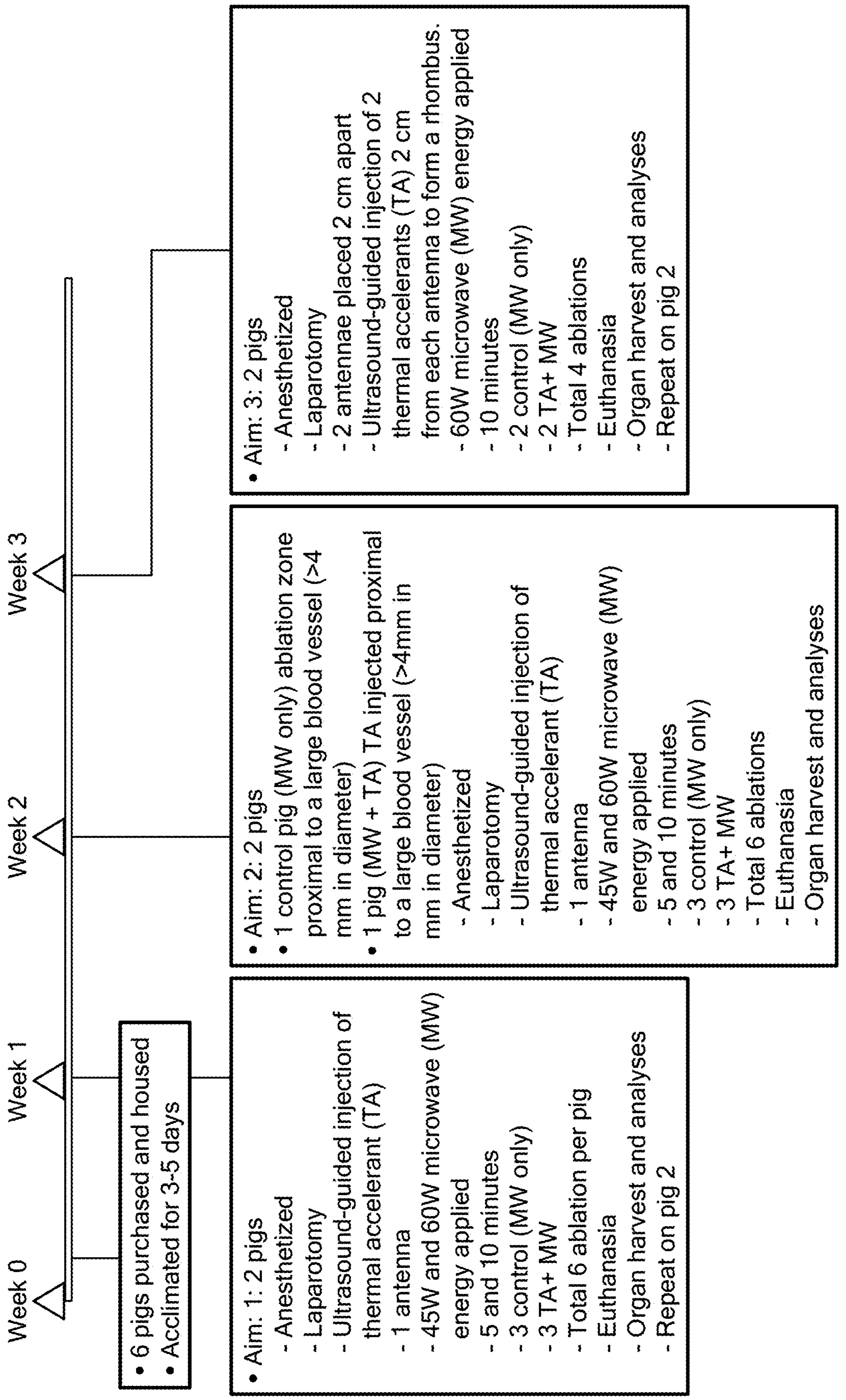
FIG. 7 is a chart of an investigational in vivo animal protocol designed to identify effective ablation materials, parameters and operating procedures.

The foregoing observations and measurements provided substantial confirmation of the underlying concepts, and further motivation to pursue in vivo animal investigations which could identify the magnitudes of any effects due to live-subject tissue conditions, such as perfusion effects or corrections for blood flow in a vessel, and establish variances in ablative results. In such a study ('a pilot study') would have as Specific Aims one or more of the following: Aim 1) Laparotomy will be performed on a pig, and the liver will be exposed. Using ultrasound as image-guidance, the microwave (MW) antenna will be inserted and the microwave energy of the preset parameters will be applied. Similarly, the thermal accelerator (TA, 250 CsCl mg/mL of 20% (w/v) polymer solution) is injected to the liver parenchyma, an imaginary target area using ultrasound as image-guidance and deposited as a stationary gel. The MW antenna will be inserted approximately 1.5 cm away from the thermal accelerant. The microwave energy of the same parameters will be applied to the antenna (i.e., 915 MHz, 45 or 60 W for 5 to 10 minutes). All animals will be euthanized immediately after the procedure, and the liver will be harvested for further comparisons including CT and analysis of the ablation patterns and measurement of the ablation volume; Aim 2) As described in Aim 1), the animals are anesthetized and laparotomized to expose the liver. With ultrasound guidance, the antenna will be placed 1.5 cm from a large blood vessel and ablated with the preset conditions (915 MHz, 45 or 60 W for 5 to 10 minutes) on the first pig (control). In the second pig's liver, the antenna will be placed 1.5 cm from a large blood vessel after the thermal accelerator is injected near the blood vessel, and then the microwave energy is applied. Each pig will receive three ablations: 1) 45 W for 10 minutes, 2) 60 W for 5 minutes, 3) 60 W for 10 minutes. Immediately after the procedure is complete, the pigs are euthanized to harvest the liver for CT and analysis of the ablation patterns and measurement of the ablation volume by depth, height, and width; Aim 3) A pig liver will be exposed after laparotomy is performed on a pig under anesthesia. Using ultrasound as image-guidance, two antennae will be inserted in the liver 2 cm apart and the microwave energy (60 W) will be applied for 10 minutes for control. In the same liver, two antennae will be inserted 2 cm apart, and followed by two injections of the thermal accelerant (TA) by which the injection is made 2 cm away from each antenna to form a rhombic shape as depicted in FIG. 3. The microwave ablation will be performed under the same conditions as control (i.e., 60 W, 10 minutes). After the procedure is complete, the pigs are euthanized to harvest the liver for CT and analysis of the ablation patterns and measurement of the ablation volume by depth, height and width. FIG. 7 is a chart showing a proposed investigative protocol.

Briefly, the Aim 1 is intended to examine heat augmentation efficiency of the thermal accelerant (TA) in percutaneous microwave ablation using a single antenna, while Aim 2 is intended to assess efficacy for overcoming heat sink effects, and Aim 3 investigate the TA being used for situations that may have been addressed previously by using an extra antenna.

As described above, the thermal accelerant was conceived in order to mitigate the incomplete ablation issue, and envisions a novel thermal accelerant (TA) that can augment the microwave energy from a distance unreachable by a single antenna alone. This helps not only extending the ablation zone covering the outer-boundary of a tumor mass but also ablating more rapidly. As clinically shown, more effective and faster microwave ablation helps the procedure be more complete, thus lowering rate of tumor recurrence rate. In addition, TA can be injected strategically near a heat sink so that the heat loss can be prevented.

The TA, for best utility in image-guided thermal ablation to treat tumor, preferably has the following properties: 1) it can augment the electromagnetic radiation energy (e.g., radiofrequency, microwave), especially from a distance unattainable by a single antenna; 2) it is visible under various imaging modalities (e.g., computed tomography (CT), ultrasound or MRI); 3) it is injectable, and is stationary once injected, e.g., due to its viscous composition; and 4) it is non-toxic.

As described above, a synthetic polymer with an alkali rare earth salt (CsCl) has been found useful, however other polymer materials such as albumin, DNA, RNA, or glycoproteins and/or glycopolymers, such as IgA, IgG, IgM, and other immunoglobulins offer similar benefits, and the viscosity properties and other traits of albumin or similar preparation can be further tailored by concentration, salt content and other steps. Generally, the components of the TA may include three, non-toxic components: 1) a polymer (natural or artificial) as a carrier; 2) an ionic component for overall charge and viscosity balance; 3) an imaging component. With the optimal compositions of the three components, TA can be deposited at the target area of the tumor under image-guidance (e.g., US, CT or MRI), and be able to augment the applied energy (e.g., microwave, radiofrequency or electroporation) to better achieve complete ablation. For example, TA comprised of bovine serum albumin (BSA), NaCl and tantalum powder satisfy the aforementioned criteria, to provide more effective ablation resulting in elimination of untreated outer-boundary of tumors and the heat sink effect. The salt adjusts the charge distribution within the albumin, while tantalum enhances its imaging characteristics. For magnetic resonance imaging the preparation demonstrates signal decay rate time constants ($T_1$) shorter than many tissues. As an example, liver at 3 Tesla has $T_1$ of approximately 800 ms. The albumin/NaCl preparation has $T_1$ in the range of 250 ms to 330 ms, depending on the concentration of NaCl. In a $T_1$-weighted MRI scan for image guidance, the TA will show substantially brighter than surrounding tissue (positive contrast) allowing for unambiguous positioning of the material. $T_2$ contrast mechanisms can also be used, primarily via negative contrast in which the TA has shorter $T_2$ than surrounding tissue and $T_2$-weighted scans are used for guidance.

Albumin is the most abundant protein in human blood with a concentration of approx. 40 mg/mL, and a molecular weight of 67 kDa, being produced in the liver with about 13-14 grams per day entering the circulation system. Albumins belong to a globular protein family, which are water-soluble, moderately soluble in concentrated salt solutions, and experience heat denaturation. Albumins are commonly found in blood plasma and differ from other blood proteins in that they are not glycosylated. A number of blood transport proteins are evolutionarily related, including serum albumin, alpha-fetoprotein, vitamin D-binding protein and afamin. Serum albumin is the most abundant of human blood plasma. It binds water, cations (e.g., $Ca^{2+}$, $Na^+$ and $K^+$), fatty acids, hormones, bilirubin, thyroxine and pharmaceuticals (including barbiturates and taxol). Its main function is to regulate the colloidal osmotic pressure of blood. The isoelectric point of albumin is 4.9 (of human serum albumin, Ip=4.7).

Albumin is comprised of 3 domains of similar structure, which all originated from the same domain. Each domain is composed of ten α-helices and can be further divided into two subdomains, denoted as A and B, containing 6 and 4 helices, respectively. The two subdomains are connected by a long amino acid loop, which is responsible for the change in orientation of the subdomains. Its seven fatty acid binding sites are distributed asymmetrically across the protein. Additional sites of importance in binding include the free thiol located at the cysteine-34 amino acid residue and Sudlow's sites I and II, which bind a variety of nonspecific hydrophobic drugs.

On the other hand, the conformational flexibility between domains depends on the bending of the helices. Its canonical structure is supported by a conserved set of 17 disulfide bridges, which are maintained in all mammalian serum albumins. Of the 3 domains, the first domain is the only one to contain 5, not 6, disulfide bridges, missing one at Cys-34. Instead, the lack of an intramolecular disulfide bridge forming at Cys-34 allows albumin to dimerize with another albumin molecule at this residue. HSA, BSA, LSA, and ESA have exchanged 70-85% of their residues over the course of 500 million years, however the positions of the cysteines and disulfide bridges have not changed. Additionally, although the domains have undergone significant evolutionary changes, their overall architecture and secondary structure elements have remained unchanged.

Albumin enters into tissue from blood vessels via transcytosis initiated by binding to GP-60, an endothelium surface receptor expressed on the vascular endothelium or alveolar epithelium. The cluster of GP-60 and albumin is internalized as a vesicle by association with Cav-1. The transcytosis is completed by transporting to and fusing with the basolateral membrane, on the opposite side of the endothelial cell membrane. When the albumin molecule is old, damaged, or structurally compromised, GP-18 and GP-30 receptors are used for lysosomal degradation. Ultimately, the albumin molecules end up in the liver to complete the degradation process, while healthy albumin returns to the blood vessels via the lymphatic system through a natural recycling process.

In some embodiments, albumin can be systemically distributed throughout the body via intravenous injection. After albumin enters the body, albumin travels to the target site, e.g., the tumor, by either passive accumulation of albumin or active internalization and trafficking. The passive accumulation utilizes the tumor vasculature leakiness, paired with poorly formed lymphatic drainage, a phenomenon known as the enhanced permeability and retention effect (EPR). The internalization and trafficking of albumin by the tumor cells is observed by a mechanism in which cancer cells support their increased metabolic and growth demand by active uptake of extracellular proteins through micropinocytosis. For example, cancer cells expressing oncogenic Ras, an inner plasma membrane protein whose aberrant activation is associated with virtually all aspects of the malignant cancer phenotype, more highly utilize extracellular proteins as a source of amino acids to drive cellular growth As shown in the above-described examples, microwave ablation with the TA can produce significantly larger ablation volumes than that of the control in porcine liver, lung, kidney, and muscle. In some embodiments, the TA can be controlled to "switch-off" at specific temperatures during ablation to control the ablated volume. As the main component of the Thermal Accelerant (TA), a water-soluble protein (e.g., albumin) can be used in the ambient and physiological temperature range. The protein component can be coagulated as temperature increases at which the ability to augment the energy of TA ceases since the conformation of the protein is altered. The coagulation temperature is pH-dependent, i.e., low pH shifts the coagulation (denaturation) temperature of albumin from 62° C. (at pH 7.4) to 46° C. (at pH 3.5). Such ability to control the TA can allow for protection from collateral injury of important tissues or organs during ablation. While it will be appreciated that the temperature at which the TA switches off can be varied, though some non-limiting examples of such temperatures can be >60° C., >80° C., >100° C., and so forth in optimized formulations, in some embodiments, temperatures of up to 170° C. can be observed under in vitro conditions during microwave ablations under the following conditions: 915 MHz, 60 W for 10 minutes at 1.5 cm from the antenna. For example, under these ablation conditions, e.g., 915 MHz, 60 W, 10 minutes, using an (2 mL) injection of TA (HeatSYNC Gel) 1.5 cm from the antenna, using the Perseon MW system (Perseon Medical, Salt Lake City, Utah), ablation volumes that were larger than ablations without TA were produced for each of the four tissue types, with superior reproducibility, as demonstrated in Table 1, reproduced below.

Hyperthermia therapy (or hyperthermia, or thermotherapy) is a type of medical treatment in which body tissue is exposed to temperatures in the region of 40-45° C. (104-113° F.). Hyperthermia is usually applied as an adjuvant to radiotherapy or chemotherapy, to which it works as a sensitizer to treat cancer. Hyperthermia is often categorized as low, medium, and high. Hyperthermia usually uses higher temperatures than tissue diathermy and lower temperatures than ablation, although "high temperature" hyperthermia is often considered thermal ablation. There is no consensus in hyperthermia therapy on the safest or most effective target temperature for the whole body. During most treatments, the body temperature reaches a level between 39.5 and 40.5° C. (103.1 and 104.9° F.). However, other researchers define hyperthermia between 41.8-42° C. (107.2-107.6° F.) (Europe, USA) to near 43-44° C. (109-111° F.) (Japan, Russia). There are many techniques by which heat may be delivered. Some of the most common involve the use of focused ultrasound (FUS or HIFU), RF sources, infrared sauna, microwave heating, induction heating, magnetic hyperthermia, infusion of warmed liquids, or direct application of heat such as through sitting in a hot room or wrapping a patient in hot blankets.

Thermal ablation of focal tumors uses high-temperature tissue heating (>50° C.) surrounding applicators placed at the center of a tumor. Cellular homeostatic mechanisms can accommodate slight increases in temperature (up to 40° C.). Although increased susceptibility to damage by other mechanisms (e.g., radiation or chemotherapy) is seen at hyperthermic temperatures between 420 and 45° C., cell function and tumor growth continues even after prolonged exposure. Irreversible cellular injury occurs when cells are heated to 46° C. for 60 minutes. However, optimal temperatures for ablation exceed 50° C. and may be limited to 100° C. for some applications.

TABLE 1

Table showing ablation conditions and ablation results for different tissue types.

| | Ablation Conditions | | | Ablation Results | | | |
|---|---|---|---|---|---|---|---|
| Tissue | Frequency, power (MHz, W) | Duration of ablation (min) | Distance between antenna and TA (cm) | Types of TA | Ablation Volume with TA ($cm^3$) | Ablation Volume of Control ($cm^3$) | p |
| Liver[4] | 915,60 | 10 | 1.5 | HeatSYNC Gel | 6.80 ± 0.62 | 2.69 ± 0.36 | <0.01 |
| Lung[B, 9,10] | 915,60 | 10 | concentric | HeatSYNC Gel | 4.6 ± 1.9 (PC 5.6 ± 1.8 EP 3.4 ± 0.4) | 1.0 ± 0.9 | <0.01 EB <0.01 |
| Kidney[C] | 915,60 | 10 | 1.5 | BSA-based TA | 12.6 ± 0.97 | 4.69 ± 1.98 | <0.01 |
| Muscle[D] | 2450,100 | 10 | 1.5 | HeatSYNC Gel | 41.9 ± 4.2 | 28.7 ± 10.2 | <0.01 |

Ablation was performed on a plurality of samples of organs (A-D), with each multiple samples being exposed to TA and multiple samples acting as the controls. As shown in Table 1, ablation volumes with TA for certain tissues were, in some instances, almost three times greater than those of the control in which TA was not used.

Figure 8B:
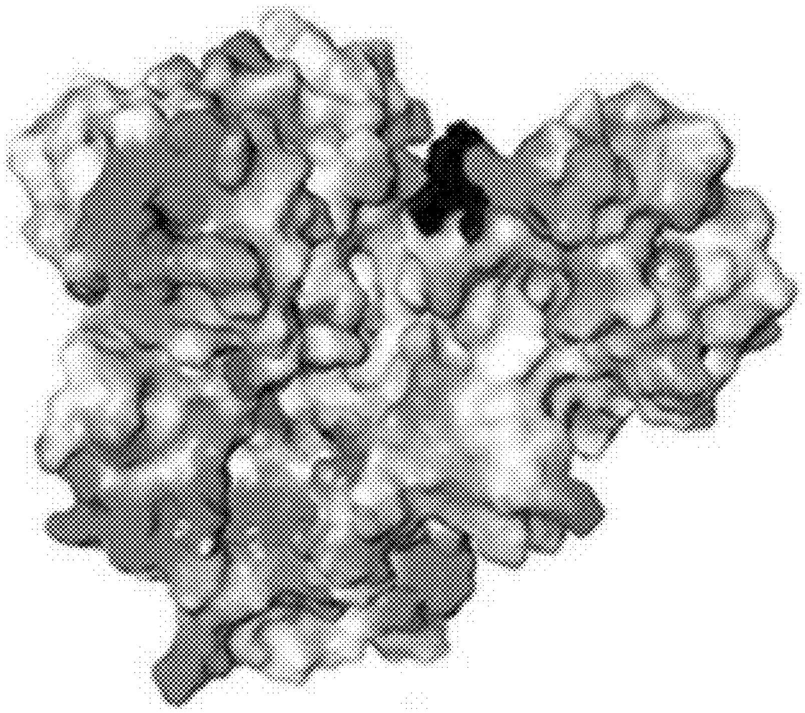
FIGS. 8A and 8B illustrate the surface potential of HSA and of BSA, respectively, with areas of positive and negative charge shaded or colored differently.
Figure 8A:
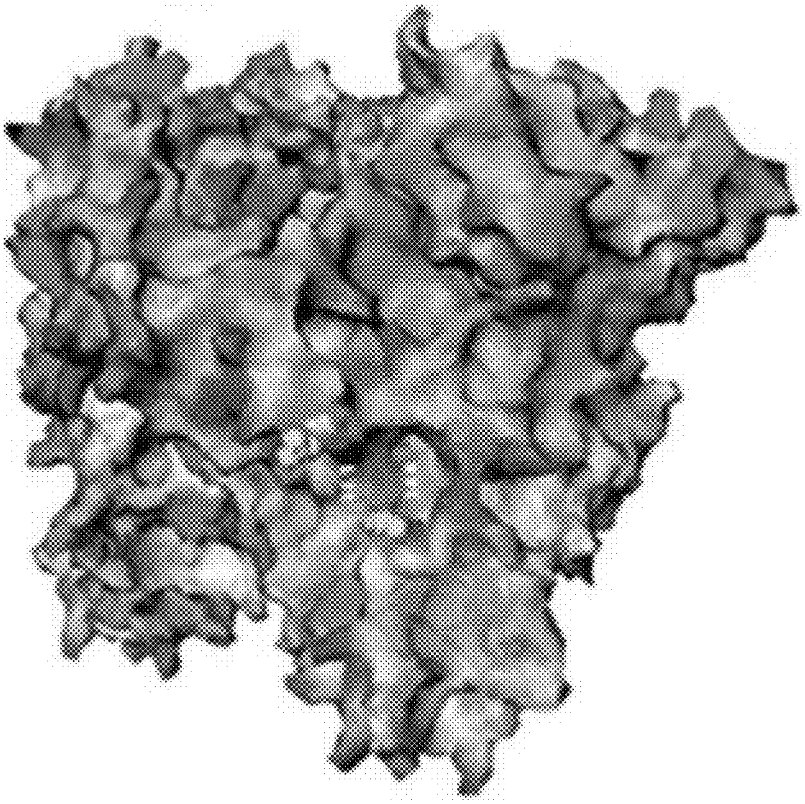

FIG. 8A and FIG. 8B illustrate the surface potential of HSA (A) and BSA (B), with different colors representing positively and negatively charged areas. Vincent Goovaerts et al., Phys. Chem. Chem. Phys., 2013, 15, 18378-18387. Mature BSA contains 583 amino acids and has 99 positive (K, H, R) and negative (D, E) residues. Similarly, mature HSA contains 585 amino acids and has 99 positive (K, H, R) and 98 negative (D, E) residues. Although the general structure of the protein is conserved among mammalian serum albumins, there are significant differences. In sequence, BSA shares only 75.8% homology with HSA. Their structures are canonical (due to the conserved disulfide bridges), but differ in surface amino acids. As a result, the ligand binding pockets in the various serum albumins show different amino acid compositions and slightly different conformations, allowing for the binding of different ligands.

The tantalum component of TA is a high radiopaque material that provides fluoroscopic visualization. Tantalum is an inert metal with a history of use in implants requiring incorporation of a contrast agent, such as arterial stents, hip prostheses, and embolization materials. [9, 10] In addition to its use in embolization materials, tantalum powder has been used as a contrast agent injected into the cervical spinal cord for visualization during percutaneous cordotomy. Additionally, tantalum powder has found uses in neurosurgery, to mark the plane of section in lobotomy or leucotomy, to provide visualization or definition of a site for tumor removal, and for detection of recurrent subdural hematoma after surgery.

Although the properties of serum albumin have been extensively studied under physiological conditions studies on the highly concentrated albumins (i.e., 300 mg/mL), especially, as a carrier of an imaging contrast agent or a thermal accelerant are rare. Nonetheless, calculated dipole moment of serum albumin in vacuum is very large, 710 D (D=Debye) in comparison to the TA substance first-described above, CsCl (ca. 10 D) or compared to water (1.85 D). Despite its large dipole moment, physiologically available bovine serum albumin (BSA) alone does not increase the temperature rapidly due to its low dielectric constant and the loss factor in the range of frequencies of interest, i.e., 915 MHz-2.45 GHz. [12] With 500 mg/mL BSA, a gradual increase to 40-50° C. was observed in vitro at 10 min for 60 W with a 915 MHz when the antenna was positioned a distance of 1.5 cm from the BSA sample. The temperature increase was insufficient to make BSA alone as a TA. It will be appreciated that in some embodiments, the calculated dipole moment of a carrier can be up to, and including, 1,000 D.

Figure 9:
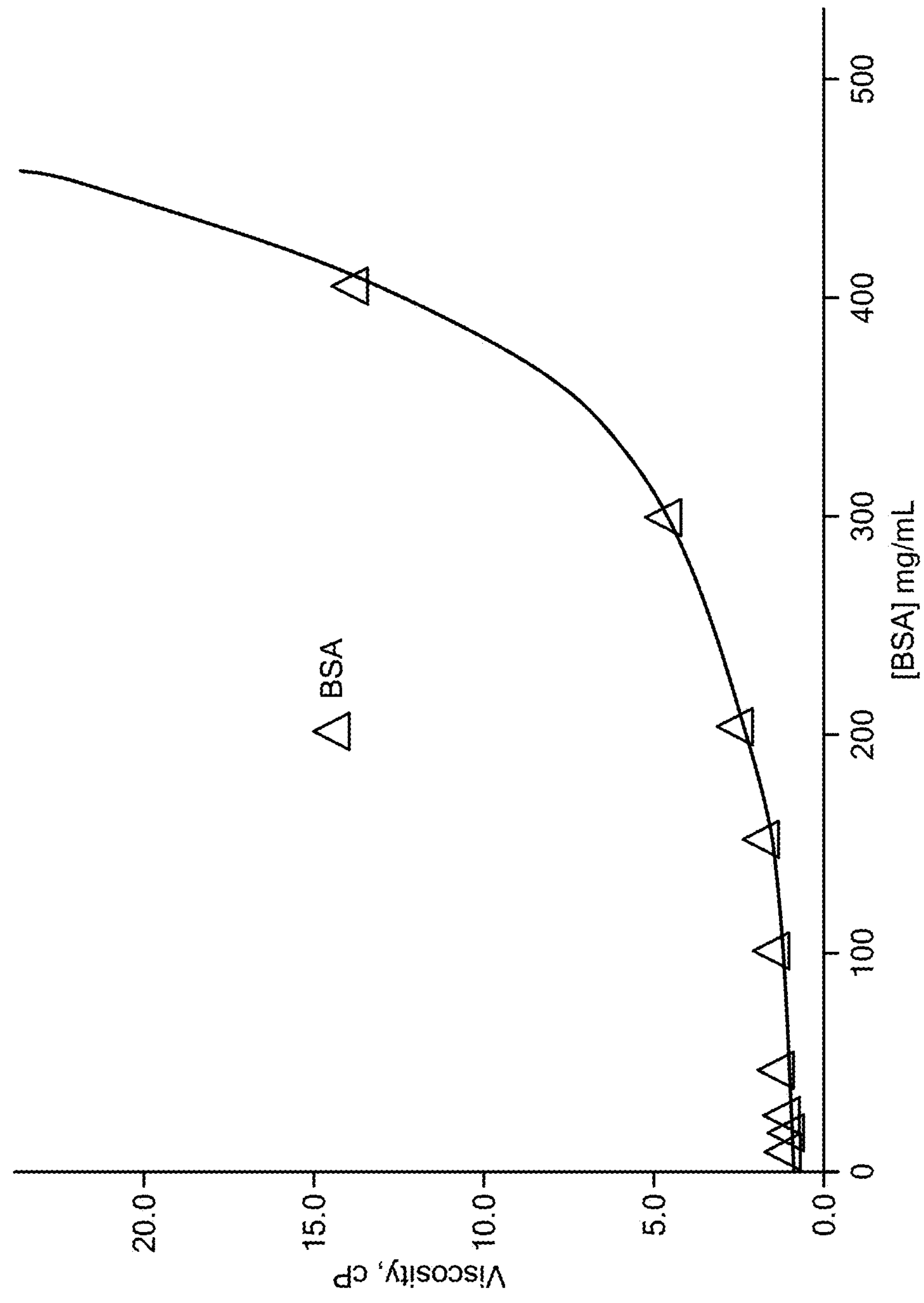
FIG. 9 shows the viscosity of BSA as a function of its concentration in mg/mL.

Furthermore, the albumins of high concentrations (>300 mg/mL) tend to have a very high viscosity due, in most part, to protein-protein interactions as shown in FIG. 9 which schematically illustrates the viscosity of BSA as a function of concentration. For example, in some embodiments the viscosity of the TA can depend on the formulation, but in some embodiments, can range from approximately 50 centiPoise to approximately 25,000 centiPoise. Relative examples of viscosity of compounds are shown in Table 2 below.

TABLE 2

Viscosity of several common compounds.

| Compound | Viscosity (cP) |
|---|---|
| Motor Oil SAE 10 or Corn Syrup | 50-100 |
| Motor Oil SAE 30 or Maple Syrup | 150-200 |
| Motor Oil SAE 40 or Castor Oil | 250-500 |
| Motor Oil SAE 60 or Glycerin | 1,000-2,000 |
| Karo Corn Syrup or Honey | 2,000-3,000 |
| Blackstrap Molasses | 5,000-10,000 |
| Hershey's Chocolate Syrup | 10,000-25,000 |

Materials or formulations with a high dipole moment as potential thermal accelerants can be expressed by the ε" and σ values for thermal ablation (radiofrequency, microwave, irreversible electroporation. A person skilled in the art will recognize that in order to show the capacity of a material, or formulations of a material, quantitatively as a thermal accelerant, the concept of permittivity can be employed in lieu of, or in addition to, evaluation of dipole moment. For example, materials can be tested using an electromagnetic wave of sinusoidal frequency ω, which is directed at a subject sample by an open-ended coaxial cable of a low-power oscillator. Measurement of the magnitude and phase of the fraction of the wave which is reflected allows deduction of the complex permittivity of the tissue. Table 3 illustrates dielectric constant (ε'), loss factor (ε"), and electrical conductivity (σ) of various materials for use in the thermal accelerant at 915 and 2450 MHz.

TABLE 3

Dielectric constant (ε'), loss factor (ε"), and electrical conductivity (σ) of various materials for use in the thermal accelerant at 915 and 2450 MHz

| | 915 (MHz) | | | 2450 (MHz) | | |
|---|---|---|---|---|---|---|
| Material | ε' | ε" | σ | ε' | ε" | σ |
| Water | 78.3 | −0.403 | 0 | 76.9 | −9.23 | 0.1 |
| MeOH | 31.2 | −8.81 | 0.1 | 22.2 | −11.7 | 0.1 |
| 1% NaCl | ~70 | −20 | 1.1 | ~70 | −27 | ~1.5 |
| albumin | 30.7 | −10.2 | 0.52 | 37.9 | −8.20 | 1.12 |
| TA-4 | 40.15 | −93.16 | 4.74 | 32.25 | −50.7 | 5.79 |

The complex permittivity is defined as ε*=ε'−jε", where ε' is the real permittivity and ε" is the imaginary permittivity. Both quantities are dimensionless numbers expressed as a multiple of the permittivity of free space, $\varepsilon_0=8.854\times10^{-12}$ farad/meter. The real permittivity is also known as the dielectric constant. The imaginary permittivity is also called the loss factor and can be written $\varepsilon''=\sigma/(\omega\varepsilon_0)$, so as to incorporate the electrical conductivity of the material, 6. The quantity a directly scales the power deposited per unit volume according to the following expression, $ARD=\sigma|E|^2$, where ARD is Absorption Rate Density (watt $m^{-3}$), 6 is electrical conductivity ($ohm^{-1}$ $m^{-1}$), and JEJ is the magnitude of the electrical field (volt $m^{-1}$) produced by the microwave antenna at the point of interest in the tissue.

As shown in Table 3 above, the electrical conductivity, a, at 915 MHz of one sample (TA-4) equal to 4.74 mho/m with real permittivity (ε', 40.147) and imaginary permittivity (ε", −93.164). Albumin contains (ca. 66 kDa) with roughly 200 ionic residues (100 positive and 100 negative). These residues are arranged in 3-D to have its overall polarity (dipole moment) of approximately 700 D (Debye). However, the key parameters (σ, ε', ε") are similar to those of MeOH due to the protein-protein interaction forces within the solution. In order to break these forces apart, a chaotrope such as NaCl or sodium citrate can be used, as discussed above. For example, sodium citrate can be used as a chaotrope for human serum albumin, though it will be appreciated that, in some embodiments, additional chaotropes can be used. The chaotrope can be used to break apart the protein-protein interactions of molecules to allow the molecules to move more freely to generate more heat. It will be appreciated that while some chaotropes can be ionic so as to be a part of the ionic component of the TA, in some embodiments, the chaotropes can be non-ionic or slightly ionic such that the chaotropes are miscible in aqueous solutions.

The effect of the chaotrope can increase α, and ε" values, as shown in Table 3, values that can be approximately 4.2 times greater than the value for normal saline solution, which is typical of living tissue. This large-scale factor directly expresses the increase in heating rate above that which would be present without the injection of TA into the tumor. That is, electrical conductivity σ and loss factor ε", namely that the loss factor ε" increases with the ionic concentration, which thereby increases tissue conductivity for alternating electrical current in the frequency of radio waves can be used to explain both microwave and radiofrequency ablation. Some non-limiting examples of chaotropes can include L-glycine, L-alanine, L-valine, L-proline, L-serine, L-histidine, L-arginine-HCl, L-histidine-HCl, L-lysine-HCl, L-glutamic sodium, urea, and NaAc.

The values in Table 3 above illustrate the effect of the chaotrope on dielectric properties of various materials. For example, albumin and TA-4 have similar values of real permittivity, 30.7 and 41.15, respectively, while the respective values of loss factor jump from −10.2 to −93.16, which is greater than a nine-fold increase. By way of further example, TA-4 has an even greater increase in the loss factor when compared to methanol, which has a loss factor value of −8.81, which is similar to that of albumin. Methanol and albumin alone are therefore much less effective as thermal accelerants as compared to when a chaotrope is added. Compounds such as albumin tend to be highly concentrated, having little water between ionic components within the albumin molecule. As a result of this high concentration, the distance between albumin molecules is reduced, causing the positive and negative charges between the molecules to interact, which results in restricting mobility of each albumin molecule under oscillating RF or microwave. Adding a chaotrope, such as NaCl, can break apart the protein-protein interactions between the albumin molecules to allow each albumin molecule to freely move, thereby increasing friction and kinetic energy of the molecules causing the molecules to tumble, which is then transformed into heat energy for larger increases in temperature.

It will be appreciated that the effects of chaotropes can be affected by other properties of materials. For example, for 1% NaCl, as described in Table 3 above, addition of the chaotrope can increase the temperature of the 1% NaCl due to its high dipole moment, though the temperature increase will be smaller as compared to albumin due to the smaller size of the NaCl molecule. One skilled in the art will appreciate that the tumbling motion of the larger albumin molecules generate more kinetic energy as compared to the smaller NaCl molecules, which can account for the larger increases in heat of the albumin molecules.

Figure 10A:
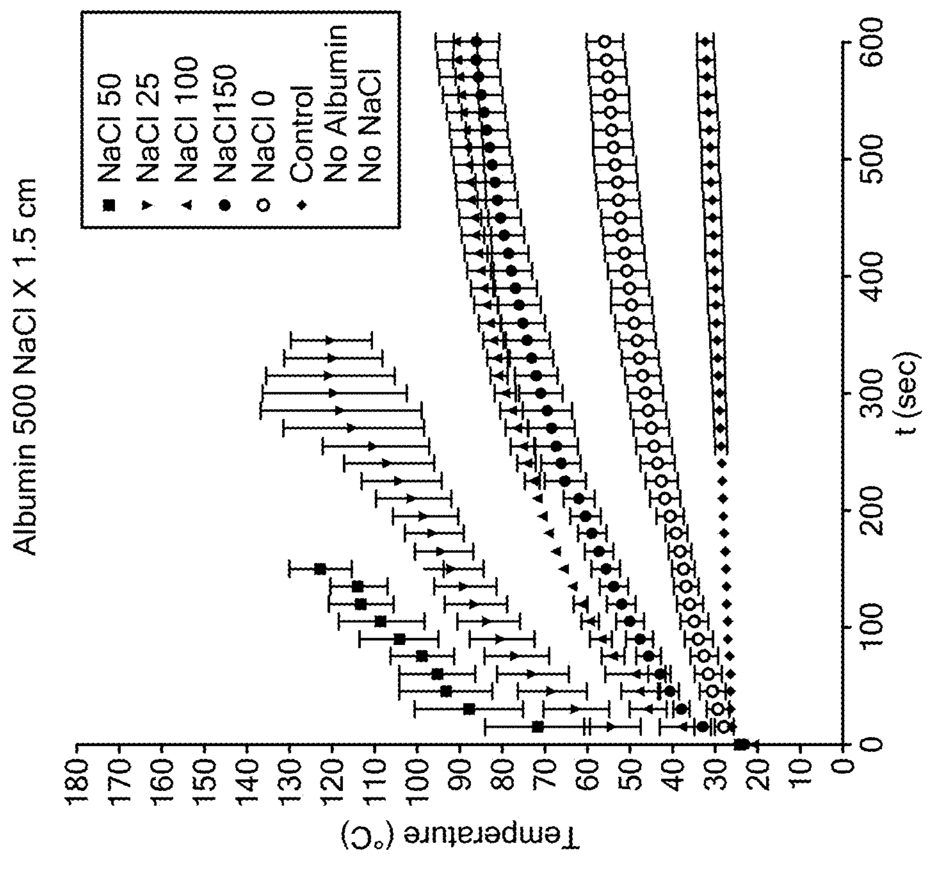
FIG. 10A shows temperature increase over time of a control and of albumin thermal accelerant (TA) having different amounts of NaCl positioned 1.5 cm from a microwave antenna.
Figure 10B:
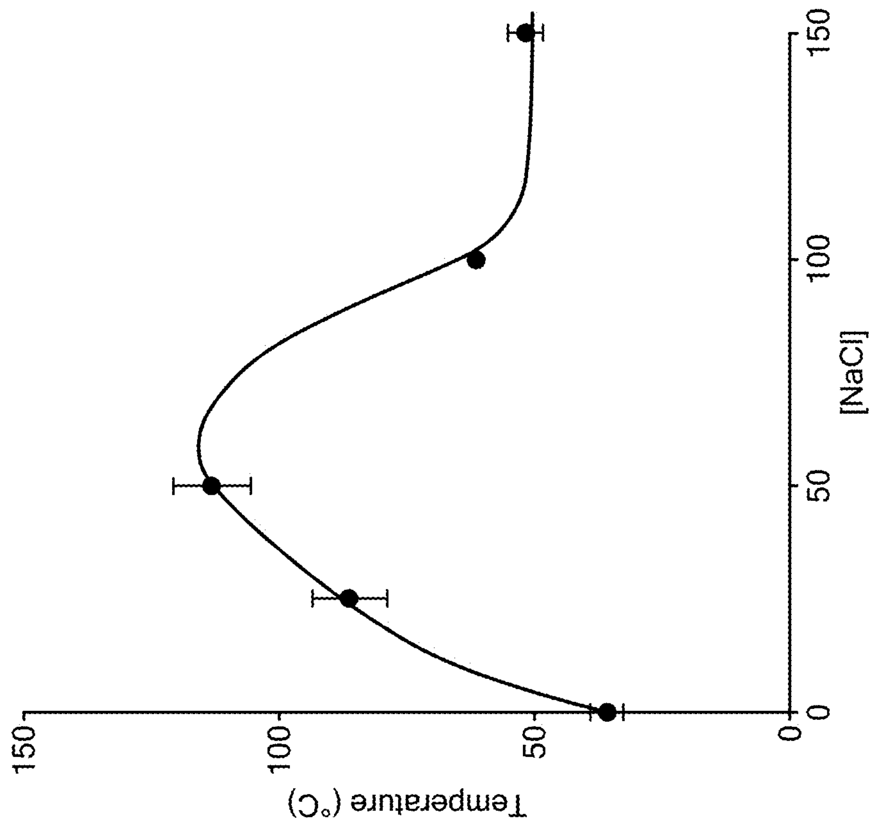
FIG. 10B shows the end-temperature increase at 120 seconds as a function of the NaCl concentration.

Under the applied microwave radiation, the surface charges of the albumin molecule are occupied by the intermolecular interactions with the readily available other albumin molecules. In order to relieve the interactions, we used NaCl as a chaotrope. In essence, it is believed that the intermolecular interactions of BSA molecules consist of charge-charge, dipole-dipole as well as hydrophobic interactions, and thus exhibit high viscosity. By adding NaCl to the solution, the viscosity will be lowered by the salt ions competing with other BSA charges and subsequent solvation by water molecules. This will free up the individual BSA molecules to respond to the microwave energy. We have examined the effect of [NaCl] on thermal acceleration efficiency of the albumin (500 mg/mL), and the results are shown in FIG. 10A. The concentration of NaCl inducing the optimal TA efficiency is slightly higher than 50 mg/mL but less than 75 mg/mL. The higher concentrations suppress the efficiency (>75 mg/mL NaCl), and has a solubility limit beyond 230 mg/mL. FIG. 10A shows the effect of various NaCl concentrations on microwave ablation (MWA, 60 W, 915 MHz, 10 minutes, distance from the antenna=1.5 cm). FIG. 10B is a schematic plot of temperature v. [NaCl] concentration at the 120 second endpoint under the same microwave regimen, showing a temperature peak at around 50 mg/mL NaCl.

Albumin thermal accelerant as described above was used in a number of in vivo microwave ablation experiments in pigs and the ablated sites were stained with triphenyl tetrazolium chloride to distinguish dead from viable cells. The images from these further experiments demonstrated that MWA with TA yields a larger ablation zone than control using a typical microwave ablation (915 MHz, 60 W, 10 minutes d=1.5 cm) without TA as a control. Under the same MWA conditions, TA (1 mL of albumin (500 mg), NaCl (50 mg)) generated a larger ablation zone unaffected by a large blood vessel (1 cm in diameter). A MWA was performed on the left medial lobe of the swine liver (915 MHz, 60 W, 10 minutes d=1.5 cm). Under the same MWA conditions with TA (1 mL of albumin (500 mg), NaCl (50 mg)) generated a larger ablation zone on the same lobe of the liver. A MWA on the left medial lobe of the swine liver (915 MHz, 60 W, 10 minutes, d=1.5 cm) was compared to a MWA with TA (1 mL of albumin (500 mg), NaCl (50 mg) injected behind the blood vessel. For that procedure the ablation zone was seen to extend through the blood vessel (>4 mm in diameter) completely surrounding the blood vessel. In tandem with the previous example, this demonstrated that MWA with TA is able not only able to augment the microwave energy but also to block the heat loss caused by the "heat sink" effect. In an additional experiment, an ultrasound image was taken immediately after ablation was complete (10 minutes), with the blood vessel positioned in between the antenna and TA. During the ablation, blood flow in the vessel was seen to be normal, which indicates that the microwave energy was able to penetrate through the functioning blood vessel and operate effectively in the far field without overheating the vessel. This suggests that the "heat sink" effect can be eliminated by the ablation methodology. Other TTC-treated kidney tissue images show a typical ablation zone using a single antenna with 60 W, 915 MHz, for 10 minutes, and the ablation is slightly off-centered as the connective tissues in the central renal sinus area are less affected. The resultant ablation zone is about 1 cm in diameter. TA was able to produce a drastic increase of the ablation zone (3 cm in diameter) where the central tissues were also shown to be completely ablated (60 W, 915 MHz, 10 minutes; the distance between antenna and TA was 1.3 cm).

Figure 11:
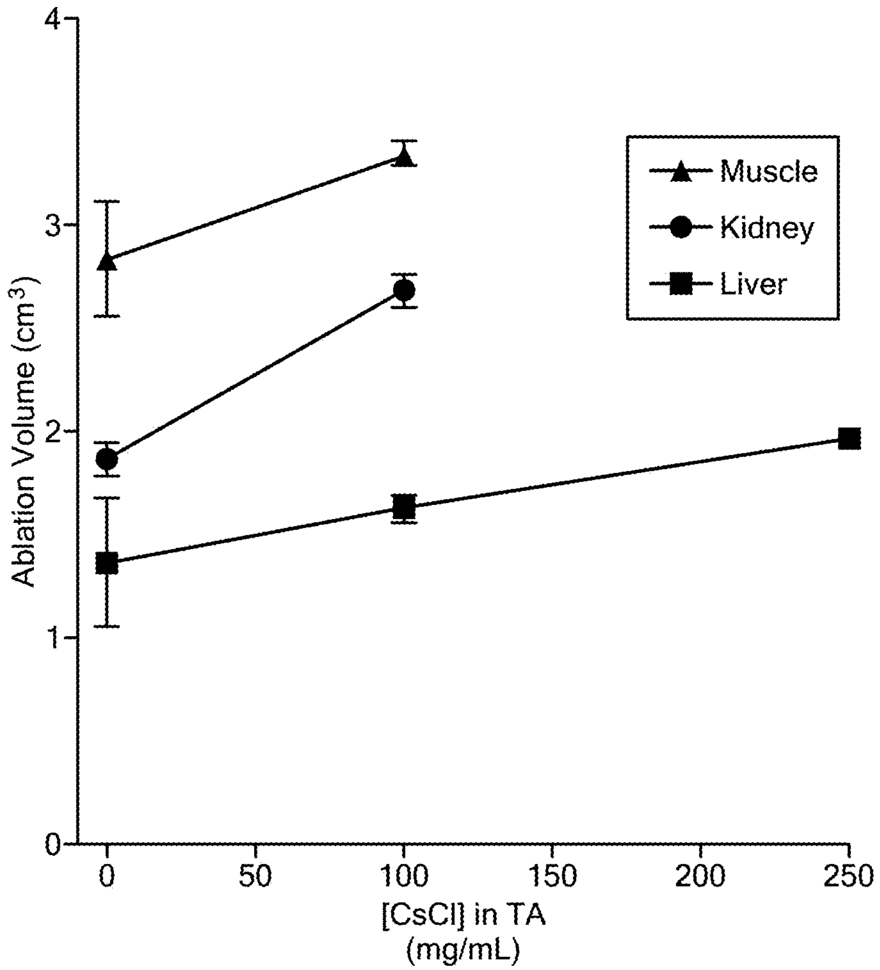
FIG. 11 shows increased ablation volumes achieved in different tissues using different concentrations of a Cesium Chloride component.

FIG. 11 shows the results of further tissue ablation experiments done to assess ablation volumes in cm.sup.3 for 1 mL of the thermal accelerant in different tissues (kidney, muscle and liver) with no TA or 1 mL of the TA at different concentrations of CsCl absorber. In each case the effective ablation zone was greater with the TA. Different concentrations of TA were tested with concentrations up to 250 mg/mL for the liver tissue ablation, as the liver is a key organ for treatment by this method. The other tissues also showed significant ablation volume increases.

As described above, the heat substrate or thermal accelerant of the present disclosure can be implemented in various forms or concoctions, and may involve tailoring the physical characteristics of a natural or artificial polymer to improve their utility as injectable, fixable, imageable and heatable media. Several strong initial materials have been described, but simple testing can quickly reveal or confirm additional ones. Thus, in addition to or in place of the cesium chloride microwave accelerant, other halides such as the bromide or iodide, and other alkaline or alkaline earth cations that are medically useful may be expected to offer similar if not comparable ablation enhancement. For example, Rubidium chloride, or a suitably protected rubidium portion may be useful. Similarly, in addition to BSA and PLGA-PEG-PLGA polymers, materials in alginate media, or salts having anions such as carboxylate or sulfite materials may be employed if they exhibit suitable characteristics, and a discussion of useful cations, anions or electrolyte or other materials for optimizing the desired physical imaging, heating and other characteristics of the thermal accelerant are included above. By way of example, various embolization media can be so modified, and their basic emulsion-like composition will also provide ultrasound imageability. Further, formulation of albumin with sodium chloride salt has been shown to provide a low-viscosity thermal accelerant having appropriate physical characteristics for diverse tissue treatments (including intravascular) with good microwave heating performance, while being completely biocompatible. Different ones of the described thermal accelerants may be appropriate for different microwave regimens of 400 MHz, 915 MHz, 2450 MHz, or 5800 MHz range, and may be used if they are medically safe and result in effective microwave ablation enhancement characteristics for the tissue, tumor mass or organ under consideration.

In addition, the described polymer can be delivered to a vessel in the target tissue and heated to act as an embolization substance to block a vessel that feed the target tumor to thereby cause tumor regression by cutting off oxygen and nutrients supply through the vessel. A further variation is to add one or more anticancer drugs or treatment agents to the polymer, so that once localized and heated the polymer serves as an in-situ time-release treatment agent.

In some embodiments described herein, the ablation methodology includes creating thermal lesions by augmentation of the electric or electromagnetic energy, e.g., absorption of radiated energy and conversion into thermal energy. The ablation methodology includes a thermal accelerant (TA) that functions as a satellite energy absorber to increase the heating effect. The thermal accelerant (TA) is preferably comprised of three components, 1) polymer (natural or artificial) as a carrier; 2) an ionic component or equivalent for overall charge and viscosity balance; 3) an imaging component which allows the ablation procedure to be monitored. However, in embodiments, the carrier may also be an imaging component, including carriers such as human serum albumin and bovine serum albumin.

Other polymers may include either natural or artificial, for example, albumins (e.g., human serum albumin (HSA) and bovine serum albumin (BSA)), silk, wool, chitosan, alginate, pectin, DNA, cellulose, polysialic acids, dendritic polylysine, poly (lactic-co-glycolic) acid (PLGA). The ionic component may include, $M^+X^-$ or $M^{2+}Y^{2-}$, where M belongs to alkaline or alkaline earth metal such as Li, Na, K, Rb, Cs and X represents halogens, acetate and other equivalent counter balance to $M^+$, and Y can be $X_2$ or mixed halogens, acetates, carbonate, sulfate, phosphate and other equivalent counter balance to M.sup.$^{2+}$. Other organic components can independently affect these roles. See: Wang, S. et al, Mol. Pharmaceutics 2015, 12, 4478-4487. For CT imaging, cesium, tantalum, iodixanol (Visipaque), iohexol (Omnipaque), iopamidol (Isovue), iopromide (Ultravist), ioversol (Optiray), ioxilan (Oxilan) ethiodized polymers such as PLGA, PEG, albumin can be utilized. For ultrasound imaging, Definity (perflutren), Optison (perflutren), Definity RT (perflutren), can be utilized and polymers have been found to be in general hypoechoic. However, when PLGA-PEG-PLGA (a block co-polymer, a reverse phase-transition hydrogel) is used, the polymer appears hypoechoic immediately after injection subsequently turns into hyperechoic as temperature increases. For MRI imaging, Gadavist (gadobutrol), Dotarem (gadoterate meglumine), Eovist (gadoxetate disodium), Magnevist (gadopentetate dimeglumine), Vasovist (gadofosveset trisodium), Teslascan (mangafodipir), Prohance (gadoteridol), OptiMARK (gadoversetamide), Omniscan (gadodiamide), Multihance (gadobenate dimeglumine), GastroMARK (ferumoxsil), Feridex (ferumoxides), Clariscan (gadoterate meglumine), Ablavar (gadofosveset trisodium) can be utilized. A similar observation was made when albumin is used as a carrier polymer.

Upon application of electromagnetic energy to drive ablation (e.g., microwave, RF, electroporation), remotely deposited TA can absorb the energy much more effectively than the surroundings and help extend the ablation zone. Remotely deposited TA, here means at a distance greater or equal to 1.5 cm from the antenna open slot, when the conditions (60 W 915 MHz for 10 minutes) are used. As described above, upon application of the electromagnetic energy (e.g., microwave, RF, electroporation) TA deposited adjacent to a large blood vessel can prevent the ablation target from suffering excessive heat loss, therefore TA can mitigate the "heat sink" effect to provide complete ablation. In addition, TA can be used in embolization/ablation combination treatments to destroy tumors. TA has a viscosity similar viscosity to Lipiodol, thus can be delivered via an intravascular catheter to be deposited accurately. A subsequent ablation can destroy tumors effectively.

Thus, as an overview and recapitulation, the thermal accelerant (TA) formulations and materials described above can function as satellite energy absorbers to create thermal lesions by augmenting the coupling of the electric or electromagnetic energy into heat at distances not effectively treatable by an antenna alone. The TA may be comprised of three components, 1) polymer (natural or artificial) as a carrier; 2) an ionic component or equivalent for overall charge and/or viscosity balance; and 3) an imaging component. The polymers may include either natural or artificial, for example, albumins, silk, wool, chitosan, alginate, pectin, DNA, cellulose, polysialic acids, dendritic polylysine, poly (lactic-co-glycolic) acid (PLGA), gellan, polysaccharides and poly-aspartic acid, and combinations thereof. The ionic component may include, $M^+X^-$ or $M^{2+}Y^{2-}$ (as a generalized formula $M^{n+}Y^{n-}$), where M belongs to alkaline or alkaline earth metal such as Li, Na, K, Rb, Cs, and tri sodium, and X represents halides, acetate, and other equivalent counter balance to $M^+$, and Y can be $X_2$ or mixed halides, acetates, carbonate, sulfate, tryptophanate, citrate, phosphate and other equivalent counter balance to $M^{2+}$ as well as formic acid, glycolic acid, lactic acid, octanoic acid, propionic acid, caproic acid, oxalic acid, malic acid, citric acid, benzoic acid, uric acid and their corresponding conjugate bases. Other organic components can independently be substituted as described in Wang, S. et al, Mol. Pharmaceutics 2015, 12, 4478-4487.

For CT imaging, cesium, tantalum, iopamidol, iohexol, ioxilan, iopromide, iodixanol, ioxaglate, diatrizoate, metrizoate, iothalamate, ethiodized polymers such as PLGA, PEG, albumins, DNA, RNA, ionic poly-carbohydrates and the combinations there of can be utilized. For ultrasound imaging, polymers are in general hypoechoic. However, when PLGA-PEG-PLGA (a block co-polymer, a reverse phase-transition hydrogel) is used, the polymer appears hypoechoic immediately after injection but subsequently turns into hyperechoic as temperature increases, indicating likely imageability. A similar observation was made when albumin is used as a carrier polymer.

Upon application of the electromagnetic energy (e.g., microwave, RF, electroporation), remotely deposited TA can absorb the energy much more effectively than the surroundings and help extend the ablation zone. Here, "remotely deposited TA" means in the far range, so would mean distance greater or equal to 1.5 cm from the microwave antenna, for example, when the conditions (e.g., 60 W 915 MHz for 10 minutes) are used. Using TA, the ablation zone can extend further from the antenna for a given power/time treatment, or the same ablation volume can be effectively ablated in a shorter time, or the degree of heating can be enhanced in specific tissue regions that are inherently less capable of microwave heating.

Upon application of the electromagnetic treatment energy (e.g., microwave, RF, electroporation) TA deposited adjacent to a large blood vessel can protect the ablation zone from heat loss, therefore TA can mitigate the "heat sink" effect to assure complete ablation. Moreover, suitably-placed TA may extend ablation to the far side of a vessel, enabling new treatment geometries for simple microwave antennas.

In addition, TA can be used in embolization/ablation combination treatments to destroy tumors. TA may be formulated with a similar viscosity to Lipiodol, and thus can be delivered via an intravascular catheter to be deposited accurately. A subsequent ablation can destroy tumors effectively.

The TA formulation may include excipients, which may depend upon the specific purpose. Excipients may, for example, include, PEG, lactose, microcrystalline cellulose, sodium starch glycolate, croscarmellose sodium, PVP, HPMC, magnesium stearate, colloidal $SiO_2$.

The tissue targets may be quite diverse, and use of TA in the field of Cancer/Tumor ablation may include breast (benign and malignant, thyroid (benign and malignant), lung (primary and metastatic), liver (primary and metastatic, liver surgery margin coagulation), adrenal (benign functioning, caner and metastatic), kidney (primary and metastatic), bone, prostate, soft tissue (primary and metastatic). In addition, the enhanced ablation accuracy, speed and uniformity offer promising improvements for Endometrial ablation/Menorrhagia: Uterus; Spinal Decompression and Denervation; Benign Prostatic Hyperplasia (BPH); as well as treating other tissues such as Esophagus (reflux), bronchial tree (emphysema reduction), biliary tree (stent obstruction from tumor), joints (laxity), surgical resection and bleeding.

As discussed above, in some embodiments, radiofrequency (RF) can drive ablation in addition to, and/or in lieu of, microwave energy. A person skilled in the art will recognize that RF can use electrical signals (e.g., a current) of varying frequency, e.g., both inside and outside frequencies of radio waves, to perform ablation. Among other ways to perform an RF ablation, needle-like electrodes can be placed percutaneously into the target tissue using imaging guidance (e.g., ultrasound, CT imaging, or MRI).

Figure 12:
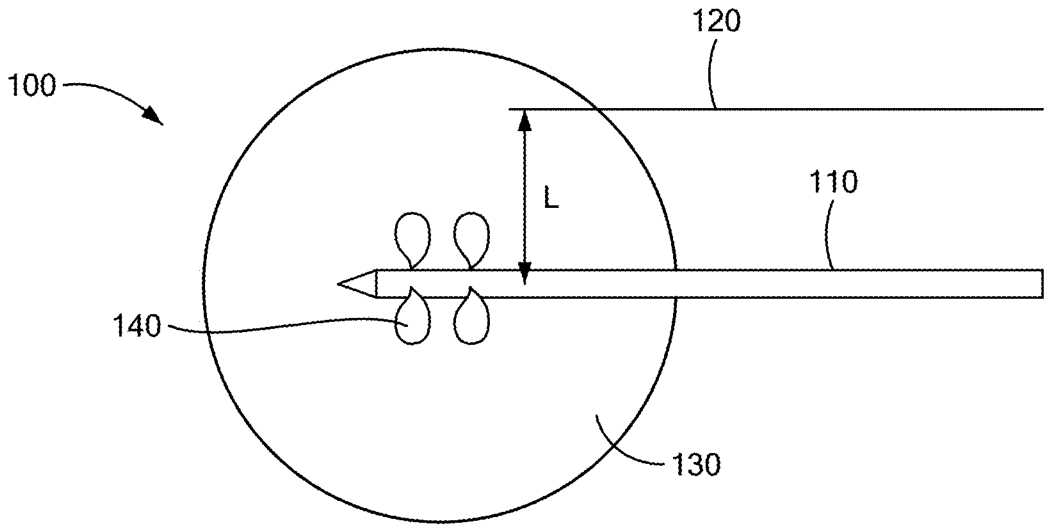
FIG. 12 schematically illustrates an arrangement of an electrode and TA being inserted into an organ of a patient.

FIG. 12 illustrates an exemplary embodiment of a setup 100 used for RF ablation. As shown, a probe, or electrode 110, and a thermocouple 120 can be inserted into tissue or an organ (both identified for simplicity by reference number 130), e.g., heart, liver, kidney, and so forth. A distance L between the probe 110 and the thermocouple 120 can vary, though in some embodiments, the distance L can be approximately 1 cm, approximately 1.5 cm, approximately 2 cm, and so forth. In some embodiments, the distance L can be set based on the type of tissue 130, the size of the tumor and/or desired ablation zone, and so forth. The probe 110 can include a metal shaft, which is insulated except for an exposed conductive tip that is in direct electrical contact with the targeted tissue. An RF generator (not shown) can supply RF energy to the tissue 130 through the electrode 110. The setup 100 can include a reference electrode (not shown), which can be positioned at a conductive pad contacting the patient's skin in an area of relatively good electrical and thermal conductivity. The RF generator produces a RF voltage between the active RF electrode and the reference electrode, thereby establishing lines of electric field within the patient's body between the two electrodes. The electric field oscillates with the RF frequency (<1 MHz).

The TA 140 can be positioned in the organ 130 before ablation begins. The TA 140 can be dispensed and/or delivered from the electrode 110, as shown, though, in some embodiments, the TA 140 can be injected or otherwise delivered into the organ 130 via a syringe or a similar apparatus known to one skilled in the art. During ablation, the ions in the tissue move with the oscillating field and proportionately to the field intensity causing friction, which is converted into heat. That is, ions in the tissue can cause collision among surrounding molecules, such as neighboring sodium and chloride ions. The collisions of these molecules generate kinetic energy, which can turn into heat. The TA 140 can exhibit similar oscillating properties, but at two or more orders of magnitude higher than the ions, which can generate significantly more heat than the ions, resulting in the increased ablation observed when the TA 140 is used.

Successful RF ablation of an entire tumor typically occurs at temperatures of greater than about 60° C. throughout the target area. In some embodiments, however, poor tissue penetration by certain electrodes can result in an inability to ablate tumors larger than 1 cm in diameter. Illustrative embodiments overcome these inherent problems by ablating larger tumors (e.g., larger than 1 cm) with multiple electrodes, multiple-hook electrodes, bipolar arrays, cooled-tip electrodes, and/or pulsed RF probes. In some embodiments, poor energy penetrations also can be improved by altering tissue dielectric properties. For example, various concentrations in a contiguous injection of saline solutions have shown a marked improvement in the larger ablation volume. Saline volume and concentration influence coagulation diameter in a non-linear fashion as increased saline concentration can increase electrical conductivity (which is inversely proportional to the measured impedance) and enable greater energy deposition in tissues without inducing deleterious high temperatures at the electrode surface. This effect is non-linear with markedly increased tissue conductivity decreasing tissue heating. The increased conductivity can be beneficial for RF ablation in that it enables increased energy deposition which increases tissue heating. However, given less intrinsic electrical resistance, increased tissue conductivity also increases the energy required to heat a given volume of tissue. When this amount of energy cannot be delivered (e.g., it is beyond the maximum generator output), the slope is negative and less tissue heating (and coagulation) will result. Thus, to achieve clinical benefit (i.e., an increase in RF induced coagulation), optimal parameters for saline injection need to be determined for each type of RF apparatus used and for the different tumor types and tissues to be treated.

A drawback of saline solution to improve RF ablation involves its discrepancy of geometry of ablation. Specifically, the saline solution is drained to the directions with the least resistance, which results in an uncontrolled shape of ablation with increased risk of collateral injury to adjacent organs or tissue, e.g., bile duct, diaphragm, nerves. Use of TA during RF ablation can mitigate these effects and increase a volume of the ablation zone as desired.

The impact of TA on a change of temperature of an ablation zone during RF ablation can be seen in the following examples:

Example 6

Radiofrequency Ablation of an Ex Vivo Swine Liver.

A radiofrequency system (Viva combo RF Generator, STARmed, Goyang, S. Korea) was used for all ablation procedures at a power of 35 W with a continuous mode for 10 minutes (FIG. 2). The RF applicator (15 G 2 cm ActiveTip) has perfusion ports at the tip through which 2 mL of TA were injected. The temperature change was measured 1.5 cm away in the transverse plane from the RF electrode. The thermocouple 120 was at the same depth as the RF electrode 110 tip as shown in FIG. 12. The experiments were repeated four times for control and TA, and the data were comparatively plotted and statistically analyzed (GraphPad PRISM© Version 6e).

Figure 13:
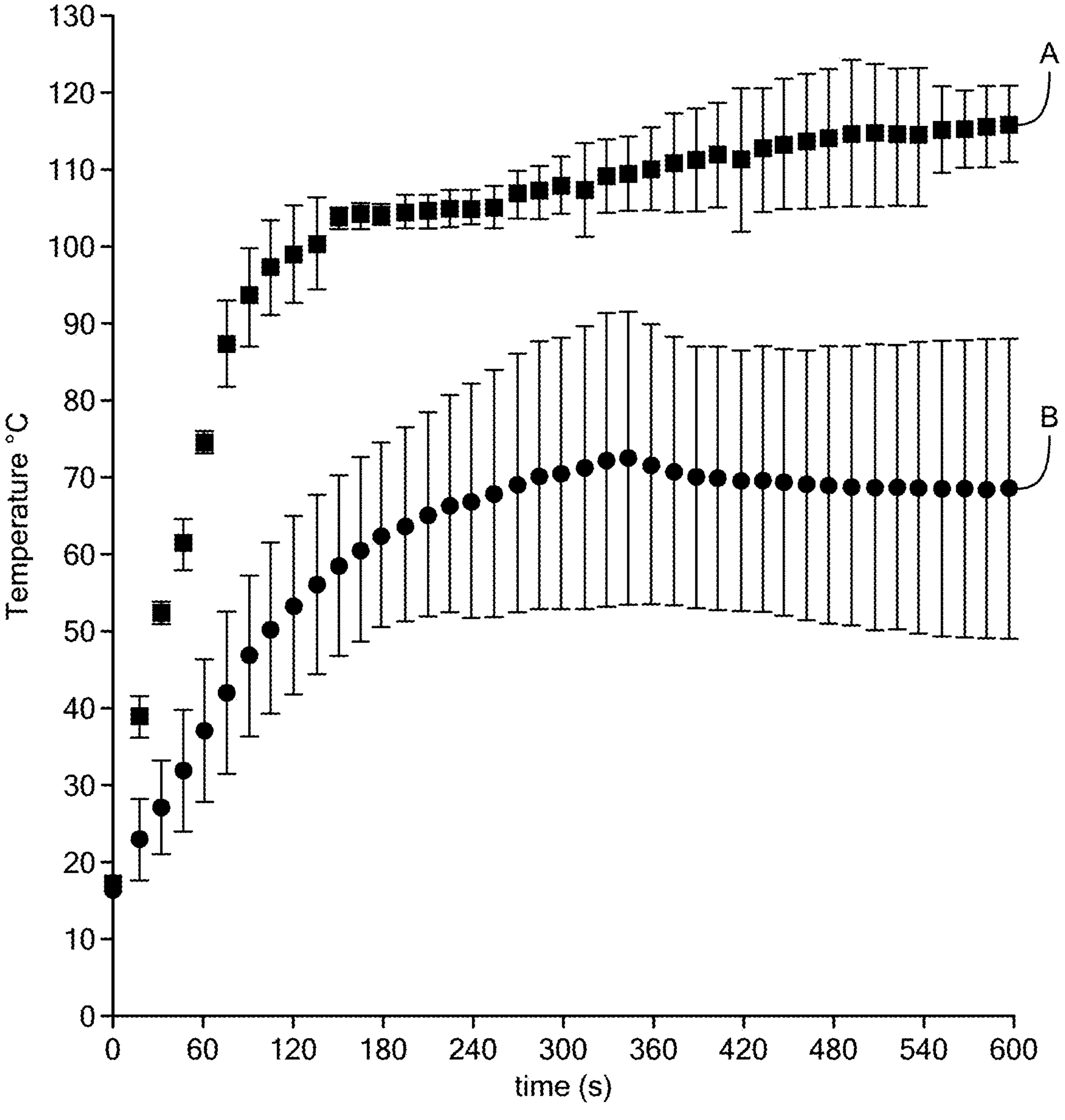
FIG. 13 illustrates temperature profiles of radiofrequency ablation using TA and control setups.

A total of 8 RF ablations were performed (four TA, four control). Overall, ablations performed using TA demonstrated a significantly higher rate of temperature increase than control, especially in the first 90 sec. During this period, the temperature increase was analyzed for linearity: control and TA (R square: 0.6695 and 0.9679, respectively). The slope of the rate was 0.3239±0.0446° C./s for control and 0.8178±0.0342° C./s for TA, respectively. Post-90 sec, temperature increase for both control and TA was slowed to ca. 70° C. and 110° C., respectively. Furthermore, the temperature variations for control appear to be significantly larger than TA throughout the measured period as shown in FIG. 13, which illustrates temperature profiles of radiofrequency ablation with the TA (A) and control (B). As shown, the temperature of the ablation with the TA (A) is higher than the control (B) throughout the duration of the ablation.

Example 7

Comparison of Ablation Zone Temperature Between TA and Various NaCl Solutions

Figure 14:
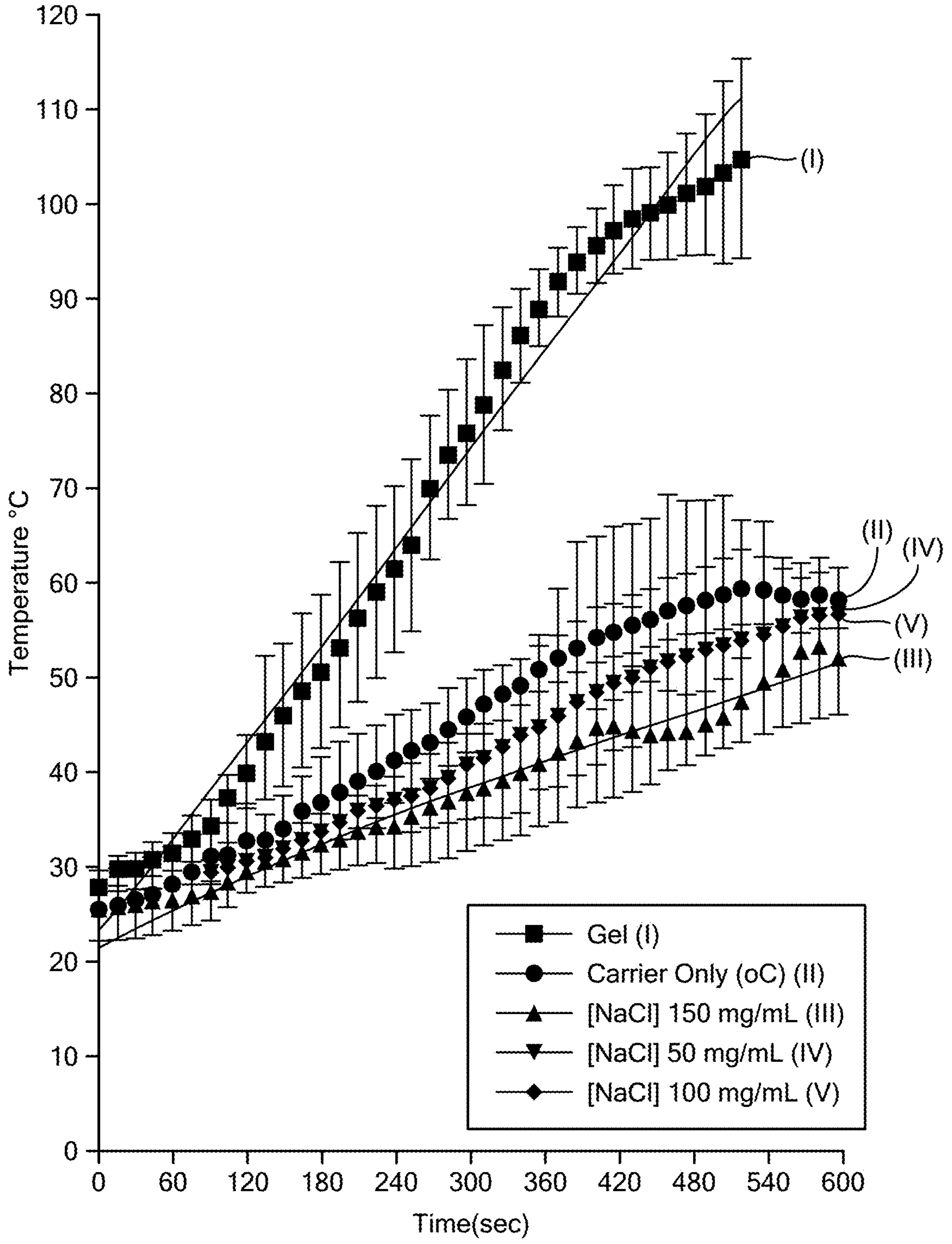
FIG. 14 illustrates temperature profiles of TA samples having varying concentrations over time.

Use of the TA can accelerate the ablation zone temperature change measured at a distance from the probe during RF ablation. For example, results of an RF ablation at a distance of 1 centimeter from the probe 110 in the bovine liver are shown in FIG. 14. The OsteoCool™ RF Ablation system (Medtronic Memphis Tenn.) was used for all ablation procedures with the following settings: ablation time 10 minutes; set temperature 95° C.; power limit 20 W; impedance cut off 50Ω. The RF applicator (18 G, 2 cm ActiveTip) was placed to the same site where a TA sample (1 mL) was injected. The TA samples are, 1) HeatSYNC Gel, 2) carrier biopolymer, 3) aqueous NaCl solutions with 50, 100, 150 mg/mL. The temperature change was measured 1.0 cm away from the RF applicator at the same depth as the applicator's tip. The experiments were repeated four times for all samples and the obtained data were comparatively plotted and analyzed by using a biostatistics software (GraphPad PRISM© Version 8). As a result, a total of 20 RF ablations were performed: five samples (each n=4). Ablations with the TA (I) showed a significantly higher rate of temperature increase than all other samples (III, IV, V) including a biocarrier sample (II).

In some embodiments, the TA can be used as a cauterizing agent. Once the RF energy heats the TA to a specific temperature, e.g., >80° C., the TA can coagulate and become integral with the ablated tissue. For example, the TA can be applied to a tissue or organ to augment heating of said tissue or organ and/or to cauterize the site to prevent bleeding. The TA can be applied as a gel to one or more surfaces thereof such that heating the TA merges with the ablated tissue to seal up the site.

Figure 15:
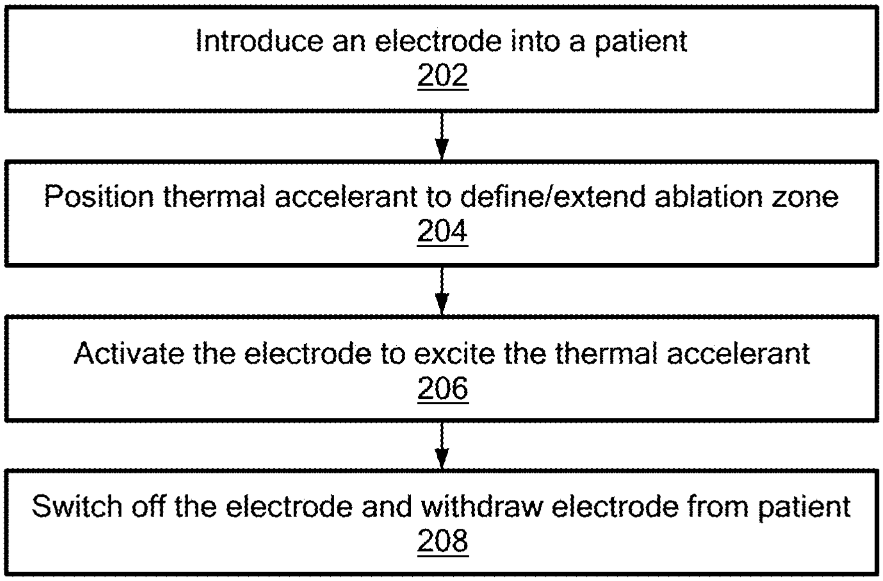
FIG. 15 illustrates a flowchart of an exemplary method using the compositions and systems disclosed herein.

FIG. 15 illustrates an exemplary method 200 of tissue ablation in accordance with the illustrative embodiments. It should be noted that, as described, this process is simplified from a longer process that normally would be used to perform an ablation. Accordingly, the process can have additional steps that those skilled in the art likely would use. In addition, some of the steps may be performed in a different order than that shown, or at the same time. Those skilled in the art therefore can modify the process as appropriate. Moreover, as noted above and below, materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

Referencing FIG. 12 and FIG. 15, the process 200 can begin at step 202 by introducing one or more electrodes 110 into a body of a patient to reach a target site. The target site can include a tissue, organ, tumor, and so forth. After insertion, the electrode 110 can be disposed within the target site, proximate to the target site, and/or extending through the target site. Next, the thermal accelerant 140 can be positioned within the body of the patient at a distance from the electrode (step 204). The thermal accelerant 140 can be positioned so as to define and/or extend an ablation zone for the target site. The relative distances between the TA 140, the electrode 110, and the target site 130 can vary based on the desired ablation zone, patient anatomy, the size of the target site, and so forth, as discussed in detail above. In some embodiments, a second electrode or a second thermal accelerant can be added to the target site, as discussed above, to maximize the ablation zone.

After positioning the thermal accelerant 140, the electrode 110 can be activated to excite the TA (step 206). In some embodiments, the electrode 110 can include one or more energy emitting devices (not shown) thereon to excite particles of the TA to a specific temperature. A person skilled in the art will recognize that the energy emitting devices can utilize one or more of microwave, radiofrequency, and electroporation to perform the excitation. In some embodiments, heating the TA can cause the TA to cauterize to the target site by coagulating to become integral with the ablated tissue. Heating of the TA can continue until it the target site has become sufficiently ablated. After ablation is performed, the electrode can be switched off and withdrawn from the patient (step 208).

Example 8

Thermal Accelerant May be Used as Drug Delivery Vehicle

In some embodiments, the TA can be used as a drug delivery vehicle to carry one or more drugs to the target site. Specifically, the ability of the TA to coagulate when exposed to ablative energy can allow the accelerant to be used for drug delivery. As described earlier, once the RF energy heats the TA to a specific temperature, e.g., >80° C., the TA can coagulate and become integral with the ablated tissue. For example, the TA can achieve locoregional and functional distributions of the anti-tumor drugs or agents, such as kinase inhibitors, to desired target areas. In illustrative embodiments, kinase inhibitors may include a combination of various nanotechnology and receptor tyrosine kinase inhibitors.

Figure 16:
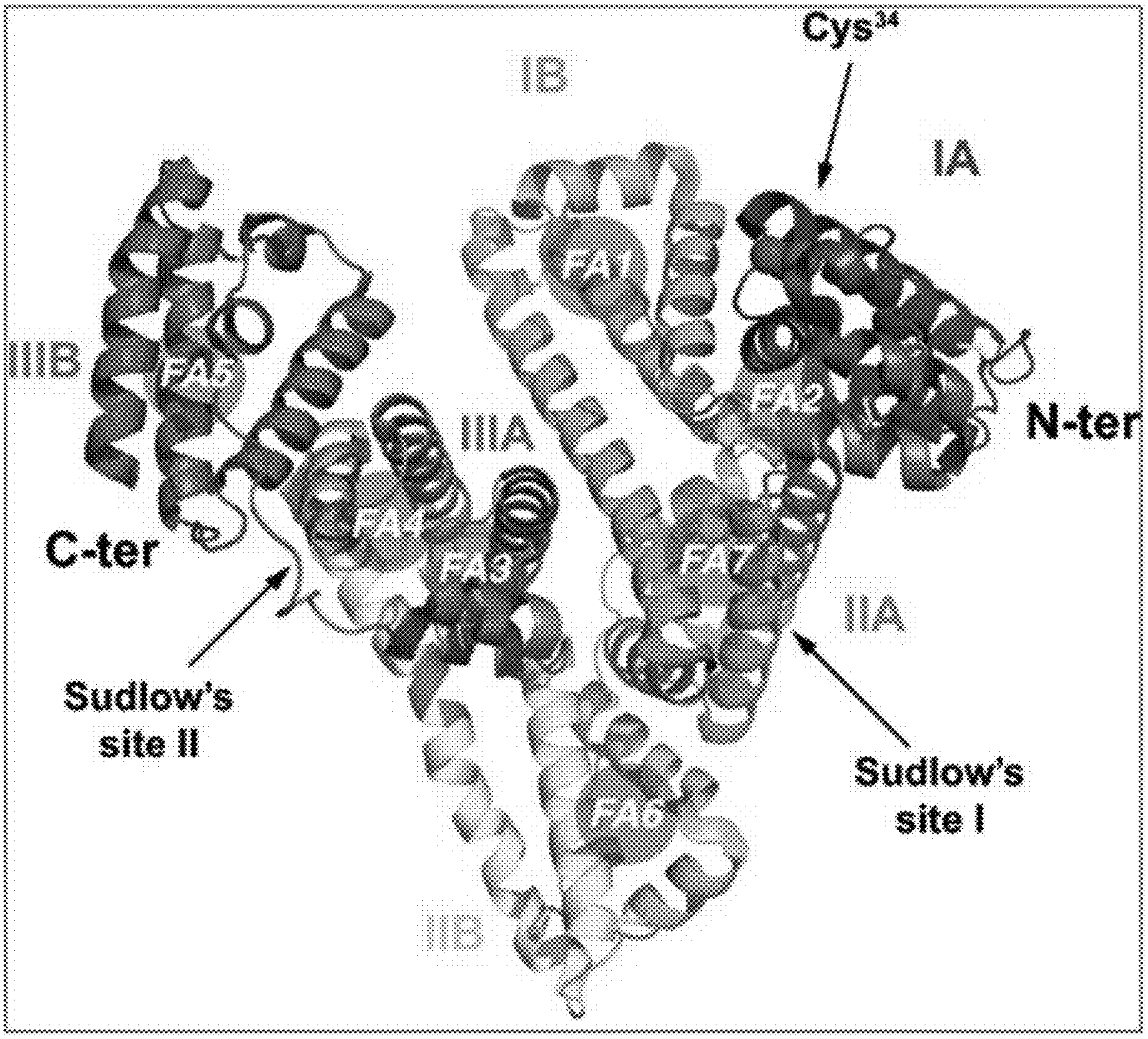
FIG. 16 illustrates a schematic of a crystal structure of human serum albumin as the carrier.

To design the albumin-based formulation with drugs, one or more of several strategies can be used. In an embodiment, drugs may be transported to a target area in a molecular carrier. FIG. 16 illustrates the structure of a carrier, such as human serum albumin (HSA), in greater detail in accordance with illustrative embodiments. Albumin contains three alpha helical domains each comprised of two subdomains. Its seven fatty acid binding sites are distributed asymmetrically across the protein. Additional sites of importance in binding include the free thiol located at the cysteine-34 amino acid residue and Sudlow's sites I and II, which bind a variety of nonspecific hydrophobic drugs.

In some embodiments, in situ formulation of the albumin is achieved in the body after an injected binder docks on to endogenous albumin. This type of formulation includes covalent conjugations (e.g., albumin cysteine-34 for drug conjugation; MMPs-2 and 9 for cleaving doxorubicin and the albumin-binding maleimide group), native ligand conjugates (e.g., siRNA-albumin for breast cancer) or small molecule binders (e.g., Evans Blue 14 molecules in one albumin). Alternatively, in some embodiments, exogenous formulations can be used that rely on drug loading into or covalently attached to recombinantly produced albumin or human serum albumin isolated from donors prior to injecting into patients. In such embodiments, covalent conjugation (e.g., methotrexate, curcumin, and doxorubicin), recombinant albumin fusion protein (e.g., N-terminus of proaerolysin linked with recombinant albumin), and nanoparticle formulation (e.g., Nab-paclitaxel known as Abraxane) can occur.

Figure 17:
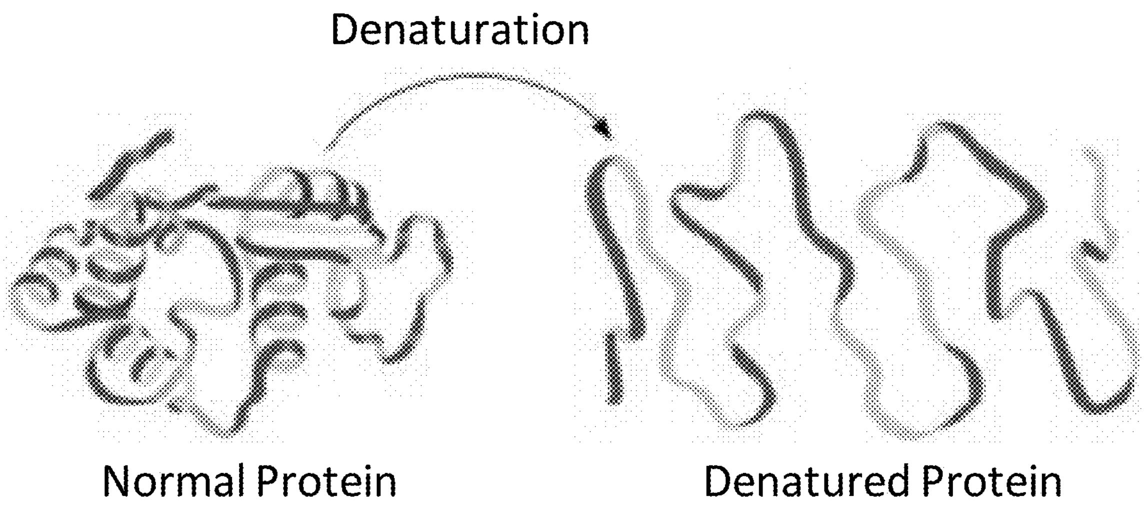
FIG. 17 illustrates a schematic representation of an exemplary embodiment of protein denaturation.

When albumin is exposed to heat energy (e.g., thermal energy provided by microwave ablation or RF ablation), the albumin molecule can become "structurally altered," or undergo a series of distinct structural changes, namely denaturation. FIG. 17 schematically illustrates a schematic illustration of the denaturation process in which a 3-D structure is denatured into a linear protein. As shown, the denaturation process entails the breakdown of 3-dimensional architecture of the albumin molecule. The denaturing process includes disruption of its quaternary (subunit integrity disruption), tertiary (disulfide bonding and non-covalent (polar) interactions, and Van der Waals (non-polar) interactions) and secondary (β-sheet and a helices) structures.

In addition to these disrupted intramolecular processes, many new intermolecular interactions form through new disulfide bridges or hydrogen bonding and non-polar interactions, resulting in a protein meshwork. Overall, the protein meshwork is structurally arranged in a manner that hydrophobic moieties are on the surface while hydrophilic moieties turn inward. In the ablation-drug carrying albumin formulation, polar drug molecules are transferred to the hydrophilic site (e.g., non-polar molecules will be trapped on the hydrophobic surface). Therefore, after ablation is complete, the structurally transformed protein meshwork is spatially fixed adjacent to the ablated diseased tissue as a biodegradable implant, and the drug molecules are released from the protein meshwork over time. Throughout the entire process, a person skilled in the art will recognize that the protein backbone (primary) structure remains intact.

As shown and noted above, the conformational change can result in a change in shape of the albumin molecule such that the albumin is transformed into a particular shape. The conformational change can be irreversible such that disruption of the quaternary, tertiary, and secondary structures of the molecule can be permanent such the albumin does not return to its original shape and represents a different structure, for example, a protein meshwork having a substantially porous structure. Ablation of the TA can change a conformation of the albumin envelope of the HSA of the TA. For example, ablation of the TA can cause denaturation of the proteins in the HSA (e.g., a carrier) and release of the anti-tumor agent bound to the proteins of the TA following impregnation of the anti-tumor agent. That is, a drug may be bound to a carrier, and ablation can alter the shape of a carrier to cause the carrier to release the drug.

Prior to delivery, the TA can be impregnated with, or covalently attached to, one or more anti-tumor agents and delivered to the target site or an area such as a periphery of the tumor. The TA can be adsorbed at the target site, and when exposed to energy (e.g., thermal energy, or heat), as discussed above, can be transformed into a necrotic coagulation during ablation and become implanted at the target size or at the periphery of the tumor, e.g., the TA can become a part of scar tissue in a coagulated protein meshwork. In some embodiments, one or more suitable acids, bases, metal or metal ions, salts, buffer or chaotropes can be added to adjust polarity of the carrier molecule for kinetic movements during ablation. In illustrative embodiments in which the anti-tumor agents are covalently bonded to the TA, dissociation can occur to release the anti-tumor agents by hydrolyzing the bonding.

A concentration of the albumin used for drug delivery can range from approximately 30 mg/mL to approximately 600 mg/mL, though in some embodiments, the concentration can range from approximately 30 mg/mL to approximately 300 mg/mL, or 30 mg/mL to approximately 150 mg/mL. Lower concentrations of albumin, e.g., 30 mg/mL, can be used for drug delivery as compared to ablation, e.g., >300 mg/mL as discussed above, as the TA is used to deliver the drug to the target site and is then denatured to release the impregnated drug therefrom. Lower concentrations of the TA can expedite the denaturation of the TA, as well as the release of the anti-tumor agent, while also allowing for a greater percentage of the concentration of the TA-drug combination to be made up of the drug, which allows more of the anti-tumor agent to be delivered to the target site for release into the body for treatment.

Some non-limiting examples of such energy-stable anti-tumor agents can include kinase inhibitors, non-kinase inhibitors, including doxorubicin, taxol, resatorvid, tamoxifen, trichostatin A, enzalutamide, cyclosporin A, etoposide, or SUMOylation inhibitors, inhibitors at various checkpoints such as PD1/PD-L1, CXCR, Sting, IDO, or TLR, among others. In the case of kinase inhibitors, these inhibitors block the deregulated kinase activities, i.e., phosphorylation that is a frequent cause of disease, in particular cancer. Some non-limiting examples of kinase inhibitors that can be used with the present disclosures can include Fasudil (Eril), Sirolimus (Rapamune), Imatinib, Gefitinib, Erlotinib, Sorafenib, Sunitinib, Dasatinib, Lapatinib, Nilotinib, Temsirolimus, Everolimus, Pazopanib, Ruxolitinib, Vandetanib, Vemurafenib, Crizotinib, Icotinib, Axitinib, Tofacitinib, Bosutinib, Cabozantinib, Ponatinib, Regorafenib, Afatinib, Dabrafenib, Trametinib, Ibrutinib, Nintedanib, and/or Idelalisib. Moreover, the anti-tumor agent that impregnates the TA can be customized based on a type of tumor that is to be attacked. For example, prior testing and/or imaging can be performed at the target site to determine the nature of the tumor and the TA can be impregnated with one or more anti-tumor agents that can best target and destroy said tumor.

The albumin, e.g., HSA, can modify its structure based on the anti-tumor agent being carried. After coagulation, the conformational change of the protein can change a percentage of the protein that binds with the drug. The availability of the drug that is delivered to the target site can change based on the amount of protein that is available to bind to the drug. For example, as the protein in albumin denatures, the binding affinity towards the drug of the overall albumin alters, thereby making the kinase inhibitors locally available. In some embodiments, the albumin can be optimized by calculating an amount of the drug that would bind to the protein in the albumin to determine the amount of albumin impregnated with the anti-tumor drug that is being injected at the target site. Once the impregnated TA arrives at the target site, the anti-tumor drug can be released therefrom.

The protein binding state between the anti-tumor agent and the TA can change the release rate of the agent from the TA once implanted at the desired location with an increase in the protein binding percentage increasing a release rate of the drug, and vice versa. In some embodiments, the agent can be released from the TA via delayed release. The delayed release allows for larger concentration of the anti-tumor drug, e.g., kinase inhibitor, to be disposed within the TA, which increases the efficacy of treatment of the tumor.

The TA can be configured to release the anti-tumor agent therefrom via delayed release. For example, once sufficiently coagulated following ablation, the protein meshwork can release the anti-tumor agent therefrom over a time period of that can depend on a newly established equilibrium ($K_{diss}$) between the drug and the protein meshwork. The factors influencing the drug release equilibrium ($K_{diss}$) can include ionic interactions, hydrogen bonding, weak interactions such as van der Waals between water molecules, drug molecules, trapped chaotrope molecules, and/or the amino acid residues within the protein meshwork structure.

The ability for delayed release of the anti-tumor agent is advantageous to allow the TA to be placed and implanted in a desired location relative to the tumor to ensure that the anti-tumor agent is optimally targeting the location to the tumor. In some embodiments, the TA can be configured to denature over an extended period of time such that the TA releases the anti-tumor agent over the course of the denaturation. A length of time that the anti-tumor agent can remain in the body can depend on the nature of the anti-tumor agent being used.

Temperature-sensitive therapeutics such as some small molecule drugs, siRNA, nucleoside analogs, or DNA can be used in a similar strategy by employing other energy sources. The thermal accelerant can augment microwaves and RF energy during ablation to help achieve complete ablation of tumors. In some embodiments, the TA can augment a number of non-thermal or minimally thermal energies, such as irreversible electroporation (IRE) or sonar waves, such as in high-intensity focused ultrasound (HIFU) or histotripsy. Use of the TA results in the larger ablation volume and more spherical in shape than ablations without the TA in a dose-dependent manner. The use of the TA in tandem with ablation will contribute to eliminating the local tumor recurrence, the largest challenge that the current ablation technologies face.

Small molecule therapeutics can be formulated with albumin (or other carriers) for a wide range of therapeutic areas, e.g., cancer, infectious disease, inflammation/immunology, neurological disease, cardiovascular disease, endocrinology, metabolic disease and/or other rare diseases. Many of the small molecule therapeutics are thermally stable during microwave ablation or RFA. The strategy is advantageous for localizing drug-release thus eliminating drug-associated adverse effects.

In some embodiments, as suggested above, the anti-tumor agents impregnated in TA can be used in conjunction with non-thermal ablative technologies. Specifically, the denaturation that albumin experienced during ablation may also occur during non-thermal processes that can cause the albumin to lose its structural integrity. For example, irreversible electroporation (IRE) or histotripsy are non-thermal ablative technologies that can affect the albumin structure without involving heat by the applied strong electrical pulse or intense sonar energies, respectively. IRE, which is a process that uses high-voltage, low-energy DC current pulses to induce cell death, is non-thermal and causes lesser alteration of the albumin structure than other thermal ablation methods. The non-thermal ablation technique(s) therefore allows use of a wider variety of heat-labile anti-tumor agents, e.g., both small and large synthetic molecules and siRNA, peptides, carbohydrates, antibodies, nucleoside analogs that invoke anti-tumor immune responses can be used because the lower temperature processes do not affect the structural integrity of the therapeutic agents. For example, in such embodiments, the anti-tumor agents contained in the TA can include not only small-molecule, thermally stable antitumor agents, but also therapeutic agents having larger molecules that invoke anti-tumor immune responses such as monoclonal antibody: e.g., PD-1 Pembrolizumab (Keytruda), Nivolumab (Opdivo), Cemiplimab (Libtayo), PD-L1 Atezolizumab (Tecentriq), Avelumab (Bavencio), Durvalumab (Imfinzi) and CTLA4 Ipilimumab (Yervoy); or nucleoside analog-based agents, among others. Moreover, in some embodiments, the TA can also be impregnated with the above-listed substance when applied to histotripsy, another non-thermal ablation method that induces cavitation of target tissue followed by tumor cell-death by HIFU energy. Non-thermal ablation techniques, such as TRE or histotripsy, with a therapeutic substance (e.g., siRNA, peptides, proteins, immunoglobulins, glycoproteins, RNA, DNA, and nucleoside analogs) can cause systemic anti-tumor immune responses to result in abscopal effect where one may observe shrinkage of untreated tumors concurrently with the treatment of tumors within the scope of the locoregional treatment, as discussed in greater detail below. Non-thermal ablations (IRE or histotripsy) with therapeutic substance (e.g., siRNA, peptides, proteins, immunoglobulins, glycoproteins, RNA, DNA, and nucleoside analogs) can cause systemic anti-tumor immune responses to result in abscopal effect where one may observe shrinkage of untreated tumors concurrently with the treatment of tumors within the scope of the locoregional treatment.

Albumin has several advantages in the combination therapy of the energy-based ablation and the therapeutic substance, such as, for example, protection of small biomolecules such as siRNA, peptides, proteins, immunoglobulins, glycoproteins, RNA, DNA, and nucleoside analogs. In some embodiments, therapeutics may be endocytosed via albumin receptors expressed more on the tumor cells. In embodiments, the energy-based ablation that combines a thermal treatment with a therapeutic substance (e.g. a drug) may be considered a thermally-activated combination therapy (e.g., TACT).

Non-thermal ablative techniques such as IRE, HIFU, or histotripsy can contribute to a different mechanism for ridding the body of tumor cells as compared to thermal ablative technologies, such as MWA or RFA, discussed above. For example, the non-thermal ablative techniques can trigger an immune response within the body of the patient to rid itself of the diseased substances. As discussed above, during IRE, HIFU, and histotripsy, the temperature of the thermal accelerant is not raised to the levels seen with MWA or RFA, which does not cause charring or destruction of the tumor cells. Rather, the non-thermal techniques cause tumor cells to burst, which releases its contents, e.g., tumor cell surface or cytosol having tumor specific antigens, into the interstitial space as compared to a clearing out process that causes scar tissue formation that is seen with RFA or MWA. The presence of the tumor specific antigens in the interstitial space can attract antigen presenting cells (APCs) including macrophages, B cells and dendritic cells to consume the damaged tumor cells, which causes these cells to express the tumor specific antigen on APC's surfaces. This tumor specific antigen can trigger an immune response by the body's defense mechanisms, such as T cells or B cells, which attack these APCs, and destroy the cells, thereby destroying the tumor cell cytosol while also producing antibodies against this tumor specific antigen. A person skilled in the art will recognize that the strength of the immune response following non-thermal ablative techniques can be more robust than the immune response following MWA or RFA ablation, as the body's defense mechanism identifies and attacks the cytosol as a foreign intruder that must be killed rather than tumor specific antigens that have been already been deformed from their original shape and killed by thermal ablation.

Figure 18:
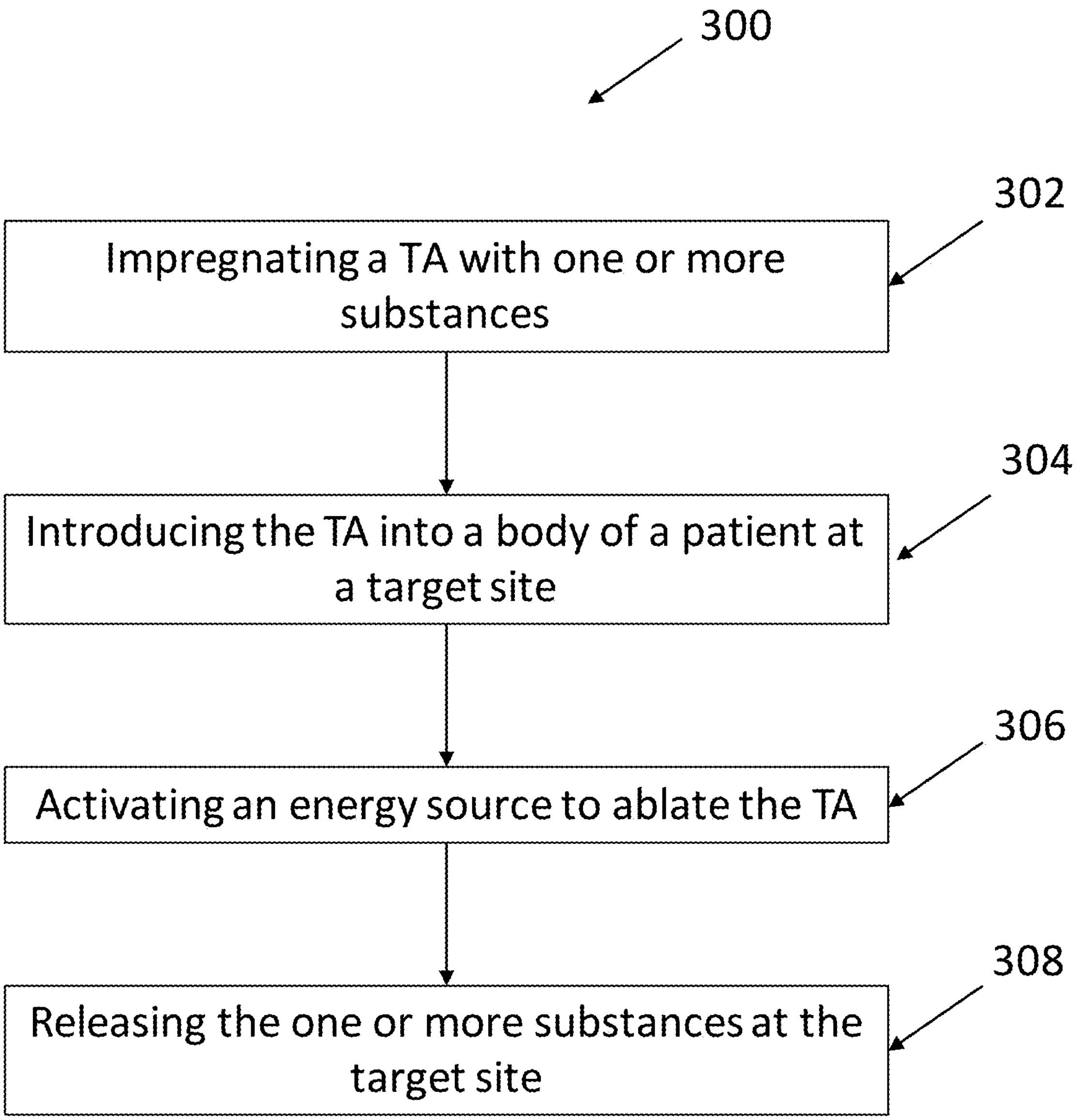
FIG. 18 illustrates a flowchart of another exemplary method for using the carrier as a drug delivery vehicle.

FIG. 18 illustrates an exemplary method 300 of using the thermal accelerant as a drug delivery vehicle in accordance with the present embodiments. It should be noted that, as described, this process is simplified from a longer process that normally would be used to perform an ablation. Accordingly, the process can have additional steps that those skilled in the art likely would use. In addition, some of the steps may be performed in a different order than that shown, or at the same time. Those skilled in the art therefore can modify the process as appropriate. Moreover, as noted above and below, materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

The process 300 begins at step 302 by impregnating a thermal accelerant with one or more substances, e.g., anti-tumor agents. Next, the TA can be introduced into a body of a patient proximate to a target site (step 304). The TA can be injected, delivered, or otherwise placed proximate to the target site by one or more methods known to one skilled in the art. After the TA is at the target site, an energy source can be activated to ablate the TA (step 306). The energy source can cause the TA to coagulate at the thermal site. During coagulation, the carrier can become denatured, causing the substances to be released from the TA into the target site (step 308). Release of the substances can be time-based and/or delayed as discussed above.

The illustrated and described systems, devices, methods, configurations, shapes, and sizes are in no way limiting. A person skilled in the art, in view of the present disclosures, will understand how to apply the teachings of one embodiment to other embodiments either explicitly or implicitly provided for in the present disclosures. Further, a person skilled in the art will appreciate further features and advantages of the present disclosure based on the above-described embodiments. Accordingly, the disclosure is not to be limited by what has been particularly shown and described, except as indicated by the appended claims.

Example 9

HSA-Based #1 Gel as a Combined Thermal Accelerant and Drug Delivery System

HSA-Based #1 Gel as a Thermal Accelerant

The HSA-based #1 gel is a protein-based formulation that with the following properties. First, the gel alters dielectric properties of target tissue to augment the applied energy. Second, the gel is a viscous solution so that it is stationary at a target site once deposited. Third, once the gel reaches a specific temperature or higher (>7° C.), the gel becomes coagulated and becomes a part of the ablated tissue. By becoming a part of the ablated tissue, the coagulated HSA-based #1 gel improves the performance of image-guided tumor ablation (e.g., IGTA). The coagulation at temperatures higher than 7° C. has demonstrated in several in vivo studies that the gel can improve performance of IGTA by producing a more spherical and larger ablation volume in the target tissue in a shorter time than could be performed without the gel. The use of the HSA-based #1 gel in IGTA reduces the local recurrence rate currently associated with IGTA technology without the use of the gel. Currently, the local recurrence rate is about 30%). However, by incorporating the HSA-based #1 gel in the IGTA process, the local recurrence rate is reduced to about 10-15%, which is about the rate of local recurrence of surgical resection.

Figure 19:
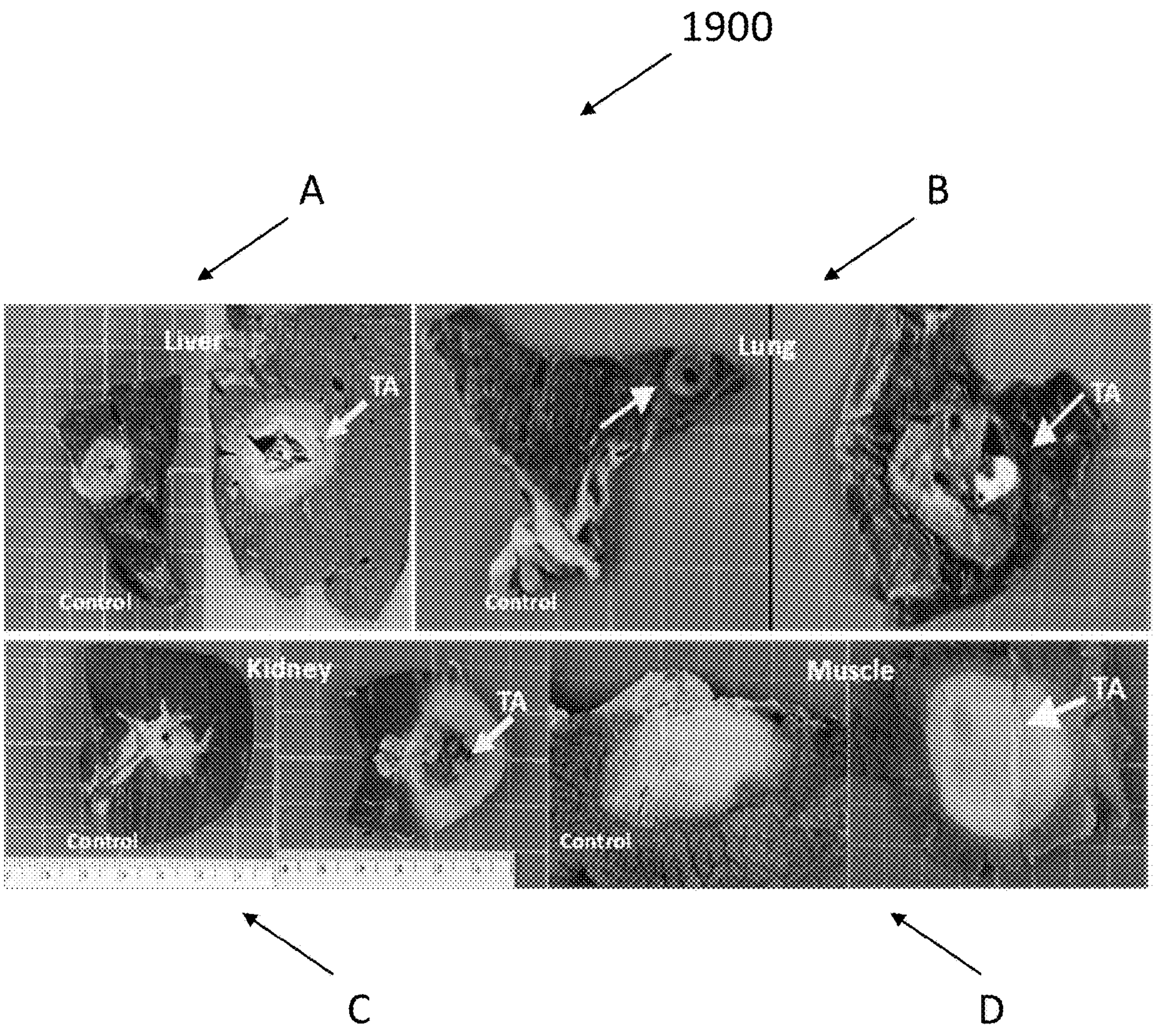
FIG. 19 shows images of ablated tissue.

FIG. 19 shows images of ablated tissue. The ablation study compared in vivo porcine tissue of several types treated with a thermal accelerant (TA) and without (Control) under ablation conditions: 915 MHz, 60 W, distance between antenna and HSA-based #1 gel (2 mL) for 10 minutes). Post ablation, the tissues were sectioned and treated with a triphenyltetrazolium chloride solution, a tissue viability stain: top left (A): liver; top right (B): lung; bottom left (C): kidney; bottom right (D): gluteal muscle.

In each tissue type, the sample that had been ablated in the presence of the thermal accelerant (TA) had substantially larger areas of treated tissue than the corresponding Control sample. The sections show that the treated tissue is more circular, which is indicative of a more spherical treatment volume, and the treated area is larger in the TA samples. This indicates that the presence of TA during ablation produces the volume of treated tissue that is more spherical and larger than the Control (e.g., no TA) sample.

Figure 20A:
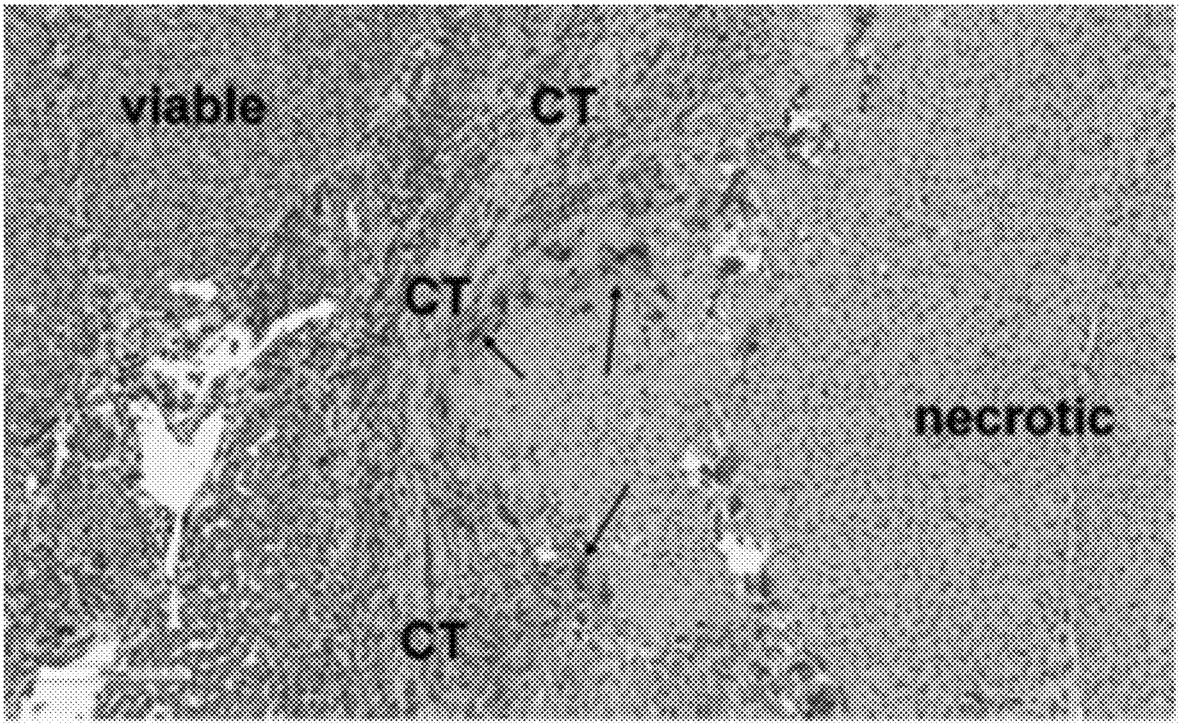
FIG. 20A shows images of ablated porcine liver without the HSA-based #1 gel histology.
Figure 20B:
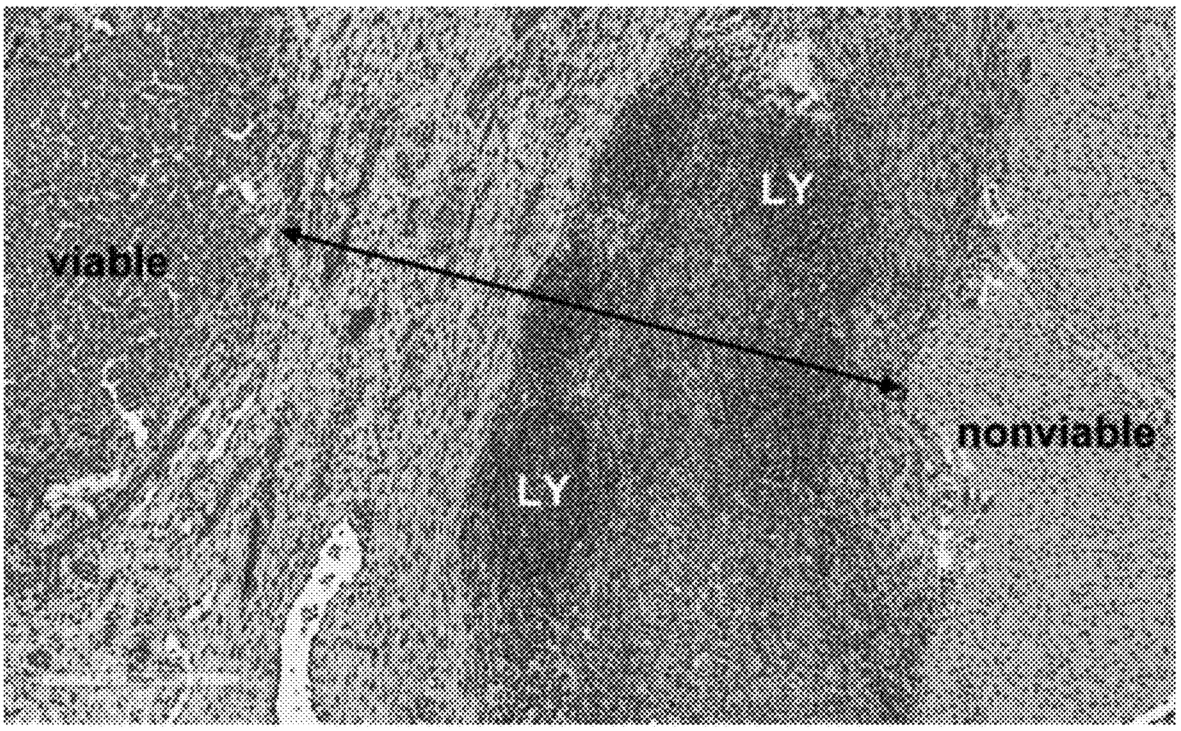
FIG. 20B shows images of ablated porcine liver with the HSA-based #1 gel histology.

FIGS. 20A and 20B show images of ablated porcine liver without (FIG. 20A) and with (FIG. 20B) the HSA-based #1 gel histology. FIG. 20A shows tissues 2000 that were ablated without the HSA-based #1 gel histology and shows that the connective tissue capsule (CT) surrounding necrotic/dead liver contains macrophages which are often multinucleated (arrows). FIG. 20B shows that tissues 2010 that were ablated with the HSA-based #1 gel histology increased numbers of scattered and clustered macrophages and lymphocytes (LY) in the connective tissue capsule surrounding necrotic/non-viable liver.

HSA-Based #1 Gel as a Drug Delivery System

In illustrative embodiments, the post-ablation coagulated gel may be used as a drug-depot and release the drug of choice over time. Most drugs are miscible with HSA-based #1 gel since the albumin molecule is amphiphilic in nature. Furthermore, albumin is known to be a carrier of a wide variety of both endogenous and exogenous compounds [Molecular aspects of ligand binding to serum albumin. Kragh-Hansen U Pharmacol Rev. 1981 March; 33(1):17-

53.]. This facilitates the colloidal solubilization and transport of hydrophobic molecules such as long chain fatty acids as well as a variety of other ligands such as bilirubin, metal ions such as zinc and copper, and drugs such as warfarin and ibuprofen [Crystal structure of human serum albumin complexed with fatty acid reveals an asymmetric distribution of binding sites. Curry S, Mandelkow H, Brick P, Franks N Nat Struct Biol. 1998 September; 5(9):827-35.]. Hoogenboezem E N, Duvall CL. Harnessing albumin as a carrier for cancer therapies. Adv Drug Deliv Rev. 2018 May; 130:73-89. doi: 10.1016/j.addr.2018.07.011. Epub 2018 Jul. 27. PMID: 30012492; PMCID: PMC6200408.

Once impregnated in the HSA-based #1 gel, the drug may be delivered to a target site, typically 1-1.5 cm from the feed point of the applicator. The subsequent ablation destroys most of the tumor mass and coagulates the gel, the drug is trapped in the coagulated protein meshwork. Through conformational changes of the albumin molecule in the HSA-based #1 gel during ablation, new drug-albumin interactions will be achieved from which the drug is eluted to the post-ablation tumor microenvironment (TME). This approach is advantageous over other drug delivery modalities in the following aspects: The drug is eluted from the target site as the coagulated protein meshwork is localized as a 'semi' permanent implant. Therefore, the drug is only available to the target area and minimizes the harmful systemic distribution. Furthermore, as most of tumor mass is destroyed at the completion of thermal ablation, the dose of drug also can be kept minimized when formulated with the HSA-based #1 gel.

A vast number of drugs can be formulated with the HSA-based #1 gel except thermally unstable drugs. More specifically, therapeutics that are unstable over 12° C. may be excluded.

Two drugs, Doxorubicin and Resiquimod, are selected as the candidates for demonstrating the thermal ablation-drug delivery combination therapy. That is, Doxorubicin and Resiquimod are selected to demonstrate a combined therapy where a thermal treatment is combined with a therapeutic substance (e.g. a drug). Such a treatment describes a thermally-activated combination therapy (e.g., TACT).

Doxorubicin is in the anthracycline and antitumor antibiotic family of medications. It works in part by interfering with the DNA function of the cell either healthy or diseased indiscriminately. This small-molecule chemotherapy agent is used to treat breast cancer, bladder cancer, Kaposi's sarcoma, lymphoma, and acute lymphocytic leukemia. It is often used together with other chemotherapy agents. ["Doxorubicin Hydrochloride". The American Society of Health-System Pharmacists. Archived from the original on 11 Oct. 2016. Retrieved 12 Jan. 2017].

Doxorubicin is given by intravenous injection. Dose as a single agent is 60 to 75 mg/m2 given intravenously every 21 days. Due to its small size, doxorubicin like other chemotherapeutics such as cisplatin or gemcitabine, have unfavorable pharmacokinetics and a suboptimal biodistribution, as exemplified by a short blood half-life and prominent off-target accumulation in multiple healthy organs. This, together with the unspecific mechanism of action of chemotherapeutic drugs and their large volume of distribution, causes severe side effects, such as myelosuppression, mucositis, neurotoxicity, nausea, vomiting and alopecia. Therefore, it is perfectly suited for the drug-HSA-based #1 gel strategy to be compared with the current regimen of Doxorubicin.

Resiquimod (R848) is an agonist of TLR 7/8 that acts as an immune response modifier, has antiviral and anti-tumor activity. A cardinal feature of cancer is the evasion of immunity via immunosuppressive signaling within the tumor microenvironment. This feature is common in PDAC: both local immunosuppression and structural barriers, such as stromal desmoplasia, are key therapeutic challenges. The TLR7 agonist imiquimod is FDA-approved as a monotherapy for basal cell carcinoma and the potential for TLR agonists is expanding into other malignancies. In some cases, TLR7 stimulation of T cells alone is sufficient for anti-tumor responses: nanoparticle delivery of R848 to CD8+ T cells results in increased anti-tumor immunity and prolonged survival in a murine colorectal cancer model. TLR7 agonists also demonstrate benefit in combination with doxorubicin in T cell lymphoma, with vaccination in bladder cancer, and with radiotherapy in gastrointestinal tumors [Michaelis, K. A., Norgard, M. A., Zhu, X. et al. The TLR7/8 agonist R848 remodels tumor and host responses to promote survival in pancreatic cancer. Nat Commun 10, 4682 (2019). https://doi.org/10.1038/s41467-019-12657-w.]

In an animal disease model, systemic administration of resiquimod-loaded nanoparticles has been shown to improve response rates to cancer immunotherapy with a checkpoint inhibitor through stimulation of tumor-associated macrophages. [Rodell, Christopher B.; Arlauckas, Sean P.; Cuccarese, Michael F.; Garris, Christopher S.; Li, Ran; Ahmed, Maaz S.; Kohler, Rainer H.; Pittet, Mikael J.; Weissleder, Ralph. "TLR7/8-agonist-loaded nanoparticles promote the polarization of tumour-associated macrophages to enhance cancer immunotherapy". Nature Biomedical Engineering. 2018 2 (8): 578-588.] It is noted that we have observed a discernable increase of macrophage recruitment to the area of the coagulated HSA-based #1 gel after thermal ablation in our porcine chronic safety study as shown in FIG. 20A and FIG. 20B. This implies that there are increased innate immune responses to the coagulated HeatSYNC gel. Further, the increased macrophages present the opportunities in various cancer targeting immunotherapies. [Duan Z, Luo Y, Targeting macrophages in cancer immunotherapy, Nature (Signal Transduction and Targeted Therapy), 2021, 6: 127.]

Example 10

Demonstration that the HSA-Based #1 Gel is Miscible with Drugs and Elutes the Drugs During and after Ablation In illustrative embodiments, the HSA-based #1 gel is miscible with the drugs previously discussed (e.g., Doxorubicin and Resiquimod), the mixed formulation still performs as a thermal accelerant, the drugs are structurally stable during ablation within the coagulated protein meshwork, and the drugs are released from the protein meshwork over time. These properties are important for the use of HSA-based #1 gel as a drug depot eluting anti-tumor agents after microwave ablation.

The following studies demonstrates that Doxorubicin can be miscible with the HSA-based #1 gel and is eluted out from the coagulated HSA-based #1 gel after ablation.

Aim 1: It is demonstrated that Doxorubicin can be miscible with the HSA-based #1 gel and is eluted out from the coagulated HSA-based #1 gel after ablation.

Method 1: In a 1% (w/v) agarose gel as phantom, HSA-based #1 gel (0.5 mL) with Doxorubicin HCl (2.0 mg) was placed 1 cm away from a MW antenna at ambient temperature. The ablation was performed at 60 W for 10 minutes (MicroThermX/Varian 915 MHz). Post ablation, the cooled agarose gel was left at ambient temperature for 48 hours for diffusion of the Doxorubicin.

Figure 21:
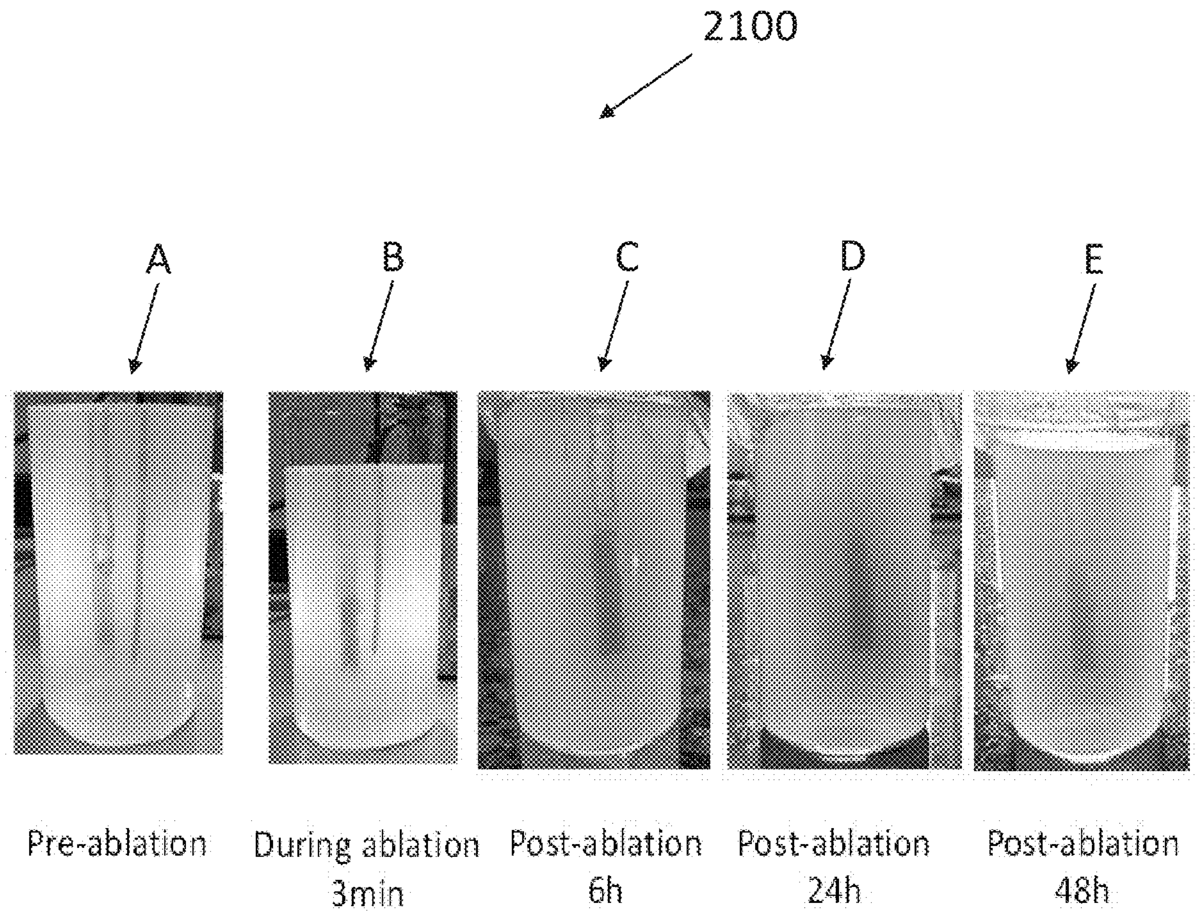
FIG. 21 shows images of the drug elution of Doxorubicin+HSA-based #1 Gel, before ablation (far left), during ablation (3 min), 6 h, 24 h and 48 h post ablation, respectively.

Results 1: Doxorubicin HCl (2.0 mg) is mixed with HSA-based #1 gel (0.5 mL) to result in a transparent orange-colored liquid as shown in FIG. 21. The mixture was placed in a pre-bored column using a 1 mL syringe followed by ablation, as shown in the Pre-Ablation photograph. During ablation, coagulation started to appear at ca. 70° C. Immediately after ablation, the orange-colored coagulated HSA-based #1 gel showed no diffusion out of the protein meshwork. At 6 h diffusion of Doxorubicin to the surrounding area of the phantom was apparent, and the diffused area becomes steadily larger as the time increased as shown in FIG. 21.

FIG. 21 shows images 2100 of the drug elution of Doxorubicin+HSA-based #1 Gel, before ablation (A), during ablation (B) (3 min), 6 hours after ablation (C), 24 hours after ablation (D), and 48 hours post ablation (E), respectively. The solution contained 1 (w/v) % agarose phantom. The ablation conditions: 915 MHz, 60 W for 10 minutes.

FIG. 21 illustrates the progression of eluting a drug, Doxorubicin, from a protein meshwork of HSA-based #1 gel. In A, prior to ablation, the Doxorubicin is held within the protein meshwork of HSA-based #1 gel. In B, 3 minutes into the 10 minute ablation exposure, Doxorubicin is beginning to escape the protein meshwork of HSA-based #1 gel. In C, 6 hours after the completion of the ablation exposure, more Doxorubicin is escaping the protein meshwork of HSA-based #1 gel. In D and E, 24 hours post ablation and 48 hours post ablation, respectively, more Doxorubicin is escaping the protein meshwork of HSA-based #1 gel as the time increases post ablation.

Example 11

The following studies demonstrates that the elution of Doxorubicin from the HSA-based #1 gel is dose dependent and that Doxorubicin continues to be eluted from the HSA-based #1 gel after ablation.

Aim 2 In vitro elution rate of various concentrations of Doxorubicin, a cytotoxic antitumor agent, is determined.

Methods 2 Absorbance values of three known concentrations of Doxorubicin samples ($1.0\times10^{-6}$, $9.5\times10^{-6}$ and $1.9\times10^{-5}$ M) were obtained to established a linear relationship (FIG. 4, Left) using a HPLC system: Agilant 1100; mobile phase=a gradient of ACN and $H_2O$ with 1% ammonium acetate; wavelength=500 nm; flow rate=1 mL/min. Each data point was an average of three measurements. Under the HPLC conditions, the retention time of Doxorubicin was at 4.00 minutes. Separately, three different amounts of Doxorubicin (2.1, 1.1 and 0.6 mg) were mixed with HSA-based #1 gel (0.5 mL each) and ablated using the conditions described in Aim 1. Once complete, the coagulated gel impregnated with Doxorubicin was collected and placed in a citrate buffer (5 mL, pH 7) in a water bath at 36.5° C. At 1, 3, 24 and 72 h, a small quantity of solution (0.5 mL) was passed through a membrane filter (cutoff 7 KDa) and injected into the HPLC system to quantify the eluted Doxorubicin. Each data point was triplicated.

Figure 22A:
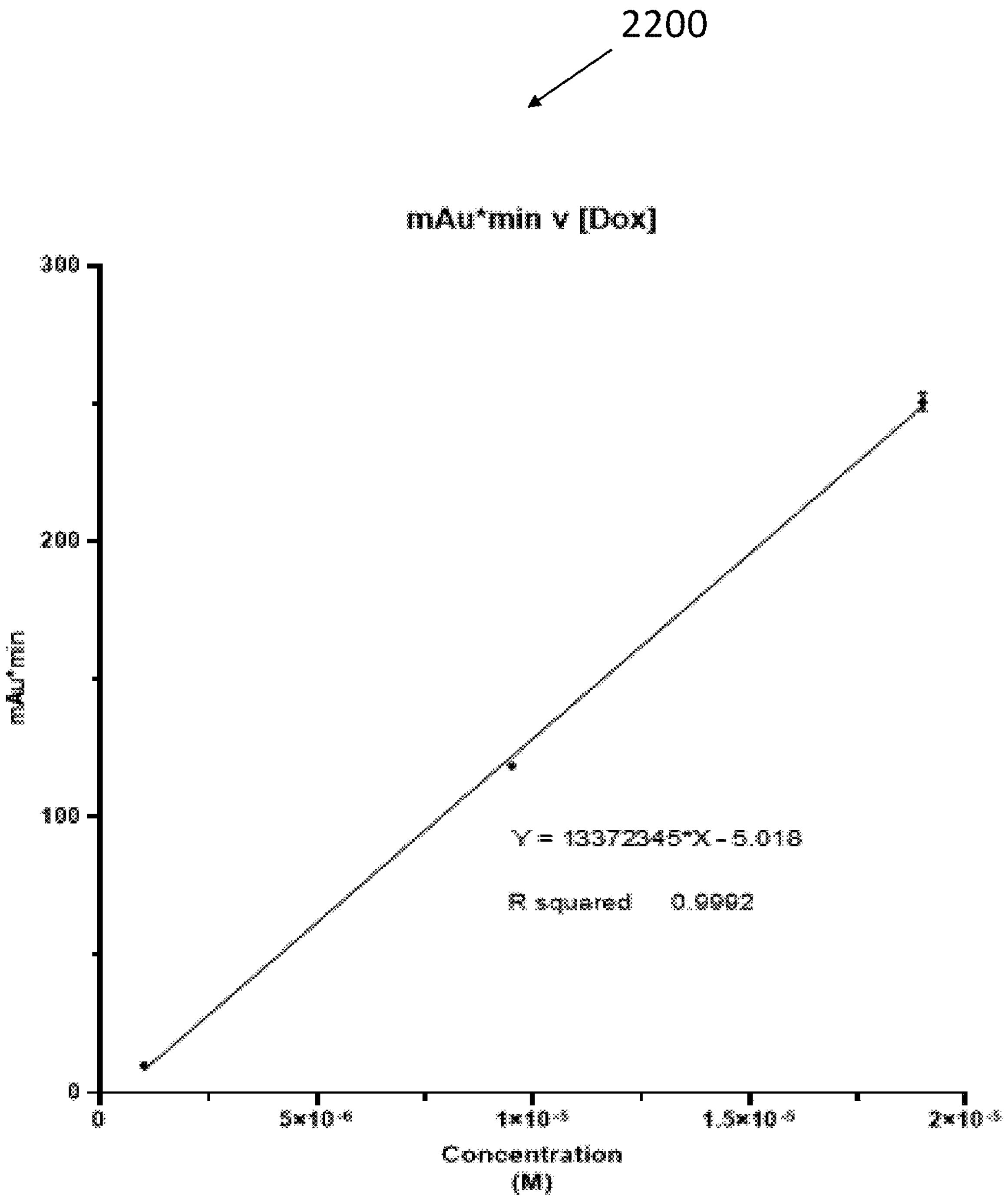
FIG. 22A shows a plot of absorbance v [Doxorubicin]
Figure 22B:
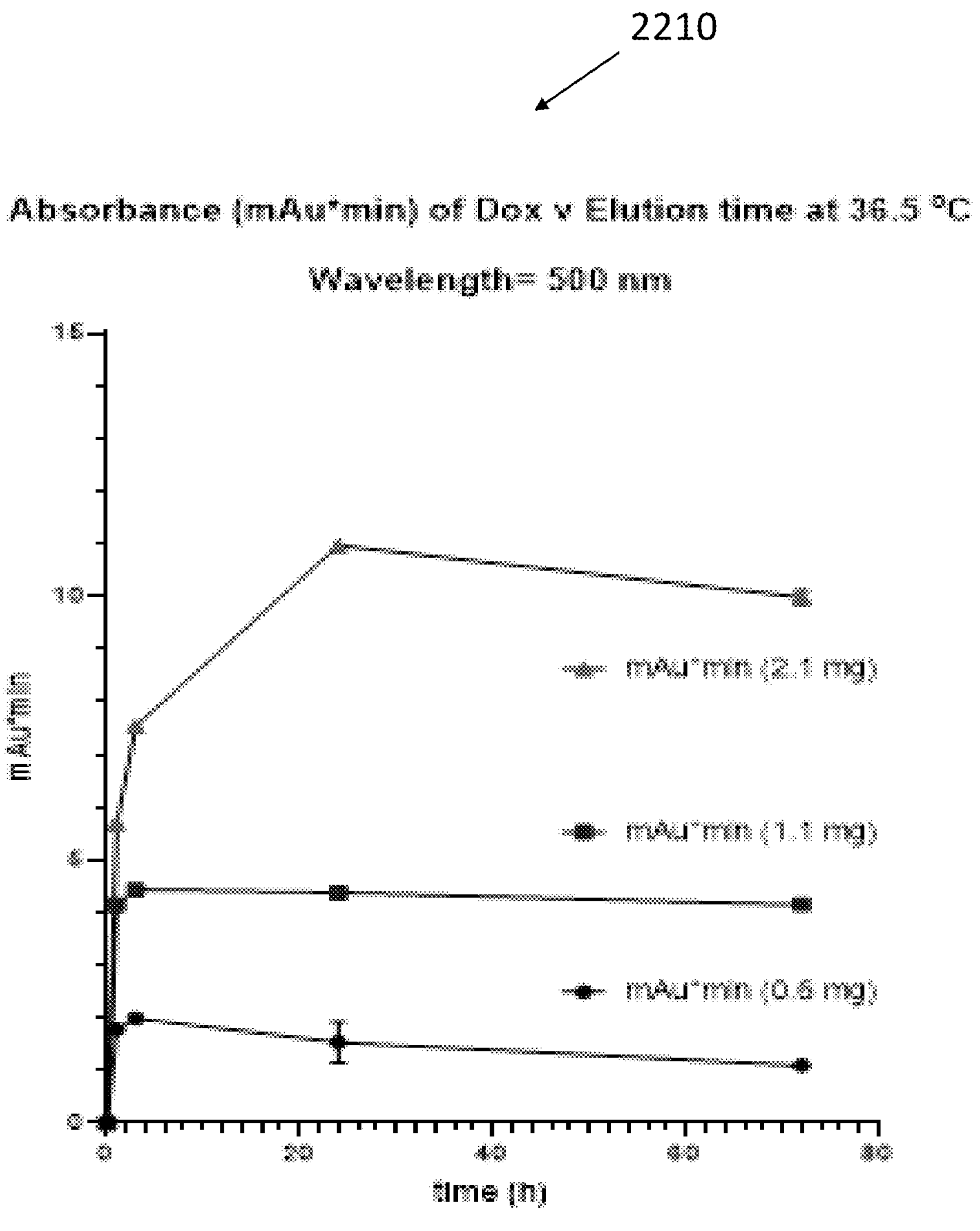
FIG. 22B shows a plot of absorbance of the eluted Doxorubicin from HSA-based #1 gel over time.

Results 2 The elution behavior of Doxorubicin is shown 2200 in FIG. 22A, which shows a plot of absorbance v [Doxorubicin]. FIG. 22B shows a plot of absorbance of the eluted Doxorubicin from HSA-based #1 gel over time (right). The drug was eluted out of the coagulated HSA-based #1 gel in a dose-dependent manner (2.1>1.1>0.6 mg) and only a part of Doxorubicin was eluted out over time (57, 64 and 87%, respectively). In addition, the elution rate was the highest at 1 h and slowed down in the order of 1>3>24>72 h.

Example 12

The following studies demonstrates that the elution of Resiquimod from the HSA-based #1 gel is dose dependent and that Resiquimod continues to be eluted from the HSA-based #1 gel after ablation.

Aim 3 In vitro elution rate of various concentrations of Resiquimod, a TLR 7/8 agonist, is determined.

Methods 3 Absorbance values of three known concentrations of Resiquimod samples (4.3x10−6, 4.3x10−5 and 8.6x10−5 M) were obtained to established a linear relationship (FIG. 23A) using the HPLC system as described in Methods 2 except wavelength=328 nm and the retention time=3.31 min.

Figure 23A:
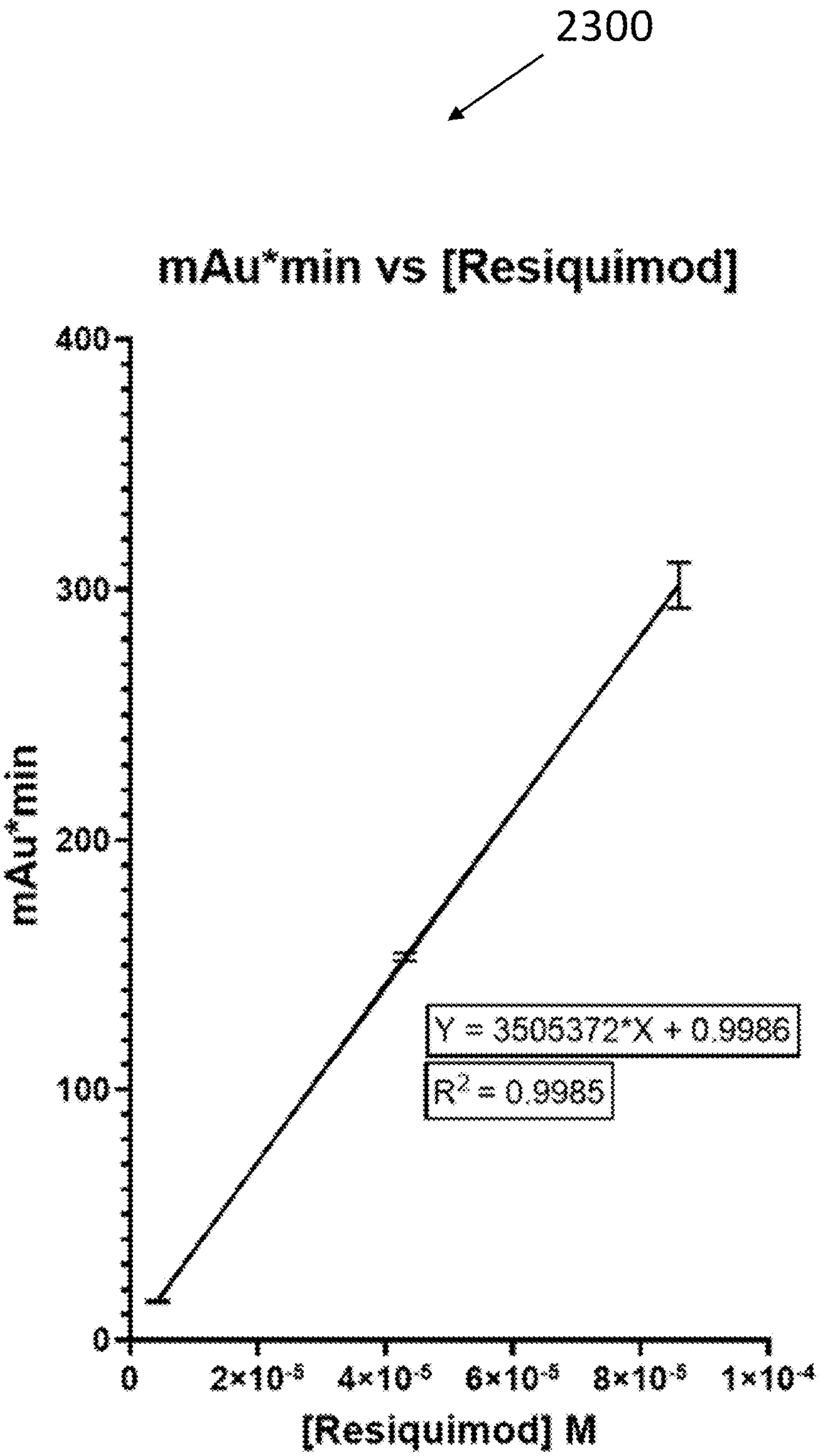
FIG. 23A shows a plot of absorbance v [Resiquimod]
Figure 23B:
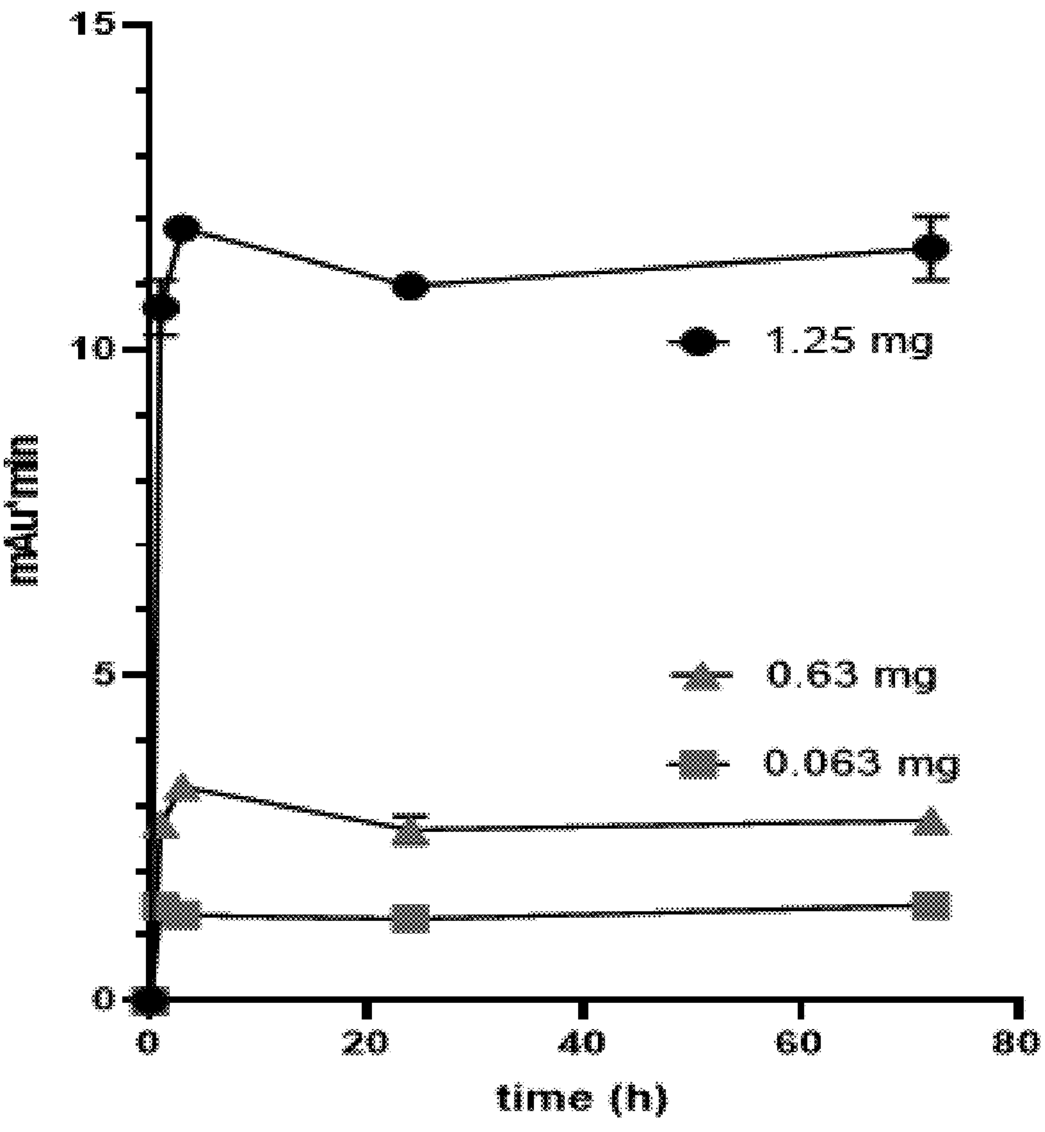
FIG. 23B shows a plot of absorbance of the eluted Resiquimod from HSA-based #1 gel over time.

Results 3 The elution behavior of Resiquimod is shown in FIG. 23A, which shows a plot of absorbance v [Resiquimod]. FIG. 23B shows plot of absorbance of the eluted Resiquimod from HSA-based #1 gel over time (right). The drug was eluted out of the coagulated HSA-based #1 gel in a dose-dependent manner (1.25>0.63>0.063 mg) and only a part of Doxorubicin was eluted out over time (57, 64 and 87%, respectively). In addition, the elution rate was the highest at 1 h and slowed down in the order of 1>3>24>72 h.

Example 13

Discussion of the Results of EXAMPLES 9 Through 12

DISCUSSION The proof-of-concept studies described in EXAMPLES 9 through 12 demonstrated that HSA-based #1 gel impregnated with drugs can perform as a combined therapeutic technology. The HSA-based #1 gel performs as a thermal accelerant to increase the effectiveness of the ablation procedure, and the gel retains selected drugs withing its structure without losing structural integrity during ablation. Furthermore, the drugs entrapped in the coagulated HSA-based #1 gel were eluted out of the protein meshwork over time and maintained the level of the elution over the observed time frame, i.e., 72 hours. Although the in vitro study design is limited to simulate the tumor environment of a living body, the present study results provide direct evidence that HSA-based #1 gel may be useful for post-ablation anti-tumor treatment to further reduction of the local recurrence rate. That is, by using the combined HSA-based #1 gel and drug composition, the effectiveness of ablation is increased and a therapeutic drug is delivered directly to the target tissue during ablation, and is eluted at the target tissue for days after ablation.

Example 14

Figure 24A:
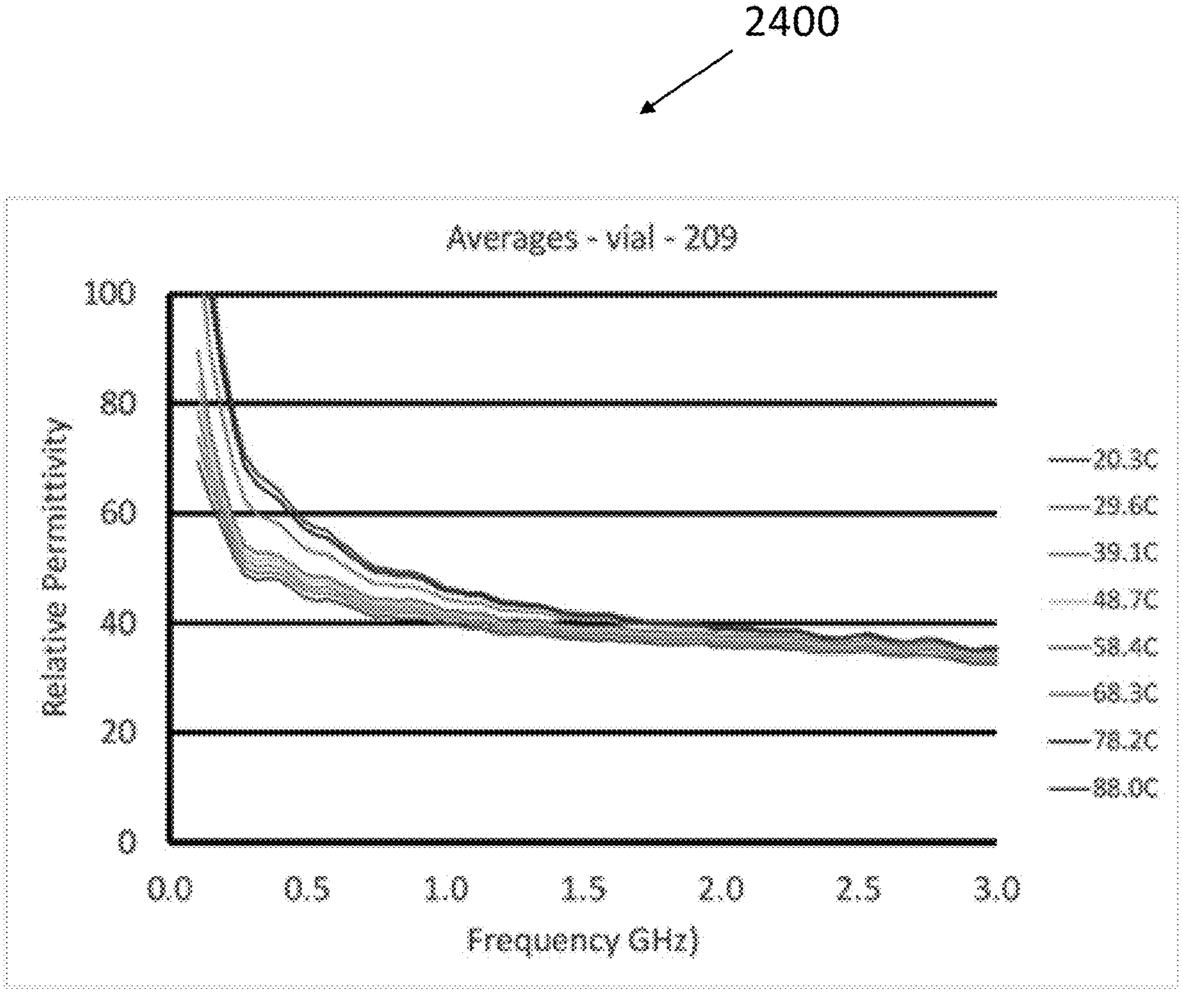
FIG. 24A shows a plot of the relative permittivity as a function of frequency for temperatures ranging from 20 C to 90 C for sample HSA209 at 915 MHz.
Figure 24B:
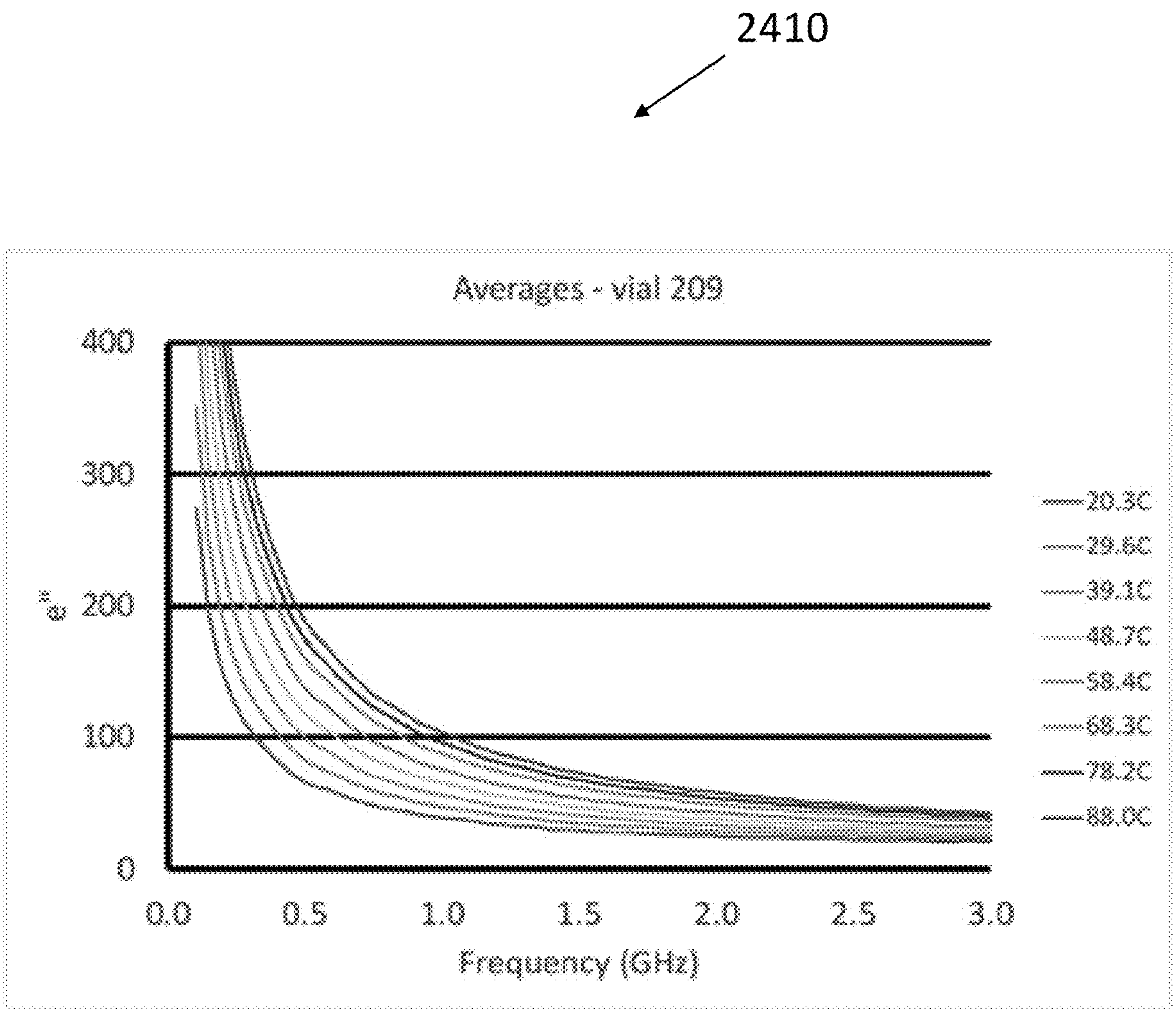
FIG. 24B shows the a plot of the e" as a function of frequency for temperatures ranging from 20 C to 90 C for sample HSA209 at 915 MHz.
Figure 24C:
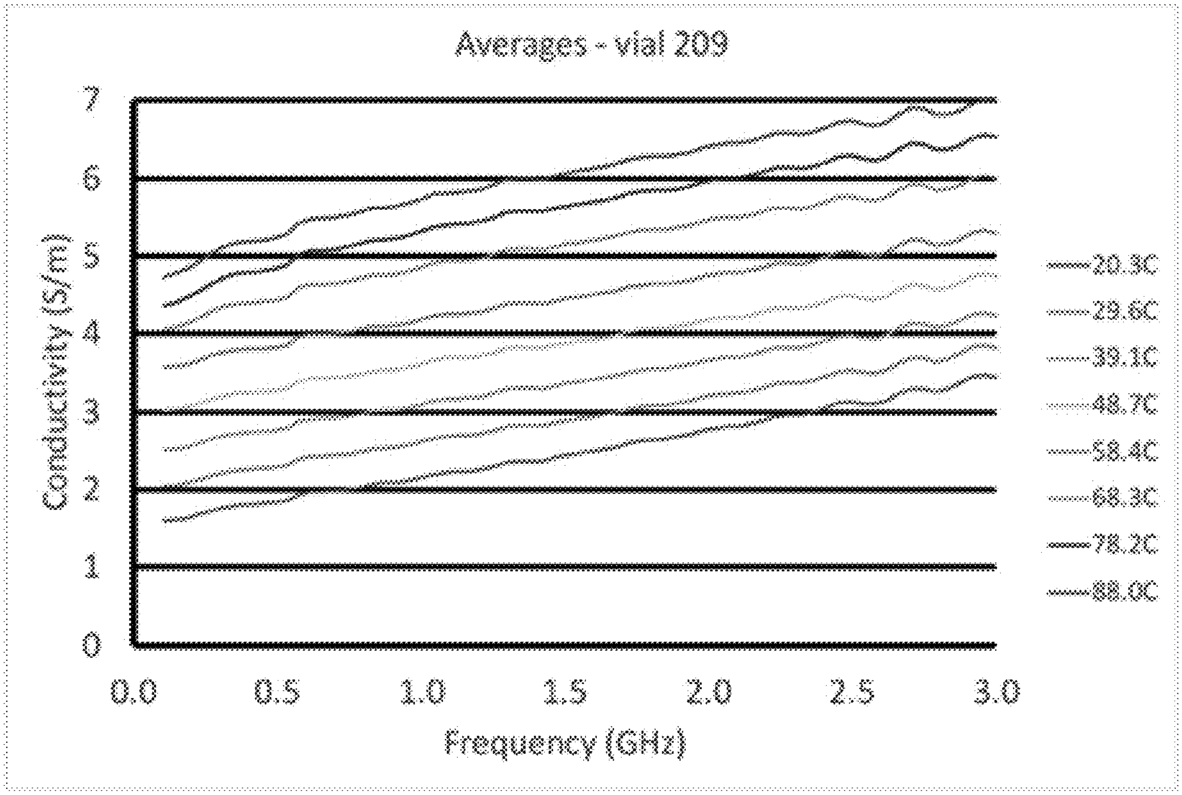
FIG. 24C shows a plot of the conductivity as a function of frequency for temperatures ranging from 20 C to 90 C for sample HSA209 at 915 MHz.

Microwave Characterization of HSA Samples Across a Broad Spectrum of Frequencies and Temperatures FIG. 24 shows the (a) relative permittivity (FIG. 24A), (b) e" (FIG. 24B), and (c) conductivity as a function of frequency for temperatures ranging from 20 C to 90 C for sample HSA209 at 915 MHz (FIG. 24C). In these cases, e" and the conductivity are essentially the same thing except for a constant and multiplication by the frequency. There is some modest ripple in the data across frequency, but that is pretty typical for this measurement technique. The results indicate a consistent and monotonic change in the properties as a function of temperature. The conductivity values are consider quite high, but high conductivity values are indicative of attenuation in the gel. Attenuation in the gel is desirable for a TA material.

FIG. 24A shows a plot of the relative permittivity as a function of frequency for temperatures ranging from 20 C to 90 C for sample HSA209 at 915 MHz.

FIG. 24B shows a plot of the e" as a function of frequency for temperatures ranging from 20 C to 90 C for sample HSA209 at 915 MHz.

FIG. 24C shows a plot of the conductivity as a function of frequency for temperatures ranging from 20 C to 90 C for sample HSA209 at 915 MHz.

The temperature dependent dielectric properties of four different HSA samples were measured at 915 and 2450 MHz. In particular, four samples were measured at temperatures between 20 C and 88 C and at 915 MHz and 2450 MHz.

Figure 25A:
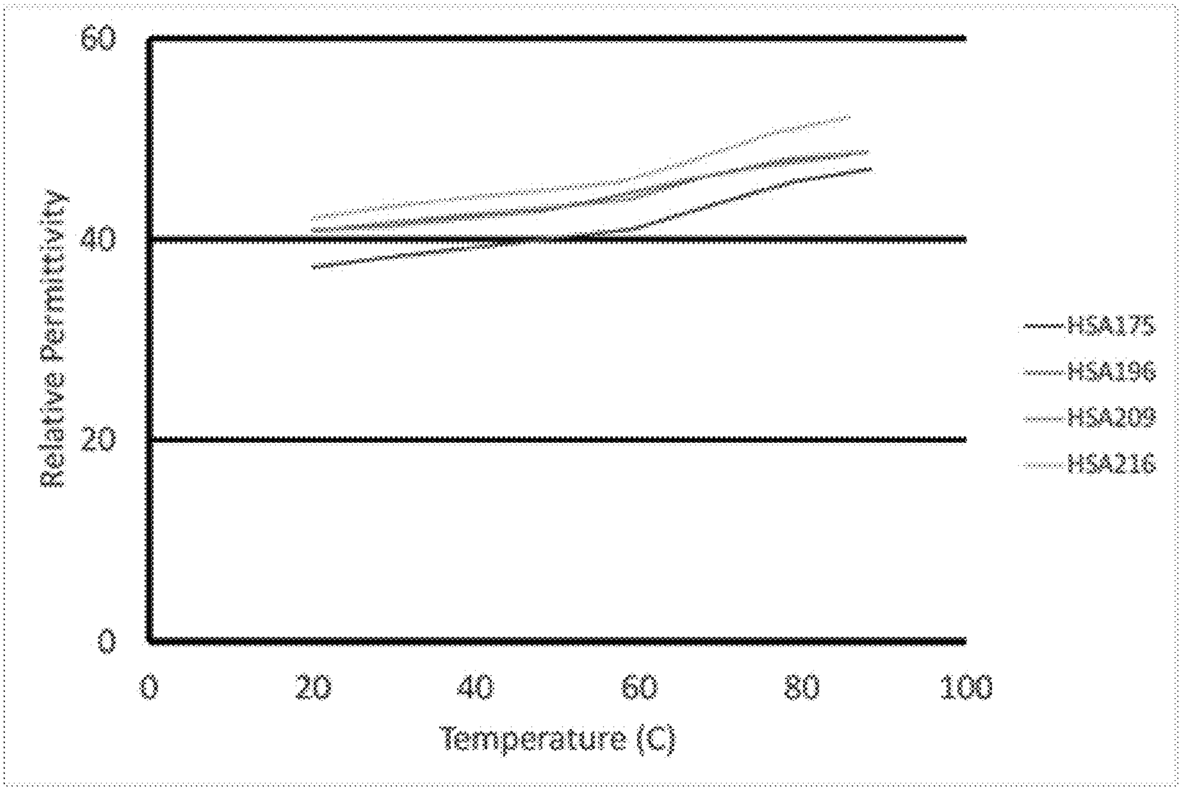
FIG. 25A shows the relative permittivity as a function of temperature ranging from 20 C to 90 C for samples HSA 175, HSA 196, HSA209, and HSA 216 at 915 MHz.
Figure 25B:
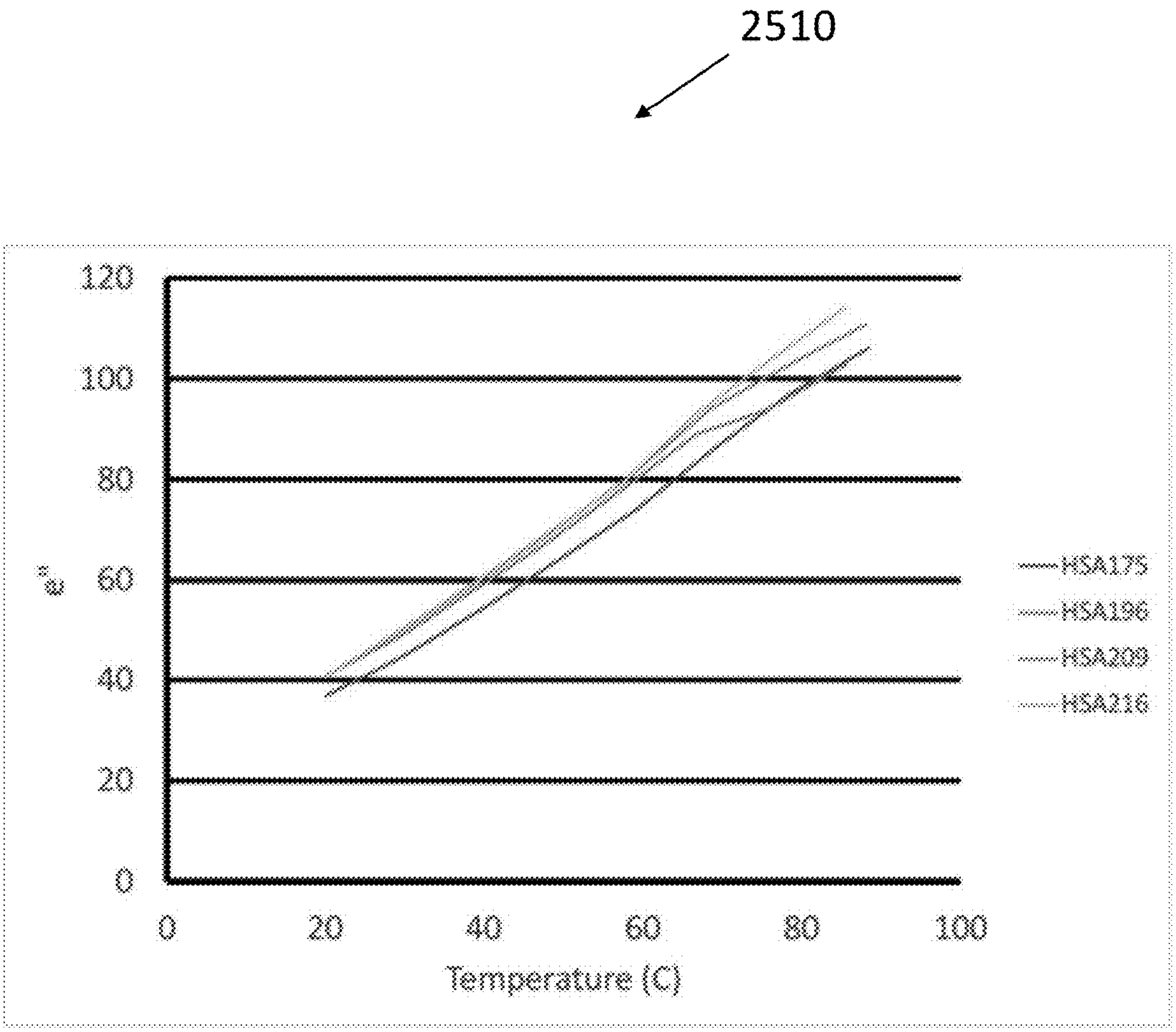
FIG. 25B shows a plot of the e" as a function of temperature ranging from 20 C to 90 C for samples HSA 175, HSA 196, HSA209, and HSA 216 at 915 MHz.
Figure 25C:
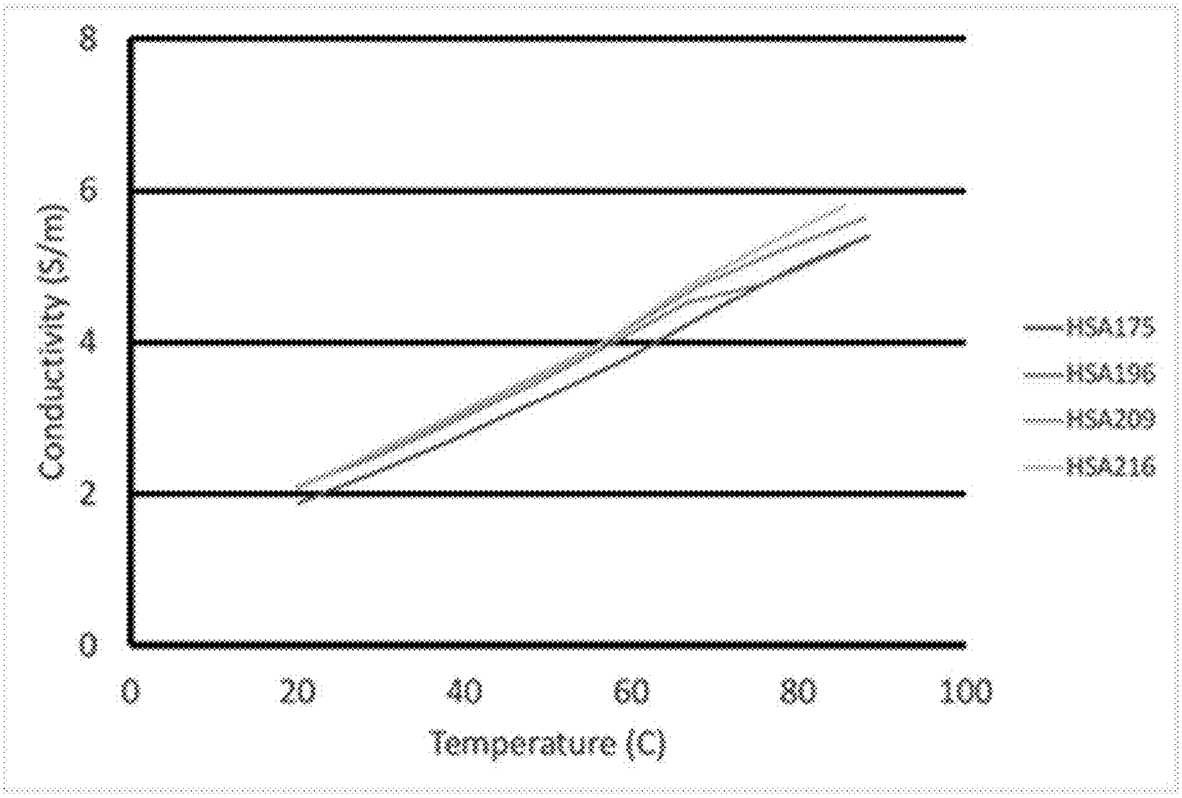
FIG. 25C shows a plot of the conductivity as a function of temperature ranging from 20 C to 90 C for samples HSA 175, HSA 196, HSA209, and HSA 216 at 915 MHz.

FIG. 25 shows the (a) relative permittivity (FIG. 25A), (b) e" (FIG. 25B), and (c) conductivity as a function of temperature ranging from 20 C to 90 C for samples HSA 175, HSA 196, HSA209, and HSA 216 at 915 MHz (FIG. 25C).

FIG. 25A shows the relative permittivity as a function of temperature ranging from 20 C to 90 C for samples HSA 175, HSA 196, HSA209, and HSA 216 at 915 MHz.

FIG. 25B shows a plot of the e" as a function of temperature ranging from 20 C to 90 C for samples HSA 175, HSA 196, HSA209, and HSA 216 at 915 MHz.

FIG. 25C shows a plot of the conductivity as a function of temperature ranging from 20 C to 90 C for samples HSA 175, HSA 196, HSA209, and HSA 216 at 915 MHz.

Figure 26A:
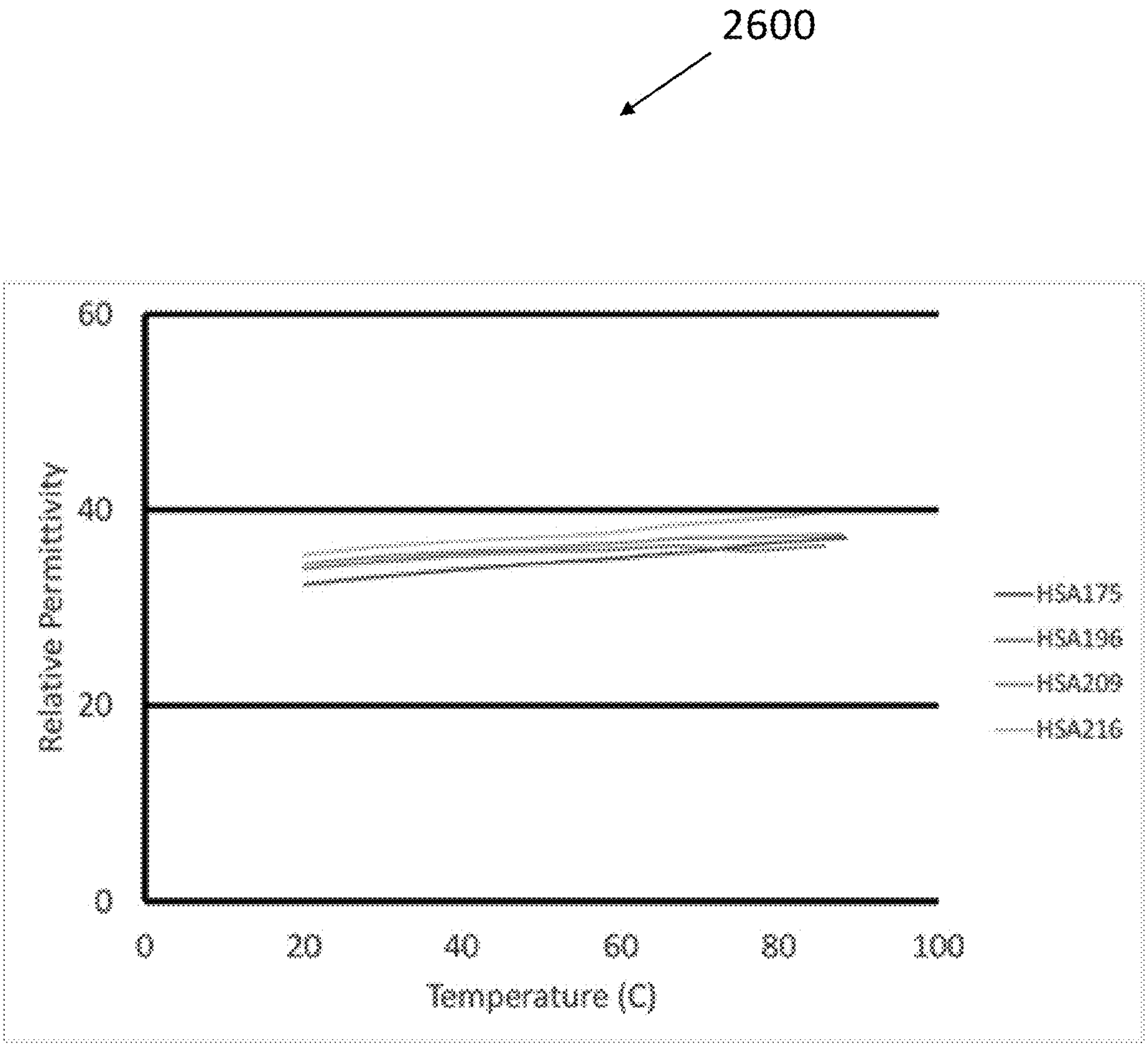
FIG. 26A shows a plot of the relative permittivity as a function of temperature ranging from 20 C to 90 C for samples HSA 175, HSA 196, HSA209, and HSA 216 at 2450 MHz.

FIG. 26 shows the (a) relative permittivity (FIG. 26A), (b) e" (FIG. 26A), and (c) conductivity as a function of temperature ranging from 20 C to 90 C for samples HSA 175, HSA 196, HSA209, and HSA 216 at 2450 MHz (FIG. 26A).

FIG. 26A shows a plot of the relative permittivity as a function of temperature ranging from 20 C to 90 C for samples HSA 175, HSA 196, HSA209, and HSA 216 at 2450 MHz.

Figure 26B:
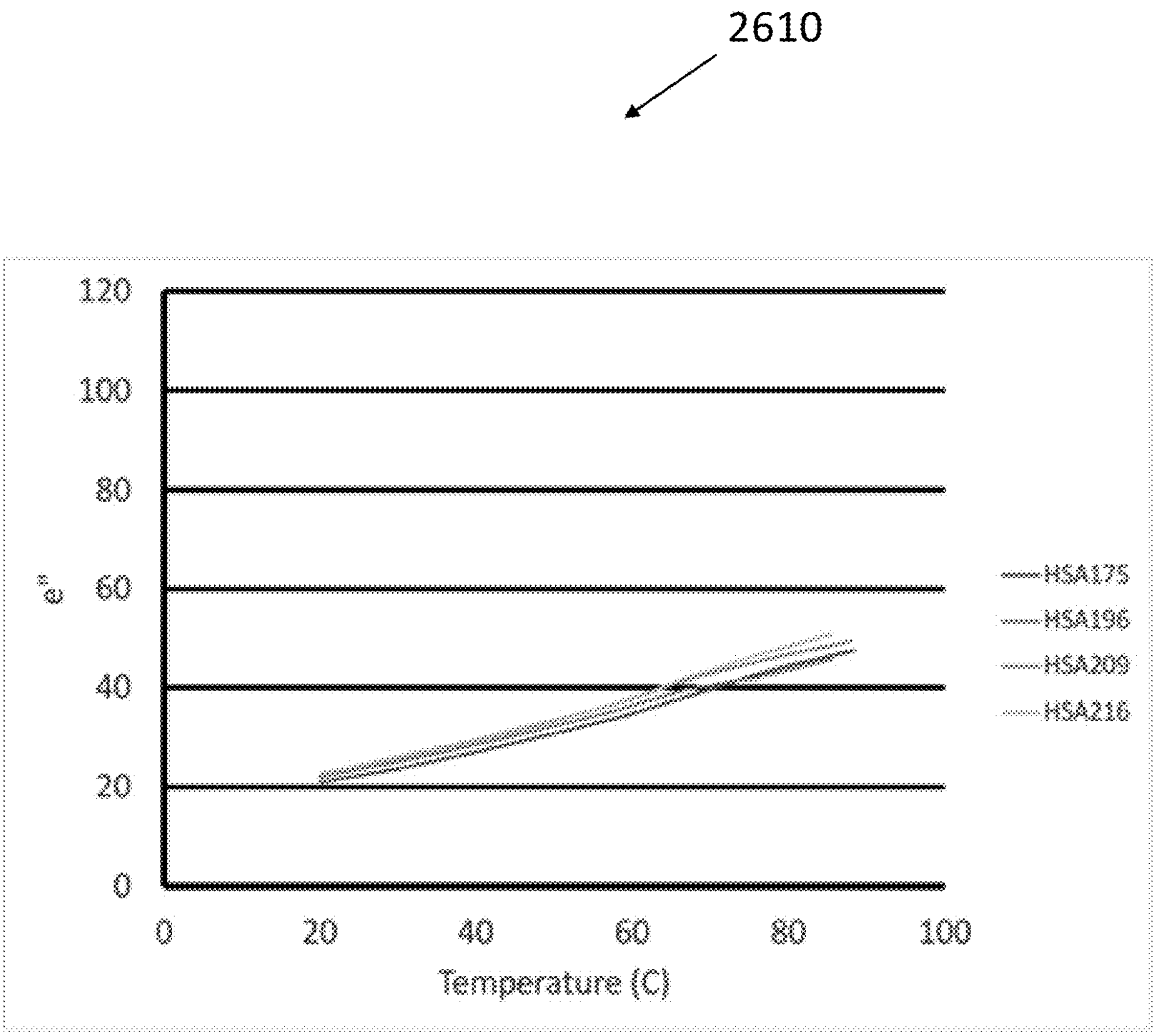
FIG. 26B shows a plot of the e" as a function of temperature ranging from 20 C to 90 C for samples HSA 175, HSA 196, HSA209, and HSA 216 at 2450 MHz.

FIG. 26B shows a plot of the e" as a function of temperature ranging from 20 C to 90 C for samples HSA 175, HSA 196, HSA209, and HSA 216 at 2450 MHz.

Figure 26C:
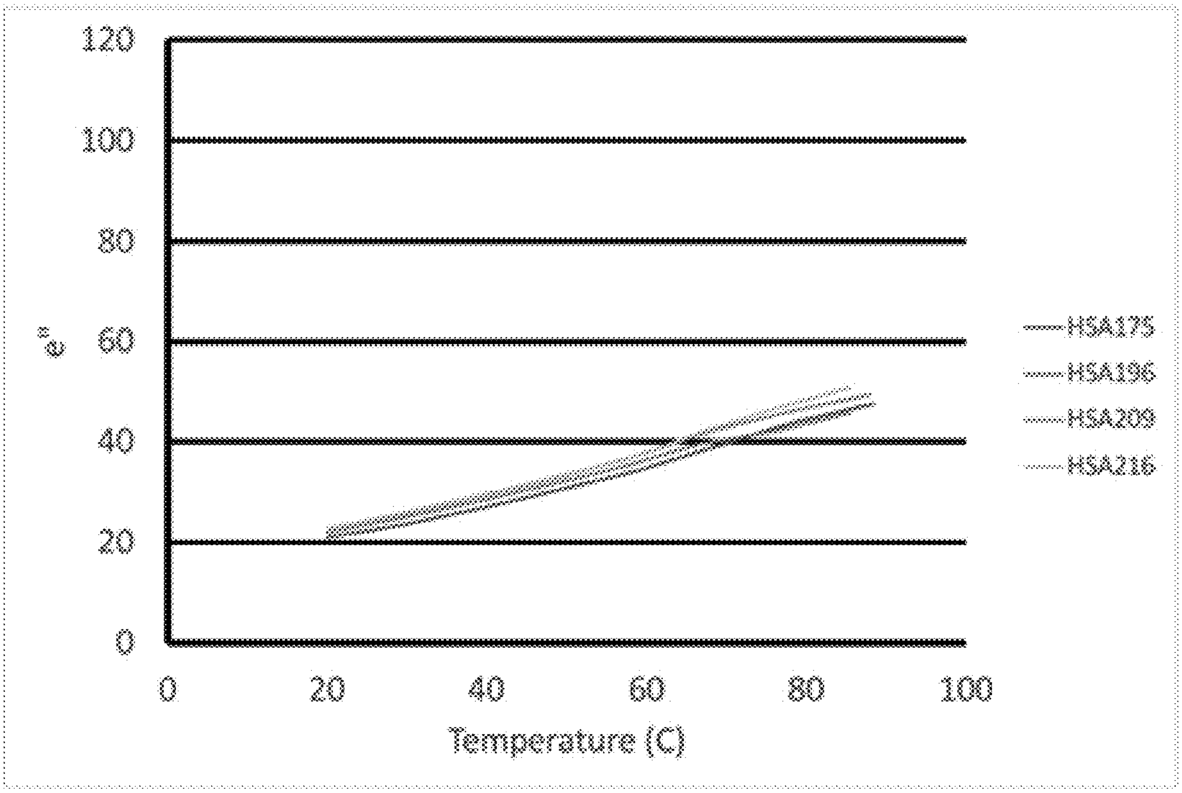
FIG. 26C shows a plot of the conductivity as a function of temperature ranging from 20 C to 90 C for samples HSA 175, HSA 196, HSA209, and HSA 216 at 2450 MHz.

FIG. 26C shows a plot of the conductivity as a function of temperature ranging from 20 C to 90 C for samples HSA 175, HSA 196, HSA209, and HSA 216 at 2450 MHz.

Overall, the trends are all nearly identical with respect to temperature and frequency. There does appear to be some offset from one sample to the next—the largest being for the permittivity. The offset variations appear to decrease substantially for the 2450 MHz case. These measurements typically should be considered accurate to within about 5%. For the reference, the electrical conductivity of pure deionized water is, 5×10−6 S/m at ambient temperature, while typical drinking water has an electrical conductivity 0.02 S/m. Our HSA-based #1 gel is about 3 S/m at ambient temperature, meaning 600,000 times greater than the deionized water and 150 times better than the drinking water with respect to the electrical conductivity. It is noteworthy that electrical conductivity of HSA-based #1 gel increases as temperature is raised at both frequencies (915 and 2450 MHz) with the similar magnitude (ca. 4 S/m). At 35° C., the electrical conductivity of HSA-based #1 gel is approximately 3-3.5 S/m, over 10 times higher than most of human tissue such as liver, lung as well as muscle as shown in the Table 4. In addition, the HSA-based #1 gel's capacity to absorb the MW energy is approximately 600K and 70 times greater than those of deionized and saline water, respectively. The fact that the electrical conductivity of HSA-based #1 gel is significantly higher than human tissue suggests that the gel can absorb the MW energy from the antenna much more efficiently than the surrounding tissue as if additional antenna is inserted at the place where HSA-based #1 gel is injected.

TABLE 4

Electrical conductivity values of various media: HSA-based #1 gel, tissues (liver, lung and muscle) and deionized water and saline solution

| Medium | Electrical Conductivity ($\sigma$, S/m) |
|---|---|
| HSA-based #1 gel | 3-3.5 |
| liver | 0.37 |
| lung | 0.46 |
| muscle | 0.36 |
| Water (deionized) | $5 \times 10^{-6}$ |
| Water (saline) | 0.05 |

Example 15

HSA-Based #1 Gel as Thermal Accelerant and Drug Delivery System

ABSTRACT It has been demonstrated above that the HSA-based #1 Gel technology enhances thermal ablation performance by eliminating the heat sink effect and improving dielectric properties of the target tissue in both MWA and RFA. The current study demonstrates that the HSA-based #1 Gel technology can be used as a thermal accelerant (TA) and a drug-eluting system (DES) during and post ablation, respectively.

To show the combined TA and DES properties, HSA-based #1 Gel was examined for two sequential events: first, the HSA-based #1 Gel, impregnated with a drug, was able to accelerate the ablation rate; second, after ablation was completed, the coagulated Gel released the drug. Here, we tested three therapeutic agents, Doxorubicin, Sorafenib and Resiquimod. Doxorubicin is a well-documented anti-tumor agent commonly used to treat cancers such as bladder, breast, lung and ovarian. Sorafenib is a protein kinase inhibitor commonly used for treating HCC. Both Doxorubicin and Sorafenib are indiscriminately cytotoxic to both healthy cells and tumor cells. Resiquimod is a TLR 7/8 agonist that is used to stimulate tumor-associated macrophages to augment the effect of immunotherapy.

As a preliminary study, the HSA-based #1 Gel was mixed with Doxorubicin HCl (Sigma-Aldrich, US) at a 1:1 ratio (biding capacity=1:1.5, respectively). The Dox-Gel (1 mL) was placed ca. 1 cm away from the antenna in an agarose phantom followed by microwave ablation (915 MHz, 60 W, 10 min, Varian, US). Post-ablation, the agarose gel was carefully cut out to isolate the coagulated Dox-Gel meshwork and transferred to a citrate buffer (ca. pH 6.8). The Dox-Gel meshwork was stirred in the buffer at 36° C. for various time intervals: 6, 12, 24, 48 and 72 h. Each sample was subjected to a filter with MW cut-off 30 k. The concentration of Doxorubicin from each filtered sample solution and the elution profile of Doxorubicin was determined using a HPLC system (at 500 nm, Agilent HPLC system 1100, US). The microwave ablation with the Dox-Gel showed a similar temperature profile as the thermal accelerant in comparison to the ablation without Dox: t@60° C. for Dox-Gel<3 min; control >10 min. The Dox-eluting profile is, 6.8%, 7%, 7.8% @ 6, 12 and 24 h post-ablation. [0181 148]

FIG. 21 shows images of the drug elution of Doxorubicin+HSA-based #1 Gel, before ablation (A), during ablation (3 min) (B), 6 h (C), 24 h (D), and 48 h (E) post ablation, respectively. The solution contained 1 (w/v) % agarose phantom. The ablation conditions: 915 MHz, 60 W for 10 minutes.

Thus, it was demonstrated that the HSA-based #1 Gel can be ablated while impregnated with drugs, e.g., Doxorubicin, Sorafenib and Resiquimod, without losing its effectiveness as a thermal accelerant. Further, the drugs trapped within the localized and coagulated Gel can be eluted to surrounding tissue at a predictable rate. Thus, this strategy can be an effective drug-delivery method for reducing devastating side-effects in treatment of various lesions by making the drug available where needed in lieu of a systemic distribution. In addition, the use of an immune modulatory drug, e.g., Resiquimod, can provide a pathway forward to improved combination immunotherapy.

Example 16

Thermally Activated Combination Therapy (TACT) of HSA-Based #1 Gel as Thermal Accelerant, Drug Delivery System, and Drug-Eluting System for Doxorubicin During and Post-Ablation It has been demonstrated above that the HSA-based #1 Gel technology enhances thermal ablation performance by eliminating the heat sink effect and improving dielectric properties of the target tissue in both MWA and RFA. This study demonstrates that the HSA-based #1 Gel technology can be used as a thermal accelerant (TA), a drug delivery system (DDS), and a drug-eluting system (DES) during and post ablation, respectively. That is, the HSA-based #1 gel technology can provide thermal accelerant (TA) advantages and provide a drug-eluting system while a target tissue is undergoing ablation therapy as well as following ablation.

To show the combined TA, DDS, and DES properties, HSA-based #1 Gel was examined for two sequential events: first, the Gel, impregnated with a drug, was able to accelerate the ablation rate; second, after ablation was completed, the coagulated Gel released the drug. Here, the drug doxorubicin was tested. Doxorubicin is a well-documented antitumor agent commonly used to treat cancers such as bladder, breast, lung and ovarian. Doxorubicin is cytotoxic to both healthy cells and tumor cells indiscriminately.

As a preliminary study, the HSA-based #1 Gel was mixed with Doxorubicin HCl (Sigma-Aldrich, US) at a 1:1 ratio (biding capacity=1:1.5, respectively). The Dox-Gel (1 mL) was placed ca. 1 cm away from the antenna in an agarose phantom followed by microwave ablation (915 MHz, 60 W, 10 min, Varian, US). Post-ablation, the agarose gel was carefully cut out to isolate the coagulated Dox-Gel meshwork and transferred to a citrate buffer (ca. pH 6.8). The Dox-Gel meshwork was stirred in the buffer at 36° C. for various time intervals: 6, 12, 24, 48 and 72 h. Each sample was subjected to a filter with MW cut-off 30 k. The concentration of Doxorubicin from each filtered sample solution and the elution profile of Doxorubicin was determined using a IPLC system (at 500 nm, a gradient of acetonitrile and water with 1% (w/v) ammonium acetate as mobile phase, Agilent IPLC system 1100, US). The microwave ablation with the Dox-Gel showed a similar temperature profile as the thermal accelerant in comparison to the ablation without Dox: t@60° C. for Dox-Gel<3 min; control >10 min. The drug was eluted out of the coagulated HSA-based #1 gel in a dose-dependent manner (2.1>1.1>0.6 mg) and only a part of Doxorubicin was eluted out over time (57, 64 and 87%, respectively). In addition, the elution rate was the highest at 1 h and slowed down in the order of 1>3>24>72 h.

Further, the effect of the coagulated Dox-Gel on tumor cells: HT29 cells was examined. The HT29 cell were divided into three groups: 1. Control; 2. Treated with Dox-Gel; 3. Cells treated with heat (47° C. in a water bath for 30 minutes)+2. To the HT29 cells grown in a 8-well plate, a known quantity of the coagulated Dox-Gel was placed for 3, 6, 24, 48 and 72 h. At each time-point, cells were stained with propidium iodide (PI) using published methods. The PI stain is a cell-impermeant dye that is excluded from viable cells with excitation and emission maxima of 535 and 617 nm with weak fluorescence on the surface of cells. Once a cell membrane has been compromised and PI can enter the cell, it intercalates with DNA, enhancing its fluorescence up to 30-fold. The three groups were quantitatively compared with respect to cell death (necrosis v apoptosis), exposure period, and the ablation-induced hyperthermal effect on tumor cells.

Thus, it was demonstrated that the HSA-based #1 Gel can be ablated while impregnated with doxorubicin without losing its effectiveness as a thermal accelerant. Further, the drugs trapped within the localized and coagulated Gel can be eluted to surrounding tissue at a predictable rate. This TACT combination strategy may be an effective drug-delivery method for reducing devastating side-effects in treatment of various lesions by making the drug available where needed in lieu of a systemic distribution. Currently, an immune modulatory drug, e.g., resiquimod, is being used to examine a pathway forward to improved "(heat+drug) combination" immunotherapy.

Example 17

Regarding treatment compositions, substances that may be used include one or more of PD-1 Pembrolizumab (Keytruda), Nivolumab (Opdivo), Cemiplimab (Libtayo), PD-L1 Atezolizumab (Tecentriq), Avelumab (Bavencio), Durvalumab (Imfinzi) and CTLA4 Ipilimumab (Yervoy), siRNA, peptides, proteins, immunogens, RNA, mRNA, DNA, or nucleoside analog-based agents.

The treatment composition may be injected separately from the combination therapy of HSA-based #1 gel including a treatment substance. Additional treatment compositions include targeting macrophages in cancer immunotherapy: additional treatment compositions include: CSF1 (MCS110); CCL2 (CNTO 888); CCR2 (BMS-813160, CCX872-B, MLN1202, PF-04136309); SIRPa (TTI-622, CC-95251, BI 765063, FSI-189); TIE 2 (CEP-11981, Regorafenib, Arry-614); Arginase (INCB001158); HER2 (CAR-macrophage); GC vitamin D-binding protein (EF-022); CD40 (SEA-CD40, APX005M, CP870,893, R07009879, CDX-1140, SGN-40, HCD122, 2141 V-11, ADC-1013, LVGN7409, Chi Lob 7/4, NG-350A); BTK (Ibrutinib, Acalabrutinib, Zanubrutinib); CSF 1R (PLX-3397, BLZ945, ARRY-382, JNJ-40346527, IMC-CS4, FPA008, R05509554, TPX-0022, DCC-3014, Q702, SNDX-6532); or CD47 (Hu5F9-G4, TTI-621, AO-176, IBI322, ZL 1201, CC-90002, HX009, IBI188, SRF231, AK117, IMC-002)

In illustrative embodiments, the cGAS-STING-TBK1 signaling pathway may be targeted with ADU-S100, MK-1454, MK-2118, BMS-986301, GSK3745417, SB-11285, IMSA-101.

In illustrative embodiments, Cancer Vaccines may include:

TLR and STING agonists: target (examples of agonists);

RIG-I/MDAS and TLR3 (poly-ICLC); TLR4 (G100); TLR7/8 (NKTR-262, resiquimod); TLR9 (CpG ODN SD-101, (VLP) excapsulated-TLR9 agonist CMP-001); STING (MK1454, E7766, ADU-S100, BMS-986301, SB-11285); FLT3L and CD40 agonists: target (examples of agonists); and rhFLT3L (CDX-301); Agonistic anti-CD40 antibody (APX005M, CDX-1140, SEA-CD40)

Example 18

The thermally-activated combination therapy (TACT) of HSA-based #1 gel including drug technology can be applied to thermal ablations of various cancer/tumor types including breast (benign and malignant, thyroid (benign and malignant), lung (primary and metastatic), liver (primary and metastatic, liver surgery margin coagulation), adrenal (benign functioning, caner and metastatic), kidney (primary and metastatic), bone, prostate, soft tissue (primary and metastatic). This TACT can be further applied to non-cancer treatment areas with therapeutics that help assist healing the treatment area such as anti-infective or anti-inflammatory agents.

In illustrative embodiments, this thermally-activated combination therapy can be further applied to endometrial ablation/menorrhagia, and be used to treat the uterus.

In illustrative embodiments, this thermally-activated combination therapy can be further applied to spinal decompression and denervation, and be used to treat a vertebral body.

In illustrative embodiments, this thermally-activated combination therapy can be further applied to Benign Prostatic Hyperplasia (BPH).

In illustrative embodiments, this thermally-activated combination therapy can be further applied to esophagus (reflux), bronchial tree (emphysema reduction), biliary tree (stent obstruction from tumor), joints (laxity), surgical resection and bleeding as cauterization agent.

The embodiments described above are intended to be merely exemplary; numerous variations and modifications will be apparent to those skilled in the art. Such variations and modifications are intended to be within the scope of illustrative embodiments as defined by any of the appended claims.

What is claimed is:

1. A drug delivery composition comprising:

a carrier that includes a polymer configured to coagulate when exposed to prescribed energy from an energy source to become relatively immobilized after being positioned within a target site;

a chaotrope configured to adjust the charge distribution within the carrier; and a drug configured to be associated with the carrier, the drug being configured to be released following exposure of the prescribed energy from the energy source, wherein the carrier is configured to be structurally altered upon exposure to the prescribed energy from the energy source to release the drug.

2. The composition of claim 1, wherein the drug is configured such that a portion of the drug is released from the carrier over at least 48 hours.

3. The composition of claim 1, wherein a concentration of the carrier can range from approximately 30 mg/mL to approximately 600 mg/mL.

4. The composition of claim 1, wherein the drug is associated with the carrier by at least one of protein binding or covalent bonding.

5. The composition of claim 1, wherein the polymer comprises albumin or structurally modified albumin.

6. The composition of claim 1, wherein structurally altered comprises denaturation of the carrier.

7. The composition of claim 6, wherein denaturation of the carrier alters at least one of:

a protein binding percentage between the drug and the carrier; or a shape of the carrier.

8. The composition of claim 1, wherein the energy source includes one or more of microwave, radiofrequency, electrical pulse or sonar.

9. The composition of claim 1, wherein the drug includes one or more of PD-1 Pembrolizumab, Nivolumab, Cemiplimab, PD-L1 Atezolizumab, Avelumab, Durvalumab (Imfinzi) and CTLA4 Ipilimumab siRNA, peptides, proteins, immunogens, RNA, mRNA, DNA, or nucleoside analog-based agents.

10. The composition of claim 1, wherein the drug includes one or more of kinase inhibitors, or doxorubicin, taxol, or other non-kinase anti-tumor agents.

11. The composition of claim 1, wherein the polymer comprises one or more of DNA, RNA, glycoproteins or glycopolymers such as IgA, IgG, or other immunoglobulins.

12. The composition of claim 1, wherein the drug comprises a drug for targeting macrophages in cancer immunotherapy comprises one or more of: CSF1; CCL2; CCR2; SIRPa; TIE 2; Arginase; HER2; GC vitamin D-binding protein; CD40; BTK; CSF IR; or CD47.

13. The composition of claim 1, wherein the drug comprises a drug for targeting cGAS-STING-TBK1 signaling pathway with at least one or more of ADU-SIO0, MK-1454, MK-2118, BMS-986301, GSK3745417, SB-11285, orIMSA-101.

14. The composition of claim 1, wherein the drug comprises a drug for cancer vaccines TLR and STING agonists: target RIG-I/MDAS and TLR3; TLR4; TLR7/8; TLR9; STING FLT3L and CD40 agonists: target rhFLT3L; Agonistic anti-CD40 antibody.

15. A thermally-activated combined treatment composition, comprising:

a therapeutic agent; and a thermal accelerant configured to:

enhance ablation treatment;

be impregnated with the therapeutic agent; and elute the therapeutic agent after exposure to energy from an energy source, wherein:

the combined treatment composition is thermally activated by exposure to energy from an energy source; and after the thermal accelerant is exposed to the energy from the energy source:

the thermal accelerant is configured to become coagulated and becomes coupled with the ablated tissue; and the thermal accelerant is configured to begin to elute a portion of therapeutic agent.

16. The composition of claim 15, wherein the therapeutic agent is associated with the thermal accelerant by at least one of protein binding or covalent bonding.

17. A thermally-activated combined treatment composition, comprising:

a therapeutic agent; and a thermal accelerant configured to:

enhance ablation treatment;

be impregnated with the therapeutic agent; and elute the therapeutic agent after exposure to energy from an energy source, wherein:

the combined treatment composition is thermally activated by exposure to energy from an energy source; and
the thermal accelerant comprises:
a carrier comprising an albumin;
an ionic component comprising at least one chaotrope; and
an imaging component.

18. The composition of claim 17, wherein:
the albumin comprises human serum albumin or bovine serum albumin;
the chaotrope comprises at least one of calcium chloride, cesium chloride, lithium chloride, potassium chloride, rubidium chloride, sodium chloride, sodium citrate, trisodium citrate, sodium tryptophanate, citric acid, octanoic acid, or a combination thereof; and
the imaging component comprises at least one of NaCl, CsCl, or albumin.

19. The composition of claim 18, wherein, when the thermal accelerant is exposed to
the energy source;
the energy source is configured to begin to denature the albumin; and
the denatured albumin is configured to:
become coagulated; and
release the impregnated drug.

* * * * *